United States Patent
Ohkawa et al.

(10) Patent No.: US 6,872,718 B1
(45) Date of Patent: Mar. 29, 2005

(54) TRICYCLIC DIHYDROBENZOFURAN DERIVATIVES, PROCESS FOR THE PREPARATION THEREOF AND AGENTS

(75) Inventors: Shigenori Ohkawa, Takatsuki (JP); Tadatoshi Hashimoto, Ibaraki (JP); Tetsuya Tsukamoto, Akashi (JP)

(73) Assignee: Takeda Chemical Industries, Ltd., Osaka (JP)

( * ) Notice: Subject to any disclaimer, the term of this patent is extended or adjusted under 35 U.S.C. 154(b) by 50 days.

(21) Appl. No.: 10/069,180

(22) PCT Filed: Aug. 18, 2000

(86) PCT No.: PCT/JP00/05523

§ 371 (c)(1),
(2), (4) Date: Feb. 15, 2002

(87) PCT Pub. No.: WO01/14384

PCT Pub. Date: Mar. 1, 2001

(30) Foreign Application Priority Data

Aug. 20, 1999 (JP) .............................. 11-234718

(51) Int. Cl.[7] ................. D07D 491/048; A61K 31/407; A61K 31/4741; A61K 31/55; A61P 25/00
(52) U.S. Cl. .................... 514/220; 514/291; 514/411; 540/586; 546/90; 548/430
(58) Field of Search ................ 514/220, 291, 514/411; 540/586; 546/90; 548/430

(56) References Cited

U.S. PATENT DOCUMENTS

| 3,773,769 A | 11/1973 | Albrecht | 260/287 |
|---|---|---|---|
| 4,008,237 A | 2/1977 | Agui | 260/287 |
| 5,420,289 A | 5/1995 | Musser et al. | 548/159 |
| 5,478,844 A | 12/1995 | Aono et al. | 514/320 |

FOREIGN PATENT DOCUMENTS

| AU | 491943 | 9/1976 |
|---|---|---|
| EP | 0 345 593 A1 | 12/1989 |
| EP | 0 992 496 A1 | 4/2000 |
| GB | 1 556 747 | 11/1979 |
| JP | 50 117908 | 9/1975 |
| JP | 50 117909 | 9/1975 |

OTHER PUBLICATIONS

Delanty, N. et al, Arch. Neorol., 57, 2000, pp. 1265–1270.*
Solin, M.L. et al, Kidney Int., 59, 2001, 481–487, abstract PMID 11168930 PubMed.*
Roberts et al. "Differential effects of 5–HT 1B/1D receptor antagonists in dorsal and media raphe innervated brain regions" Eur. J. Pharmacology 346:175–180 (1998).

* cited by examiner

*Primary Examiner*—James O. Wilson
*Assistant Examiner*—Thomas McKenzie
(74) *Attorney, Agent, or Firm*—Elaine M. Ramesh; Mark Chao

(57) ABSTRACT

A compound represented by the formula:

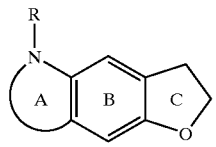

wherein Ring A is a non-aromatic 5- to 7-membered nitrogen-containing heterocyclic ring which may be further substituted, Ring B is benzene ring which is further substituted, Ring C is a dihydrofuran-ring which may be further substituted and R is hydrogen atom or an acyl group or a salt thereof has an excellent lipid peroxidation inhibitory activity and is useful as a lipid peroxidation inhibitor.

20 Claims, No Drawings

TRICYCLIC DIHYDROBENZOFURAN DERIVATIVES, PROCESS FOR THE PREPARATION THEREOF AND AGENTS

This application is the National Stage of International Application Serial No. PCT/JP00/05523, filed Aug. 18, 2000.

FIELD OF THE INVENTION

The present invention relates to a novel tricyclic dihydrobenzofuran derivative having an excellent lipid peroxidation inhibitory activity, a process for preparing the same and a pharmaceutical composition containing the same.

BACKGROUND OF THE INVENTION

As it has been revealed that formation of active oxygen species in the living body and accompanying formation of peroxylipid have a variety of adverse influences on the living body through membrane disorder or enzyme disorder, various attempts have been made to apply lipid peroxidation inhibitory agents to pharmaceuticals. Currently, as, lipid peroxidation inhibitory agents used in the pharmaceutical field, derivatives of natural antioxidants such as vitamin C, vitamin E and β-carotene, etc. and phenol derivatives are mainly known (authored by Kenji Fukuzawa, Nippon Rinsho vol.46, pp 2269–2276, 1988 and Sies, H., Stahl, W., Sundquist, A. R., Ann. N. Acad. Sci., vol.669, 7–20, 1992). However, these have insufficient activities and have side effects and, therefore, they are not necessarily satisfactory practically.

On the other hand, JP-A-52-23096 discloses, as a furo[2,3-f]quinoline derivative, a quinoline carboxylic acid derivative represented by the formula:

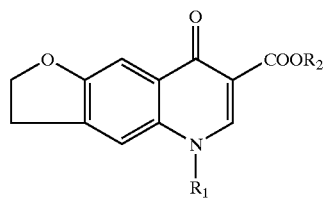

wherein $R_1$ is an unsaturated, straight or branched alkyl group having 1 to 6 carbon atoms and $R_2$ is hydrogen or a saturated or unsaturated, straight or branched alkyl group having 1 to 6 carbon atoms, and a physiologically acceptable salt with an inorganic or organic base when $R_2$ represent hydrogen atom, a method for preparing the same and an agent for treating a urinary tract infection containing the same, together with a typically exemplified compound represented by the formula:

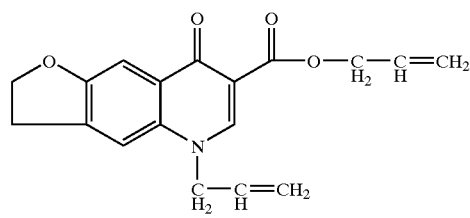

and the like.

JP-A-50-117908 discloses a veterinarian antibacterial formulation comprising as an effective ingredient a quinolone carboxylic acid derivative represented by the formula:

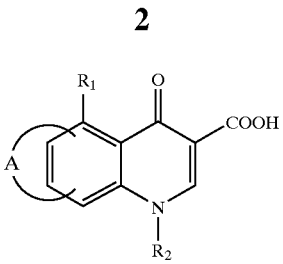

wherein A is an alkylene group having 2 to 3 carbon atoms (provided that this alkylene group may contain 1 or 2 oxygen atoms at the terminal or halfway of its carbon chain), and this alkylene group is bound to two adjacent carbon atoms on the benzene ring; $R_1$ is hydrogen atom or amino group, and $R_2$ is a lower alkoxy group, a lower aminoalkyl group or a lower alkenyl group when $R_1$ is hydrogen atom, while $R_2$ is an alkyl group when $R_1$ is amino group, together with a typically exemplified compound represented by the formula:

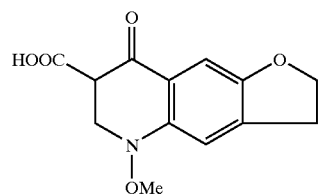

and the like.

JP-A-50-117909 discloses an agent for preventing or treating ichthyic bacterial diseases containing as an effective ingredient a quinolone carboxylic acid represented by the formula:

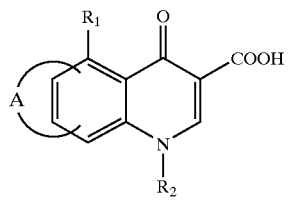

wherein A is an alkylene group having 2 to 3 carbon atoms (provided that this alkylene group may contain 1 or 2 oxygen atoms at the terminal or halfway of its carbon chain), and this alkylene group is bound to two adjacent carbon atoms on the benzene ring; $R_1$ is hydrogen atom or amino group, and $R_2$ is a lower alkoxy group, a lower aminoalkyl group or a lower alkenyl group when $R_1$ is hydrogen atom, while $R_2$ is an alkyl group when $R_1$ is amino group, together with a typically exemplified compound represented by the formula:

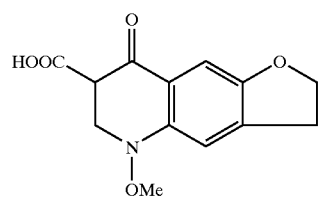

and the like.

JP-A-47-1081 discloses a method for preparing a quinoline carboxylic acid represented by the formula:

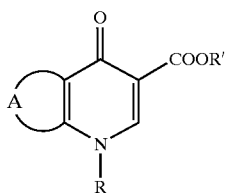

wherein each of R and $R^1$ denotes hydrogen atom or an alkyl group, and A denotes a divalent group:

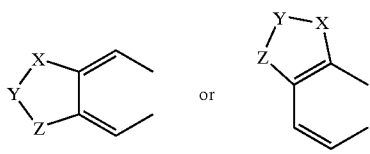

wherein X, Y and Z are taken together to form a dihydrofuran ring such that —X—Y—Z— is —O—CH$_2$—CH$_2$— or CH$_2$—O—CH$_2$— and wherein a ring formed by X, Y and Z may be substituted with 1 to 3 oxo groups, and a salt thereof with an inorganic or organic base, together with a typically exemplified compound represented by the formula:

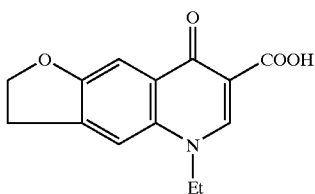

and the like.

JP-A49-30369 discloses a method for preparing a quinoline carboxylic acid derivative represented by the formula:

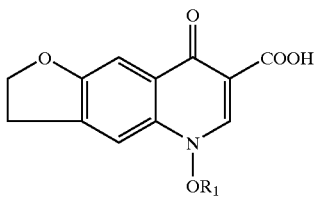

wherein $R_1$ is a lower alkyl group, which comprises reacting a 1-hydroxy-4-quinolone 3-carboxylic acid derivative represented by the formula:

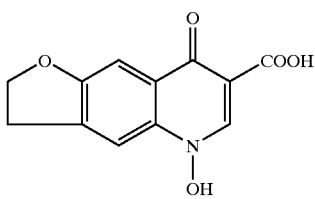

with an alkylating agent to form a quinoline carboxylic acid derivative represented by the formula:

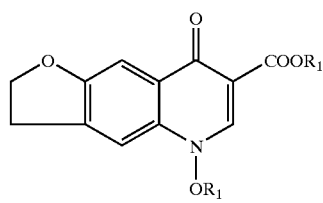

wherein $R_1$ is as defined above, followed by hydrolyzing, together with a typically exemplified compound represented by the formula:

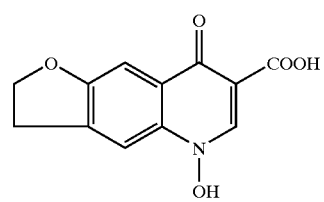

and the like.

European Journal of Pharmacology (1988), 346(2/3), 175-180 discloses as a furo[2,3-f]indole derivative having an antidepressive activity a compound represented by the formula:

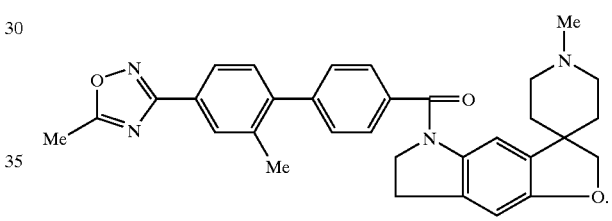

A lipid peroxidation inhibitor (antioxidant) which has a lipid peroxidation inhibitory activity based on an excellent antioxidative effect and which exhibits an excellent pharmacokinetic profile is expected to exhibit an excellent effect in prophylaxis or therapy against a central nerve system disease (for example, ischemic central nerve disease (e.g., cerebral infarction, cerebral hemorrhage, cerebral edema), central nerve damage (e.g., cranial trauma, spinal damage, whiplash), neurodegenerative disease (e.g., Alzheimer's disease, Parkinson's disease, Huntington's chorea, amyotrophic lateral sclerosis), vascular dementia (e.g., multi-infarct dementia, Binswanger's disease), manic-depressive, melancholia, schizophrenia, chronic pain, trigeminal neuralgia, migraine and the like), a circulatory system disease or failure (for example, ischemic heart disease (e.g., cardiac infarction, angina pectoris), arterial sclerosis, post-PCTA (percutaneous transluminal coronary angioplasty) arterial restenosis, lower urinary tract disease or failure (e.g., dysuria, urinary incontinence) and the like), diabetic neurosis and the like.

Nevertheless, a fully satisfactory substance has not been identified yet, and thus a compound having an excellent lipid peroxidation inhibitory activity and which is fully satisfactory as a pharmaceutical is expected to be developed.

DISCLOSURE OF THE INVENTION

The present inventors studied intensively to obtain a compound having a lipid peroxidation inhibitory activity. As a result, the present inventors succeeded for the first time in synthesis of a compound characterized by a chemical structure in which a nitrogen-containing non-aromatic heterocyclic ring is fused to a dihydrobenzofuran at its 5- and 6-positions and has substituents on its 4-position and/or para-position (thus having a substituent on Ring B as shown in the following formula), represented by the formula:

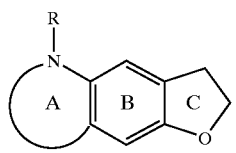

wherein Ring A is a non-aromatic 5- to 7-membered nitrogen-containing heterocyclic ring which may be further substituted, Ring B is benzene ring which is substituted, Ring C is a dihydrofuran ring which may be further substituted and R is hydrogen atom or an acyl group or a salt thereof (hereinafter sometimes abbreviated as Compound (I)), and also found that each of these novel compounds possesses an unexpectedly excellent lipid peroxidation inhibitory activity based on its specific chemical structure and that a compound represented by the formula:

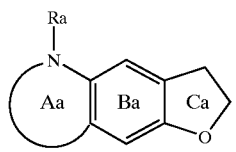

wherein Ring Aa is a non-aromatic 5- to 7-membered nitrogen-containing heterocyclic ring which may be further substituted, Ring Ba is benzene ring which may be further substituted, Ring Ca is a dihydrofuran ring which may be further substituted and Ra is hydrogen atom or an acyl group, including Compound (I), or a salt thereof (hereinafter sometimes abbreviated as Compound (I')) possesses an excellent lipid peroxidation inhibitory activity and is effective in its nature as a pharmaceutical employed clinically, thus completing the present invention.

That is, the present invention is:

(1) Compound (I),
(2) the compound according to the abovementioned (1), wherein Ring A is a non-aromatic 5- to 7-membered nitrogen-containing heterocyclic ring which may be further substituted by an optionally substituted hydrocarbon group,
(3) the compound according to the above-mentioned (1), wherein Ring A is a non-aromatic 5- to 7-membered nitrogen-containing heterocyclic ring which may be further substituted by an optionally substituted lower alkyl group,
(4) the compound according to the above-mentioned (1), wherein Ring A is a non-aromatic 5- to 7-membered nitrogen-containing heterocyclic ring which may be further substituted by a lower alkyl group,
(5) the compound according to the above-mentioned (1), wherein Ring A is a non-aromatic 5-membered nitrogen-containing heterocyclic ring which may be further substituted by a lower alkyl group,
(6) the compound according to the above-mentioned (1) represented by the formula:

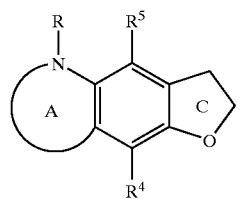

wherein $R^4$ and $R^5$ are the same or different and each denotes hydrogen atom, a halogen atom, hydroxy group, amino group or a hydrocarbon group which may be bonded directly or via oxygen atom, nitrogen atom or sulfur atom and which may be substituted, and the other symbols are as defined above, provided that both $R^4$ and $R^5$ are not hydrogen atoms at the same time, or a salt thereof, (7) the compound according to the above-mentioned (6), wherein $R^4$ and $R^5$ are the same or different and each denotes a lower alkyl group or a lower alkoxy group,
(8) the compound according to the above-mentioned (6), wherein each of $R^4$ and $R^5$ is a lower alkyl group,
(9) the compound according to the above-mentioned (1) represented by the formula:

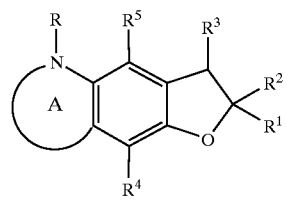

wherein $R^1$ and $R^2$ are the same or different and each denotes hydrogen atom, an optionally esterified or amidated carboxyl group or an optionally substituted hydrocarbon group, $R^3$ is hydrogen atom, an optionally substituted hydrocarbon group or an optionally substituted amino group, and other symbols are as defined above, or a salt thereof,

(10) the compound according to the above-mentioned (9), wherein $R^1$ is a lower alkyl group, $R^2$ is a lower alkyl group which may be substituted by a halogen atom, hydroxy group or an optionally substituted cyclic amino group and $R^3$ is hydrogen atom or an optionally substituted phenyl group,
(11) the compound according to the above-mentioned (9), wherein $R^1$ is a lower alkyl group, $R^2$ is a lower alkyl group which may be substituted by a halogen atom, a hydroxy group or optionally substituted cyclic amino group, $R^3$ is hydrogen atom or an optionally substituted phenyl group, each of $R^1$ and $R^5$ is a lower alkyl group, and Ring A is a non-aromatic 5- to 7-membered nitrogen-containing heterocyclic ring which may be further substituted by a lower alkyl group,
(12) the compound according to the above-mentioned (9), wherein $R^1$ is a lower alkyl group, $R^2$ is a lower alkyl group which may be substituted by a halogen atom, hydroxy group or an optionally substituted cyclic amino group, $R^3$ is hydrogen atom or an optionally substituted phenyl group, each of $R^1$ and $R^5$ is a lower alkyl group, and Ring A is a non-aromatic 5-membered nitrogen-containing heterocyclic ring which may be further substituted by a lower alkyl group,
(13) the compound according to the above-mentioned (1) which is 8-tert-butyl-3,5,6,7-tetrahydro-2,2,4,6,6-pentamethyl-2H-furo[2,3-f]indole or a salt thereof,

(14) the compound according to the above-mentioned (1) which is 3,5,6,7-tetrahydro-2,4,8-trimethyl-2-[(4-phenylpiperidino)methyl]-2H-furo[2,3-f]indole or a salt thereof,

(15) the compound according to the above-mentioned (1) which is 3,5,6,7-tetrahydro-2,4,6,6,8-pentamethyl-2-[(4-phenylpiperidino)methyl-2H-furo[2,3-f]indole or a salt thereof,

(16) the compound according to the above-mentioned (1) which is 3,5,6,7-tetrahydro-2,3,4,8-tetramethyl-3-(4-methylphenyl)-2H-furo[2,3-f]indole or a salt thereof,

(17) a prodrug of Compound (I),

(18) a method for producing Compound (I) which comprises subjecting a substituent X and hydroxy group on Ring B in a compound represented by the formula:

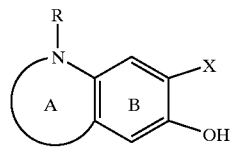

wherein X is an optionally substituted allyl group, and the other symbols are as defined above, or a salt thereof to a ring-closure reaction,

(19) a pharmaceutical composition comprising Compound (I) or a prodrug thereof,

(20) a prophylactic and therapeutic agent against a cerebrovascular impairment, a cranial trauma or a neurodegenerative disease comprising Compound (I') or a prodrug thereof,

(21) a prophylactic and therapeutic agent according to the above-mentioned (20), wherein said neurodegenerative disease is Parkinson's disease or Alzheimer's disease,

(22) a prophylactic and therapeutic agent against a dysuria or a urinary incontinence comprising Compound (I') or a prodrug thereof,

(23) a prophylactic and therapeutic agent against a restenosis after a percutaneous transluminal coronary angioplasty comprising Compound (I') or a prodrug thereof,

(24) a lipid peroxidation inhibitor comprising Compound (I') or a prodrug thereof,

(25) a method for preventing or treating a cerebrovascular impairment, a cranial trauma or a neurodegenerative disease which comprises administering Compound (I') or a prodrug thereof to a mammal,

(26) a method for preventing or treating a dysuria or a urinary incontinence which comprises administering Compound (I') or a prodrug thereof to a mammal,

(27) a method for preventing or treating a restenosis after a percutaneous transluminal coronary angioplasty which comprises administering Compound (I') or a prodrug thereof to a mammal,

(28) a method for inhibiting formation of a peroxylipid, which comprises administering an effective amount of Compound (I') or a prodrug thereof to a mammal,

(29) use of Compound (I') or a prodrug thereof for manufacturing a prophylactic and therapeutic agent against a cerebrovascular impairment, a cranial trauma or a neurodegenerative disease,

(30) use of Compound (I') or a prodrug thereof for manufacturing a prophylactic and therapeutic agent against a dysuria or a urinary incontinence.

(31) use of Compound (I') or a prodrug thereof for manufacturing a prophylactic and therapeutic agent against a restenosis after a percutaneous transluminal coronary angioplasty, and,

(32) use of Compound (I') or a prodrug thereof for manufacturing a lipid peroxidation inhibitor, and the like.

The term "hydrocarbon group" in "optionally substituted hydrocarbon group" used herein include, for example, a linear or cyclic hydrocarbon group (for example, alkyl, alkenyl, alkynyl, cycloalkyl, aryl, aralkyl, etc.). Among them, a linear or cyclic hydrocarbon group having 1 to 16 carbon atoms listed below or the like is preferred.

(i) a lower alkyl (for example, a $C_{1-6}$ alkyl such as methyl, ethyl, propyl, isopropyl, butyl, isobutyl, sec-butyl, tert-butyl, pentyl hexyl, etc., or the like), (ii) a lower alkenyl (for example, a $C_{2-6}$ alkenyl such as vinyl, allyl, isopropenyl, butenyl, isobutenyl, sec-butenyl, etc., or the like), (iii) a lower alkynyl (for example, a $C_{2-6}$ alkynyl such as ethynyl, 1-propynyl, propargyl, butynyl, 1-hexynyl, etc., or the like), (iv) a $C_{3-6}$ cycloalkyl (for example, cyclopropyl, cyclobutyl, cyclopentyl, cyclohexyl, cycloheptyl, etc.), (v) a $C_{6-14}$ aryl (for example, phenyl, 1-naphthyl, 2-naphthyl, biphenylyl, 2-anthryl, etc., preferably phenyl, etc.), (vi) a $C_{7-16}$ aralkyl (for example, benzyl, phenethyl, diphenylmethyl, 1-naphthylmethyl, 2-naphthylmethyl, 2,2-diphenylethyl, 3-phenylpropyl, 4-phenylbutyl, 5-phenylpentyl, etc., preferably benzyl, etc.).

Examples of the "substituent" which may be possessed by said "hydrocarbon group" include (1) a halogen atom (for example, fluorine, chlorine, bromine, iodine, etc.), (2) an optionally halogenated lower alkyl, (3) a lower alkenyl (for example, a $C_{2-6}$ alkenyl such as vinyl, allyl, isopropenyl, butenyl, isobutenyl, sec-butenyl, etc., or the like), (4) a lower alkynyl U, (for example, a $C_{2-6}$ alkynyl such as ethynyl, 1-propynyl, propargyl, butynyl, 1-hexynyl, etc., or the like), (5) a cycloalkyl (for example, a $C_{3-6}$ cycloalkyl such as cyclopropyl, cyclobutyl, cyclopentyl, cyclohexyl, etc., or the like), (6) an aryl (for example, a $C_{6-10}$ aryl such as phenyl, 1-naphthyl, 2-naphthyl, biphenylyl, 2-anthryl, etc., or the like), (7) an aralkyl (for example, $C_{7-11}$ aralkyl such as benzyl, phenethyl, diphenylmethyl, 1-naphthylmethyl, 2-naphthylmethyl, 2,2-diphenylethyl, 3-phenylpropyl, 4-phenylbutyl, 5-phenylpentyl, etc., or the like), (8) an optionally halogenated lower alkoxy, (9) an aryloxy (for example, a $C_{6-10}$ aryloxy such as phenoxy, etc., or the like), (10) a lower alkanoyl (for example, a $C_{1-6}$ alkyl-carbonyl such as acetyl, propionyl, butyryl, isobutyryl, etc., or the like), (11) an arylcarbonyl (for example, a $C_{6-10}$ aryl-carbonyl such as benzoyl., naphthoyl, etc., or the like), (12) a lower alkanoyloxy (for example, a $C_{1-6}$ alkyl-carbonyloxy such as acetyloxy, propionyloxy, butyryloxy, isobutyryloxy, etc., or the like), (13) an arylcarbonyloxy (for example, a $C_{6-10}$ aryl-carbonyloxy such as benzoyloxy, naphthoyloxy, etc., or the like), (14) carboxyl, (15) a lower alkoxycarbonyl (for example, a $C_{1-6}$ alkoxy-carbonyl such as methoxycarbonyl, ethoxycarbonyl, propoxycarbonyl, isopropoxycarbonyl, butoxycarbonyl, isobutoxycarbonyl, tert-butoxycarbonyl, etc., or the like), (16) carbamoyl, thiocarbamoyl, (17) a mono-lower alkylcarbamoyl (for example, a mono-$C_{1-6}$ alkyl-carbamoyl such as methylcarbamoyl, ethylcarbamoyl, etc.), (18) a di-lower alkylcarbamoyl (for example, a di-$C_{1-6}$ alkyl-carbamoyl such as dimethylcarbamoyl, diethylcarbamoyl, etc.), (19) a $C_{6-10}$ aryl-carbamoyl (for example, phenylcarbamoyl, naphthylcarbamoyl, etc.), (20) amidino, (21) imino, (22) amino, (23) a mono-lower alkylamino (for example, a mono-$C_{1-6}$ alkylamino such as methylamino, ethylamino, propylamino, isopropylamino, butylamino, etc.), (24) a di-lower alkylamino (for example, a di-$C_{1-6}$ alkylamino such as dimethylamino, diethylamino, ethylmethylamino, dipropylamino, diisopropylamino, dibutylamino, etc., or the like), (25) an alkylenedioxy (for example, a $C_{1-3}$ alkylenedioxy such as methylenedioxy, ethylenedioxy, etc., or the like), (26) hydroxy group, (27) nitro, (28) cyano, (29) mercapto, (30) sulfo, (31) sulfino, (32) phosphono, (33) sulfamoyl, (34) a mono-lower alkylsulfamoyl (for example, a mono-$C_{1-6}$ alkylsulfamoyl such as methylsulfamoyl, ethylsulfamoyl, propylsulfamoyl, isopropylsulfamoyl, butylsulfamoyl, etc., or the like), (35) a di-lower alkylsulfamoyl (for example, a di-$C_{1-6}$ alkylsulfamoyl such as dimethylsulfamoyl, diethylsulfamoyl, dipropylsulfamoyl, dibutylsulfamoyl, etc., or the like), (36) an optionally halogenated lower alkylthio, (37) an arylthio (for example, a $C_{6-10}$ arylthio such as phenylthio, naphthylthio, etc., or the like), (38) a lower alkylsulfinyl (for example, a $C_{1-6}$ alkylsulfinyl such as methylsulfinyl, ethylsulfinyl, propylsulfinyl, butylsulfinyl, etc. or the like), (39) an arylsulfinyl (for example, a $C_{6-10}$ arylsulfinyl such as phenylsulfinyl, naphthylsulfinyl, etc., or the like), (40) a lower alkylsulfonyl (for example, a $C_{1-6}$ alkylsulfonyl such as methylsulfonyl, ethylsulfonyl, propylsulfonyl, butylsulfonyl, etc., or the like), (41) an arylsulfonyl (for example, a $C_{6-10}$ arylsulfonyl such as phenylsulfonyl, naphthylsulfonyl, etc., or the like), (42) an optionally substituted heterocyclic group, (43) oxo, and the like. When a substituent is (25) an alkylenedioxy, then it preferably forms a ring together with two adjacent carbon atoms.

Examples of "(2) optionally halogenated lower alkyl" as the substituent on "hydrocarbon group" include a lower alkyl (for example, a $C_{1-6}$ alkyl such as methyl, ethyl, propyl, isopropyl, butyl, isobutyl, sec-butyl, tert-butyl, pentyl, hexyl, etc., or the like) which may have one to three halogen atoms (for example, fluorine, chlorine, bromine, iodine, etc.), and specific examples thereof are methyl, chloromethyl, difluoromethyl, trichloromethyl, trifluoromethyl, ethyl, 2-bromoethyl, 2,2,2-trifluoroethyl, propyl, 3,3,3-trifluoropropyl, isopropyl, butyl, 4,4,4-trifluorobutyl, isobutyl, sec-butyl, tert-butyl, pentyl, isopentyl, neopentyl, 5,5,5-trifluoropentyl, hexyl, 6,6,6-trifluorohexyl, etc., preferably methyl, etc.

Examples of "(8) optionally halogenated lower alkoxy" as the substituent on "hydrocarbon group" include a lower alkoxy (for example, a $C_{1-6}$ alkoxy such as methoxy, ethoxy, propoxy, isopropoxy, butoxy, isobutoxy, sec-butoxy, tert-butoxy, etc., or the like) which may have one to three halogen atoms (for example, fluorine, chlorine, bromine, iodine, etc.), and specific examples thereof are methoxy, difluoromethoxy, trifluoromethoxy, ethoxy, 2,2,2-trifluoroethoxy, propoxy, isopropoxy, butoxy, 4,4,4-trifluorobutoxy, isobutoxy, sec-butoxy, pentyloxy, hexyloxy, etc.

Examples of "(36) optionally halogenated lower alkylthio" as the substituent on "hydrocarbon group" include a lower alkylthio (for example, a $C_{1-6}$ alkylthio such as methylthio, ethylthio, propylthio, isopropylthio, butylthio, sec-butylthio, tert-butylthio, etc. or the like) which may have one to three halogen atoms (for example, fluorine, chlorine, bromine, iodine, etc.), and specific examples thereof are methylthio, difluoromethylthio, trifluoromethylthio, ethylthio, propylthio, isopropylthio, butylthio, 4,4,4-trifluorobutylthio, pentylthio, hexylthio, etc.

Examples of "(42) optionally substituted heterocyclic group" as the substituent on "hydrocarbon group" include those defined by the term "optionally substituted heterocyclic group" used herein.

Examples of "heterocyclic group" in the term "optionally substituted heterocyclic group" used herein include an aromatic heterocyclic group, a saturated or unsaturated non-aromatic heterocyclic group containing as ring-constituting atoms (ring atoms), at least one (preferably 1 to 4, more preferably one to two) atom of one to three species (preferably one to two species) of the heteroatoms selected from oxygen, sulfur and nitrogen atoms.

Examples of the "aromatic heterocyclic group" include a 5- or 6-membered aromatic monocyclic heterocyclic group such as furyl, thienyl, pyrrolyl, oxazolyl, isooxazolyl, thiazolyl, isothiazolyl, imidazolyl, pyrazolyl, 1,2,3-oxadiazolyl, 1,2,4-oxadiazolyl, 1,3,4-oxadiazolyl, furazanyl, 1,2,3-thiadiazolyl, 1,2,4-thiadiazolyl, 1,3,4-thiadiazolyl, 1,2,3-triazolyl, 1,2,4-triazolyl, tetrazolyl, pyridyl, pyridazinyl, pyrimidinyl, pyrazinyl, triazinyl, etc., a 8- to 12-membered aromatic fused heterocyclic group such as benzofuranyl, isobenzofuranyl, benzothienyl, indolyl, isoindolyl, 1H-indazolyl, benzindazolyl, benzoxazolyl, 1,2-benzoisoxazolyl, benzothiazolyl, 1,2-benzoisothiazolyl, 1H-benzotriazolyl, quinolyl, isoquinolyl, cinnolinyl, quinazolinyl, quinoxalinyl, phthalazinyl, naphthylidinyl, purinyl, pteridinyl, carbazolyl, α-carbolinyl, β-carbolinyl, γ-carbolinyl, acridinyl, phenoxazinyl, phenothiazinyl, phenazinyl, phenoxthinyl, thianthrenyl, phenathridinyl, phenathrolinyl, indolidinyl, pyrrolo[1,2-b]pyridazinyl, pyrrazolo[1,5-a]pyridyl, imidazo[1,2-a]pyridyl, imidazo[1,5-a]pyridyl, imidazo[1,2-b]pyridazinyl, imidazo[1,2-a]pyrimidinyl, 1,2,4-triazolo[4,3-a]pyridyl, 1,2,4-triazolo[4,3-b]pyridazinyl, 1,2,4,5-tetrahydro-3H-3-benzazepin-3-yl, etc. (preferably, a heterocyclic ring formed by a condensation of a 5- to 6-membered aromatic monocyclic heterocyclic group described above with benzene ring, or a heterocyclic ring formed by a condensation of two of the same or different heterocyclic rings of 5- to 6-membered aromatic monocyclic heterocyclic groups described above), and the like.

Examples of the "non-aromatic heterocyclic group" include a 3- to 8-membered (preferred 5- to 6-membered) saturated or unsaturated (preferably saturated) non-aromatic heterocyclic group such as oxiranyl, azetidinyl, oxetanyl, thietanyl, pyrrolidinyl, tetrahydrofuryl, thiolanyl, piperidyl, tetrahydropyranyl, morpholinyl, thiomorpholinyl, piperazinyl, etc., and the like.

Examples of the "substituent" which may be possessed by said "heterocyclic group" include (1) an optionally substituted alkyl group, (2) an optionally substituted amino group, (3) an optionally substituted aryl group, (4) an optionally substituted cycloalkenyl group, (5) an optionally substituted cycloalkyl group, (6) an optionally substituted alkenyl group, (7) an optionally substituted alkynyl group, (8) an optionally substituted amidino group, (9) an optionally substituted hydroxy group, (10) an optionally substituted thiol group, (11) an optionally esterified carboxyl group, (12) an optionally substituted carbamoyl group, (13) an optionally substituted thiocarbamoyl group, (14) an acyl group, (15) a halogen atom (for example, fluorine, chlorine, bromine, iodine, etc., preferably chlorine, bromine, etc.), (16) cyano group, (17) nitro group, etc., each of which may occur 1 to 5 times (preferably 1 to 3 times) in any substitutable positions.

Examples of "(1) alkyl group" as the substituent on "heterocyclic group" include a $C_{1-6}$ alkyl such as methyl, ethyl, n-propyl, isopropyl, n-butyl, isobutyl, sec-butyl, tert-butyl, n-pentyl, isopentyl, neopentyl, 1-methylpropyl, n-hexyl, isohexyl, 1,1-dimethylbutyl, 2,2-dimethylbutyl, 3,3-dimethylbutyl, 3,3-dimethylpropyl, etc., and the like.

Examples of the substituent on "(1) alkyl group" include a lower alkoxy (for example, a $C_{1-6}$ lower alkoxy such as methoxy, ethoxy, propoxy, etc., or the like), a halogen (for example, fluorine, chlorine, bromine, iodine, etc.), a lower alkyl (for example, a $C_{1-6}$ alkyl such as methyl, ethyl, propyl, etc., or the like) and an aralkyloxy (for example a $C_{7-16}$ aralkyloxy such as benzyloxy, etc., or the like) which may be substituted by a substituent selected from amino, hydroxy group, cyano, amidino and an aryl (for example, a $C_{6-14}$ aryl such as phenyl, etc., or the like), each of which may occur 1 to 2 times in any substitutable positions.

Examples of "(3) aryl group" as the substituent on "heterocyclic group" include a $C_{6-14}$ aryl group such as phenyl, 1-naphthyl, 2-naphthyl, biphenylyl, 2-anthryl, etc., and the like. Examples of the substituent on "(3) aryl group" include the same substituents as those on "(1) alkyl group" described above and the number of the substituent is the same as that of "(1) alkyl group".

Examples of "(4) cycloalkenyl group" as the substituent on "heterocyclic group" include a $C_{3-6}$ cycloalkenyl group such as cyclopropenyl, cyclobutenyl, cyclopentenyl, cyclohexenyl, etc., and the like. Examples of the substituent on "(4) cycloalkenyl group" include the same substitutents as those on "(1) alkyl group" described above and the number of the substituent is the same as that of "(1) alkyl group".

Examples of "(5) cycloalkyl group" as the substituent on "heterocyclic group" include a $C_{3-7}$ cycloalkyl group such as cyclopropyl, cyclobutyl, cyclopentyl, cyclohexyl, cycloheptyl, etc., and the like. Examples of the substituent on "(2) cycloalkenyl group" include the same substituents as those on "(1) alkyl group" described above and the number of the substituent is the same as that of "(1) alkyl group".

Examples of "(6) alkenyl group" as the substituent on "heterocyclic group" include a $C_{2-6}$ alkenyl group such as vinyl, allyl, isopropenyl, 2-methylallyl, 1-propenyl, 2-methyl-1-propenyl, 1-butenyl, 2-butenyl, 3-butenyl, 2-ethyl-1-butenyl, 2-methyl-2-butenyl, 3-methyl-2-butenyl, 1-pentenyl, 2-pentenyl, 3-pentenyl, 4-pentenyl, 4-methyl-2-pentenyl, 1-hexenyl, 2-hexenyl, 3-hexenyl, 4-hexenyl, 5-hexenyl, etc., and the like. Examples of the substituent on "(6) alkenyl group" include the same substituents as those on "(1) alkyl group" described above and may occur similar times.

Examples of "(7) alkynyl group" as the substituent on "heterocyclic group" include a $C_{2-6}$ alkynyl group such as ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, 5-hexynyl, etc., and the like. Examples of the substituent on "(7) alkynyl group" include the same substituents as those on "(1) alkyl group" described above and the number of the substituent is the same as that of "(1) alkyl group".

Examples of the substituent on "(2) amino group", "(8) amidino group", "(9) hydroxy group" and "(10) thiol group" as the substituent include a lower alkyl group (for example, a $C_{1-6}$ alkyl group such as methyl, ethyl, propyl, isopropyl, butyl, isobutyl, tert-butyl, pentyl, hexyl, etc., or the like), an acyl group (a $C_{1-6}$ alkanoyl group (e.g., formyl, acetyl, propionyl, pivaloyl, etc.), benzoyl, or the like), an optionally halogenated $C_{1-6}$ alkoxy-carbonyl (for example, trifluoromethoxycarbonyl, 2,2,2-trifluoroethoxycarbonyl, trichloromethoxycarbonyl and 2,2,2-trichloroethoxycarbonyl, etc.) and the like, and any of these substituents may be further substituted with an aryl group (for example, a $C_{6-10}$ aryl group such as phenyl, 1-naphthyl, 2-naphthyl, etc., or the like), a heterocyclic group, and the like. Examples of the "heterocyclic group" include the same group as the "heterocyclic group" in "optionally substituted heterocyclic group" described above. Further, "(2) amino group" as the substituent may sometimes form a cyclic amino group when two substituents are taken together with nitrogen atom, and in such case, examples of the cyclic amino group include a 3- to 8-membered (preferably 5- to 6-membered) cyclic amino group such as 1-azetidinyl, 1-pyrrolidinyl, piperidino, morpholino, 1-piperazinyl as well as 1-piperazinyl which may have in its 4-position a lower alkyl group (for example a $C_{1-6}$ alkyl group such as methyl, ethyl, propyl, isopropyl, butyl, tert-butyl, pentyl, hexyl, etc., or the like), an aralkyl group (for example a $C_{7-10}$ aralkyl group such as benzyl, phenethyl, etc., or the like), an aryl group (for example a $C_{6-10}$ aryl group such as phenyl, 1-naphthyl, 2-naphthyl, etc., or the like), and the like.

Examples of "(11) optionally esterified carboxyl group" include, in addition to free carboxyl group, a lower alkoxycarbonyl group, an aryloxycarbonyl group, an aralkyloxycarbonyl group and the like.

Examples of the "lower alkoxycarbonyl group" include a $C_{1-6}$ alkoxycarbonyl group such as methoxycarbonyl, ethoxycarbonyl, propoxycarbonyl, isopropoxycarbonyl, butoxycarbonyl, isobutoxycarbonyl, sec-butoxycarbonyl, tert-butoxycarbonyl, pentyloxycarbonyl, isopentyloxycarbonyl, neopentyloxycarbonyl, etc., and the like.

Examples of the "aryloxycarbonyl group" include a $C_{7-2}$ aryloxy-carbonyl group such as phenoxycarbonyl, 1-naphthoxycarbonyl, 2-naphthoxycarbonyl, etc., and the like.

Examples of the "aralkyloxycarbonyl group" include a $C_{7-10}$ aralkyloxy-carbonyl group such as benzyloxycarbonyl, phenethyloxycarbonyl, etc., and the like.

Examples of "(12) optionally substituted carbamoyl group" include, in addition to an unsubstituted carbamoyl, an N-monosubstituted carbamoyl group and an N,N-disubstituted carbamoyl group.

"N-monosubstituted carbamoyl group" means a carbamoyl group having one substituent on nitrogen atom, and examples of the substituent include a lower alkyl group (for example a $C_{1-6}$ alkyl group such as-methyl, ethyl, propyl, isopropyl, butyl, isobutyl, tert-butyl, pentyl, hexyl, etc.) and the like.

"N,N-Disubstituted carbamoyl group" means a carbamoyl group having two substituents on nitrogen atom, and examples of one substituent include the same substituents as those on "N-monosubstituted carbamoyl group" described above, and examples of the other include a lower alkyl group (for example a $C_{1-6}$ alkyl group such as methyl, ethyl, propyl, isopropyl, butyl, tert-butyl, pentyl, hexyl, etc., or the like), a $C_{3-6}$ cycloalkyl group (for example, cyclopropyl, cyclobutyl, cyclopentyl, cyclohexyl, etc.), a $C_{7-10}$ aralkyl group (for example, benzyl, phenethyl, etc., preferably a phenyl-$C_{1-4}$ alkyl, etc.) and the like. It is also possible that two substituents are taken together with nitrogen atom to form a cyclic amino group, an in such case, examples of the cyclic aminocarbamoyl group include a 3- to 8-membered (preferably 5- to 6-membered) cyclic amino-carboyl group such as 1-azetidinylcarbonyl, 1-pyrrolidinylcarbonyl, piperidinocarbonyl, morpholinocarbonyl, 1-piperazinylcarbonyl as well as 1-piperazinylcarbonyl which may have in its 4-position a lower alkyl group (for example a $C_{1-6}$ alkyl group such as methyl, ethyl, propyl, isopropyl, butyl, tert-butyl, pentyl, hexyl, etc., or the like), an aralkyl group (for example a $C_{7-10}$ aralkyl group such as benzyl, phenethyl, etc., or the like), an aryl group (for example a $C_{6-10}$ aryl group such as phenyl, 1-naphthyl, 2-naphthyl, etc., or the like), and the like.

Examples of the substituent on "(13) thiocarbamoyl nil group" as the substituent on "heterocyclic group" include the same substituent as that on "(12) carbamoyl group" described above.

Examples of "(17) acyl group" as the substituent on "heterocyclic group" include the same acyl group that used herein.

The "heterocyclic group" may have 1 to 4, preferably 1 to 2 substituents described above in any substitutable positions on its ring, and when two or more substituents exist then they may be the same or different.

Examples of "(2) optionally substituted amino group" as the substituent on "heterocyclic group" include the same group as that defined by the term "optionally substituted amino group" used herein.

The term "optionally substituted amino group" used herein include, for example, an amino group which may have one or two substituents, an optionally substituted cyclic amino group, etc.

Specific examples of the "amino group which may have one or two substituents" include a mono-lower alkylamino (for example, a mono-$C_{1-6}$ alkylamino such as methylamino, ethylamino, propylamino, isopropylamino, butylamino, etc.), a di-lower alkylamino (for example, a di-$C_{1-6}$ alkylamino such as dimethylamino, diethylamino ethylmethylamino dipropylamino, diisopropylamino, dibutylamino, etc.), and the like.

Examples of "cyclic amino group" in the "optionally substituted cyclic amino group" include a 3- to 6-membered cyclic amino group which may contain 1 to 3 heteroatoms selected from oxygen, sulfur and nitrogen atoms in addition to carbon atoms and one nitrogen atom (for example, a 3- to 6-membered cyclic amino group such as aziridinyl, azetidinyl, pyrrolidinyl, pyrrolinyl, pyrrolyl, imidazolyl, pyrazolyl, imidazolidinyl, piperidino, morpholino, thiomorpholino, dihydropyridyl, pyridyl, N-methylpiperazinyl, N-ethylpiperazinyl, etc.) and the like.

Examples of the substituent on the "amino group" include an optionally substituted hydrocarbon group, etc. The "optionally substituted hydrocarbon group" mentioned herein may be the same group as the "optionally substituted hydrocarbon group" described above. When there are two substituents, they may be the same or different.

Examples of the substituent of the "cyclic amino group" include an optionally substituted hydrocarbon group, etc. The "optionally subsituted hydrocarbon group" mentioned herein may be the same group as the "optionally substituted hydrocarbon group" described above. The "cyclic amino group" may have 1 to 5, preferably 1 to 3 substituents described above in any substitutable positions on the cyclic amino group, and when two or more substituents exist, they may be the same or different.

The term "acyl group" used herein may include, for example, an acyl derivatized from a carboxylic acid or a sulfonic acid, and the like.

Specific examples thereof include formyl, a lower alkylcarbonyl (for example, a $C_{1-6}$ alkylcarbonyl such as acetyl, propionyl, butyryl, isobutyryl, etc., or the like), an arylcarbonyl (for example, a $C_{6-10}$ arylcarbonyl such as benzoyl, naphthoyl, etc., or the like), an aralkylcarbonyl (for example, a $C_{6-10}$ aryl-$C_{1-6}$ alkyl-carbonyl such as benzylcarbonyl, phenethyl carbonyl, naphthylmethylcarbonyl, etc., or the like), a lower alkoxycarbonyl (for example, a $C_{1-6}$ alkoxy-carbonyl such as methoxycarbonyl, ethoxycarbonyl, propoxycarbonyl, isopropoxycarbonyl, butoxycarbonyl, isobutoxycarbonyl, tert-butoxycarbonyl, etc., or the like), an aralkyloxycarbonyl (for example, a $C_{6-10}$ aryl-$C_{1-6}$ alkoxy-carbonyl such as benzyloxycarbonyl, etc., or the like), a lower alkylsulfonyl (for example, a $C_{1-6}$ alkylsulfonyl such as methylsulfonyl, ethylsulfonyl, propylsulfonyl, etc.), a $C_{6-10}$ arylsulfonyl which may be substituted with a lower ($C_{1-6}$) alkyl (for example, phenylsulfonyl, naphthylsulfonyl, tosyl, etc.), an aralkylsulfonyl (for example, a $C_{6-10}$ aryl-$C_{1-6}$ alkylsulfonyl such as benzylsulfonyl, phenethylsulfonyl, naphthylmethylsulfonyl, etc., or the like) and the like. Any of these substituents may have further 1 to 3 halogen atoms (for example, fluorine, chlorine, bromine, iodine, etc.).

In the above formula, Ring A is a non-aromatic 5- to 7-membered nitrogen containing heterocyclic ring which may be further substituted.

Examples of the "non-aromatic 5- to 7-membered nitrogen-containing heterocyclic group" represented by Ring A include a non-aromatic 5- to 7-membered (preferably 5- or 6-membered) nitrogen-containing heterocyclic ring containing at least one nitrogen atom in addition to carbon atoms, and the like. Specific examples thereof include 2,3-dihydro-1H-pyrrole, 1,2-dihydropyridine, 1,2,3,4-tetrahydropyridine, 2,3,4,5-tetrahydro-1H-azepine, 2,3-dihydro-1H-azepine and the like.

Examples of the substituent which may be further possessed by the "non-aromatic 5- to 7-membered nitrogen-containing heterocyclic ring" include an optionally substituted hydrocarbon group, an optionally halogenated lower alkoxy group, an optionally halogenated lower alkylthio group, a halogen atom (for example, fluorine, chlorine, bromine, iodine, etc.), an aryloxy group (for example, a $C_{6-10}$ aryloxy such as phenoxy, etc., or the like), a lower alkanoyl (for example, a $C_{1-6}$ alkyl-carbonyl such as acetyl, propionyl, butyryl, isobutyryl, etc., or the like), an arylcarbonyl group (for example, a $C_{6-10}$ aryl-carbonyl such as benzoyl, naphthoyl, etc.), a lower alkanoyloxy group (for example, a $C_{1-6}$ alkyl-carbonyloxy such as acetyloxy, propionyloxy, butyryloxy, isobutyryloxy, etc., or the like), an arylcarbonyloxy group (for example, a $C_{6-10}$ aryl-carbonyloxy such as benzoyloxy, naphthoyloxy, etc., or the like), carboxyl group, a lower alkoxycarbonyl group (for example, a $C_{1-6}$ alkoxy-carbonyl such as methoxycarbonyl, ethoxycarbonyl, propoxycarbonyl, isopropoxycarbonyl, butoxycarbonyl, isobutoxycarbonyl, tert-butoxycarbonyl, etc., or the like), carbamoyl group, thiocarbamoyl group, a mono-lower alkylcarbamoyl group (for example, a mono-$C_{1-6}$ alkyl-carbamoyl such as methylcarbamoyl, ethylcarbamoyl, etc., or the like), a di-lower alkylcarbamoyl (for example, a di-$C_{1-6}$ alkyl-carbamoyl such as dimethylcarbamoyl, diethylcarbamoyl, etc., or the like), a $C_{6-10}$ aryl-carbamoyl (for example, phenylcarbamoyl, naphthylcarbamoyl, etc.), amidino group, imino group, amino group, a mono-lower alkylamino group (for example, a mono-$C_{1-6}$ alkylamino such as methylamino, ethylamino, propylamino, isopropylamino, butylamino, etc., or the like), a di-lower alkylamino group (for example, a di-$C_{1-6}$ alkylamino such as dimethylamino, diethylamino, ethylmethylamino, dipropylamino, diisopropylamino, dibutylamino, etc., or the like), a 3- to 6-membered cyclic amino group which may contain 1 to 3 heteroatoms selected from oxygen, sulfur and nitrogen atoms in addition to carbon atoms and one nitrogen atom (for example, a 3- to 6-membered cyclic amino group such as aziridinyl, azetidinyl, pyrrolidinyl, pyrrolinyl, pyrrolyl, imidazolyl, pyrazolyl, imidazolidinyl, piperidino, morpholino, thiomorpholino, dihydropyridyl, pyridyl, N-methylpiperazinyl, N-ethylpiperazinyl, etc., or the like), an alkylenedioxy group (for example, a $C_{1-3}$ alkylenedioxy group such as methylenedioxy, ethylenedioxy, etc., or the like), hydroxy group, nitro group, cyano group, mercapto group, sulfo group, sulfino group, phosphono group, sulfamoyl group, a mono-lower alkylsulfamoyl group (for example, a mono-$C_{1-6}$ alkylsulfamoyl group such as methylsulfamoyl, ethylsulfamoyl, propylsulfamoyl, isopropylsulfamoyl, butylsulfamoyl, etc., or the like), a di-lower alkylsulfamoyl group (for example, a di-$C_{1-6}$ alkylsulfamoyl such as dimethylsulfamoyl, diethylsulfamoyl, dipropylsulfamoyl, dibutylsulfamoyl, etc., or the like), an arylthio group (for example, a $C_{6-10}$ arylthio such as phenylthio, naphthylthio, etc., or the like), a lower alkylsulfinyl group (for example, a $C_{1-6}$ alkylsulfinyl such as methylsulfinyl, ethylsulfinyl, propylsulfinyl, butylsulfinyl, etc., or the like), an arylsulfinyl (for example, a $C_{6-10}$ arylsulfinyl such as phenylsulfinyl, naphthylsulfinyl, etc., or the like), a lower alkylsulfonyl group (for example, a $C_{1-6}$ alkylsulfonyl such as methylsulfonyl, ethylsulfonyl, propylsulfonyl, butylsulfonyl, etc., or the like), an arylsulfonyl group (for example, a $C_{6-10}$ arylsulfonyl such as phenylsulfonyl, naphthylsulfonyl, etc., or the like) and the like. When the substituent is an alkylenedioxy group, it preferably forms a ring together with two adjacent carbon atoms.

The "non-aromatic 5- to 7-membered nitrogen-containing heterocyclic ring" represented by Ring A may have 1 to 4, preferably 1 to 2 substituents described above in any substitutable positions on its ring, and when two or more substituents exist, they may be the same or different.

Ring A is preferably a non-aromatic 5- to 7-membered nitrogen-containing heterocyclic ring which may be further substituted for example by an optionally substituted hydrocarbon group (preferably an optionally substituted lower ($C_{1-6}$) alkyl group), more preferably a non-aromatic 5- to 7-membered nitrogen-containing heterocyclic ring which may be further substituted by a lower alkyl group (preferably a $C_{1-6}$ alkyl group such as methyl, etc., or the like), particularly, a non-aromatic 5-membered nitrogen-containing heterocyclic ring.

In the above formula, Ring B is benzene ring which is further substituted.

Examples of the substituent which may be possessed by "benzene ring" include a halogen atom (for example, fluorine, chlorine, bromine, iodine, etc.), hydroxy group, amino group or a hydrocarbon group which may be bonded directly or via oxygen atom, nitrogen atom or sulfur atom and which may be substituted.

Examples of the "hydrocarbon group which may be bonded directly or via oxygen atom, nitrogen atom or sulfur atom and which may be substituted" as the substituent on "benzene ring" include an optionally substituted hydrocarbon group, an optionally substituted alkoxy group, an optionally substituted aryloxy group, a substituted amino group, an optionally substituted alkylthio group, an optionally substituted arylthio group and the like.

Examples of the "optionally substituted hydrocarbon group" as the substituent on "benzene ring" include the same group as the "optionally substituted hydrocarbon group" described above.

The "alkoxy group" in the "optionally substituted hydrocarbon group" as the substituent on "benzene ring" include a lower ($C_{1-6}$) alkoxy group such as methoxy, ethoxy, propoxy, isopropoxy, butoxy, isobutoxy, sec-butoxy, tert-butoxy, etc., and the like. Examples of the substituent which may be possessed by "alkoxy group" include the same group as the "substituent" in "optionally substituted hydrocarbon group" described above. The "alkoxy group" may have 1 to 5, preferably 1 to 3 substituents described above in any substitutable positions, and when two or more substituents exist, they may be the same or different.

Examples of the "aryloxy group" in "optionally substituted aryloxy group" as the substituent on "benzene ring" include a $C_{6-10}$ aryloxy such as phenoxy, etc., and the like. Examples of the substituent which may be possessed by "aryloxy group" include the same grop as the "substituent" on "optionally substituted hydrocarbon group" described above. The "aryloxy group" may have 1 to 5, preferably 1 to 3 substituents described above in any substitutable positions, and when two or more substituents exist, they may be the same or different.

Examples of the "substituted amino group" as the substituent on "benzene ring" include amino group having 1 to 2 substituents, an optionally substituted cyclic amino group, etc. Examples of the "amino group having 1 to 2 substituents" and "optionally substituted cyclic amino group" include the same group as "amino group having 1 to 2 substituents" and "optionally substituted cyclic amino group" in "(2) optionally substituted amino group" as the substituent on "optionally substituted heterocyclic group" described above.

Examples of the "alkylthio group" in "optionally substituted alkylthio group" as the substituent on "benzene ring" include a $C_{1-6}$ alkylthio such as methylthio, ethylthio, propylthio, isopropylthio, butylthio, sec-butylthio, tert-butylthio, etc., and the like. Examples of the substituent which may be possessed by "alkylthio group" include the same group as the "substituent" on "optionally substituted hydrocarbon group" described above. The "alkylthio group" may have 1 to 5, preferably 1 to 3 substituents described above in any substitutable positions, and when two or more substituents exist, they may be the same or different.

Examples of the "arylthio group" in "optionally substituted alkylthio group" as the substituent on "benzene ring" include a $C_{6-10}$ arylthio such as phenylthio, naphthylthio, etc., and the like. Examples of the substituent which may be possessed by "arylthio group" include the same group as the "substituent" on "optionally substituted hydrocarbon group" described above. The "arylthio group" may have 1 to 5, preferably 1 to 3 substituents described above in any substitutable positions, and when two or more substituents exist, they may be the same or different.

"Benzene ring" represented by Ring B has 1 to 2, preferably 2 substituents described above in any substitutable positions on its ring, and when two substituents exist, they may be the same or different.

Preferably, Ring B is an entirely substituted benzene ring.

Such substituents on Ring B are preferably a halogen atom or an electron donor (hydroxy group, amino group or a hydrocarbon group which may be bonded directly or via oxygen atom, nitrogen atom or sulfur atom and which may be substituted and the like) in view of the action and the efficacy (lipid peroxidation inhibitory activity).

In the above formula, Ring C is an optionally substituted dihydrofuran ring.

Examples of the substituent which may be further possessed by "dihydrofuran ring" represented by Ring C include carboxyl group, an optionally substituted hydrocarbon group, an optionally substituted amino group and the like.

While examples of the "optionally substituted hydrocarbon group" as the substituent on "dihydrofuran ring" include the same group as "optionally substituted hydrocarbon group" described above, an "optionally substituted cyclic amino group" may also be preferably used as the substituent on "hydrocarbon group".

Examples of the "optionally substituted cyclic amino group" include a group represented by the formula

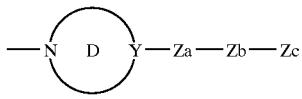

wherein Zc is hydrogen atom, an optionally substituted alkyl group or an optionally substituted aromatic group, Ring D is a 5- to 8-membered nitrogen containing heterocyclic ring which may have a substituent and which may be fused with benzene ring, Y is a carbon atom or nitrogen atom, Za is a bond, oxygen atom, sulfur atom, a group represented by the formula: $NR^9$ wherein $R^9$ is hydrogen atom, an optionally substituted hydrocarbon group or an acyl group, and Zb is a bond or a divalent aliphatic hydrocarbon group: which may be substituted and which may be bonded directly or via oxygen atom, nitrogen atom or sulfur atom.

Examples of "alkyl group" in "optionally substituted alkyl group" represented by Zc include a lower alkyl (for example a $C_{1-6}$ alkyl such as methyl, ethyl, propyl, isopropyl, butyl, isobutyl, sec-butyl, tert-butyl, pentyl, hexyl, etc., or the like). Examples of the "substituent" which may be possessed by said "alkyl group" include the same group as the "substituent" which may be possessed by "hydrocarbon group" in "optionally substituted hydrocarbon group" described above.

Examples of "aromatic group" in "optionally substituted aromatic group" represented by Zc include an aromatic hydrocarbon group, an aromatic heterocyclic group and the like.

Examples of the "aromatic hydrocarbon group" include a monocyclic or fused polycyclic aromatic hydrocarbon group having 6 to 14 carbon atoms, and the like. Specific examples thereof include a $C_{6-14}$ aryl such as phenyl, 1-naphthyl, 2-naphthyl, anthryl, etc. Among them, a $C_{6-10}$ aryl such as phenyl, 1-naphthyl, 2-naphthyl, etc. are preferred. Especially, phenyl is preferred.

Examples of the "aromatic heterocyclic group" include a 5- to 10-membered monocyclic aromatic heterocyclic group or a fused group thereof containing one or more (for example 1 to 4) heteroatoms selected from nitrogen, sulfur and oxygen atoms in addition to carbon atoms, and the like. Specific examples thereof include an aromatic heterocyclic ring such as thiophene, benzothiophene, benzofuran, benzimidazole, benzoxazole, benzothiazole, benzisothiazole, naphtho[2,3-b]thiophene, furan, pyrrole, imidazole, pyrazole, pyridine, pyrazine, pyrimidine, pyridazine, indole, isoindole, 1H-indazole, isoquinoline, quinoline, carbazole, isothiazole and isoxazole, etc., or a monovalent group formed by removing any hydrogen atom from a ring formed by condensation of any of the above rings (preferably a 5- or 6-membered monocyclic ring) with one or more (preferably 1 or 2, more preferably 1) aromatic rings (e.g., benzene ring, pyridine ring, etc.), and the like. Preferred examples of "aromatic heterocyclic group" include 2-pyridyl, 3-pyridyl, 4-pyridyl, 2-quinolyl, 3-quinolyl, 4-quinolyl, 5-quinolyl, 8-quinolyl, 1-isoquinolyl, 3-isoquinolyl, 4-isoquinolyl, 5-isoquinolyl, 1-indolyl, 2-indolyl, 3-indolyl, 2-benzothiazolyl, 2-benzothienyl, benzofuranyl, 2-thienyl, 3-thienyl, 2-benzooxazolyl, 2-benzimidazolyl, 2-pyridothiazolyl, etc. More preferably, it is 2-pyridyl, 3-pyridyl, 4-pyridyl, 2-quinolyl, 3-quinolyl, 4-quinolyl, 2-indolyl, 3-indolyl, or the like.

Examples of the "substituent" on "optionally substituted aromatic group" represented by Zc include a halogen atom (e.g., fluorine, chlorine, bromine, iodine, etc.), a $C_{1-3}$ alkylenedioxy (e.g., methylenedioxy, ethylenedioxy, etc.), nitro, cyano, an optionally halogenated $C_{1-6}$ alkyl, a $C_{3-5}$ cycloalkyl (e.g., cyclopropyl, cyclobutyl, cyclopentyl, cyclohexyl, etc.), an optionally halogenated $C_{6-14}$ alkoxy, an optionally halogenated $C_{1-6}$ alkylthio, hydroxy group, amino, a mono-$C_{1-6}$ alkylamino (e.g., methylamino, ethylamino, propylamino, isopropylamino, butylamino, etc.), a di-$C_{1-6}$ alkylamino (e.g., dimethylamino, diethylamino, ethylmethylamino, dipropylamino, dibutylamino, etc.), a $C_{1-6}$ alkyl-carbonyl (e.g., acetyl, propionyl, etc.), carboxyl, a $C_{1-6}$ alkoxy-carbonyl (e.g., methoxycarbonyl, ethoxycarbonyl, propoxycarbonyl, butoxycarbonyl, etc.), carbamoyl, a mono-$C_{1-6}$ alkyl-carbamoyl (e.g., methylcarbamoyl, ethylcarbamoyl, etc.), a di-$C_{1-6}$ alkyl-carbamoyl (e.g., dimethylcarbamoyl, diethylcarbamoyl, etc.), a $C_{1-6}$ aryl-carbamoyl (e.g., phenylcarbamoyl, naphthylcarbamoyl, etc.), sulfo, a $C_{1-6}$ alkylsulfonyl (e.g., methylsulfonyl, ethylsulfonyl, etc.), a $C_{6-10}$ aryl (e.g., phenyl, naphthyl, etc.), a $C_{6-10}$ aryloxy (e.g., phenyloxy, naphthyloxy, etc.) and the like. When the substituent is a $C_{1-3}$ alkylenedioxy, it preferably forms a ring together with two adjacent carbon atoms.

Examples of the "optionally halogenated $C_{1-6}$ alkyl" described above include a $C_{1-6}$ alkyl (e.g., methyl, ethyl, propyl, isopropyl, butyl, isobutyl, sec-butyl, tert-butyl, pentyl, hexyl, etc.) which may have 1 to 3 halogen atoms (e.g., fluorine, chlorine, bromine, iodine, etc.), and the like, including methyl, chloromethyl, difluoromethyl, trichloromethyl, trifluoromethyl, ethyl, 2-bromoethyl, 2,2,2-trifluoroethyl, propyl, 3,3,3-trifluoropropyl, isopropyl, butyl, 4,4,4-trifluorobutyl, isobutyl, sec-butyl, tert-butyl, pentyl, isopentyl, neopentyl, 5,5,5-trifluoropentyl, hexyl, 6,6,6-trifluorohexyl, and the like.

Examples of the "optionally halogenated $C_{1-6}$ alkoxy" described above include a $C_{1-6}$ alkoxy which may have 1 to 3 halogen atoms (e.g., fluorine, chlorine, bromine, iodine, etc.), and the like including methoxy, difluoromethoxy, trifluoromethoxy, ethoxy, 2,2,2-trifluoroethoxy, propoxy, isopropoxy, butoxy, 4,4,4-trifluorobutoxy, isobutoxy, sec-butoxy, pentyloxy, hexyloxy, and the like.

Examples of the "optionally halogenated $C_{1-6}$ alkylthio" described above include a $C_{1-6}$ alkylthio (e.g., methylthio, ethylthio, propylthio, isopropylthio, butylthio, sec-butylthio, tert-butylthio, etc.) which may have 1 to 3 halogen atoms (e.g., fluorine, chlorine, bromine, iodine, etc.), and the like including methylthio, difluoromethylthio, trifluoromethylthio, ethylthio, propylthio, isopropylthio, butylthio, 4,4,4-trifluorobutylthio, pentylthio, hexylthio, and the like.

The "aromatic group" in said "optionally substituted aromatic group" may have 1 to 5, preferably 1 to 3 substituents described above in any substitutable positions on its ring, and when two or more substituents exist, they may be the same or different.

Zc is preferably an optionally substituted aromatic group, more preferably an optionally substituted $C_{6-14}$ aryl (preferably phenyl), 2-pyridyl, 3-pyridyl, 4-pyridyl, 2-indolyl, 3-indolyl or benzoimidazole, especially an optionally substituted $C_{6-10}$ aryl. Said "substituent" is preferably a halogen atom, a $C_{1-6}$ alkoxy and a $C_{1-6}$ alkyl. More preferably, Zc is a $C_{6-14}$ aryl (preferably phenyl) which may have 1 to 3 substituents selected from a halogen atom, a $C_{1-6}$ alkoxy and a $C_{1-6}$ alkyl. It is also preferable that Zc is a $C_{1-6}$ alkyl which may be substituted with one or two $C_{6-14}$ aryls.

Examples of the "5- to 8-membered nitrogen-containing heterocyclic ring" in "5- to 8-membered nitrogen-containing heterocyclic ring which may be substituted and which may be fused with benzene ring" represented by Ring D include a 5- to 8-membered saturated or unsaturated heterocyclic ring containing at least one nitrogen atom in addition to carbon atoms, and the like. Specific examples thereof include piperidine, piperazine, 1,2,5,6-tetrahydropyridine, pyrrolidine, 1H-azepine, 1H-2,3-dihydroazepine, 1H-2,3,4,5-tetrahydroazepine, 1H-2,3,6,7-tetrahydroazepine, 1H-2,3,4,5,6,7-hexahydroazepine, 1H-1,4-diazepine, 1H-2,3-dihydro-1,4-diazepine, 1H-2,3,4,5-tetrahydro-1,4-diazepine, 1H-2,3,6,7-tetrahydro-1,4-diazepine, 1H-2,3,4,5,6,7-hexahydro-1,5-diazepine, 1,2-dihydroazocine, 2,3,4,5-tetrahydroazocine, 1,2,3,4,5,6-hexahydroazocine, 1,2,3,4,5,6,7,8-octahydroazocine, 1,2-dihydro-1,5-diazocine, 1,2,3,4,5,6-hexahydro-1,5-diazocine, 1,2,3,4,5,6,7,8-octahydro-1,5-diazocine, and the like. Among them, a 6-membered heterocyclic ring is preferred. Those preferred especially include piperidine, piperazine, etc.

The "substituent" which may be possessed by said "5- to 8-membered nitrogen-countering heterocyclic ring" may for example be the same substituent as that may be possessed by "optionally substituted aromatic group" represented by Zc described above, which may occur 1 to 3 times. When two or more substituents are present, they may be the same or different.

Ring D is preferably a 6-or 7-membered nitrogen-containing heterocyclic ring which may have a substituent and which may be fused with benzene ring, more preferably 1,2,4,5-tetrahydro-3H-benzazepine, piperidine or piperazine.

When Y denotes a carbon atom, for example, it may be a group represented by the formula: $>C(R^{10})$—. In this formula, Examples of $R^{10}$ include hydrogen atom, a halogen atom (e.g., fluorine, chlorine, bromine, iodine, etc.), nitro, cyano, an optionally halogenated $C_{1-6}$ alkyl, a $C_{3-6}$ cycloalkyl (e.g., cyclopropyl, cyclobutyl, cyclopentyl, cyclohexyl, etc.), an optionally halogenated $C_{1-6}$ alkoxy, an optionally halogenated $C_{1-6}$ alkylthio, hydroxy group, amino, mono-$C_{1-6}$ alkylamino (e.g., methylamino, ethylamino, propylamino, isopropylamino, butylamino, etc.), a di-$C_{1-6}$ alkylamino (e.g., dimethylamino, diethylamino, ethylmethylamino, dipropylamino, dibutylamino, etc.), a $C_{1-6}$ alkyl-carbonyl (e.g., acetyl, propionyl, etc.), carboxyl, $C_{1-6}$ alkoxy-carbonyl (e.g., methoxycarbonyl, ethoxycarbonyl, propoxycarbonyl, butoxycarbonyl, etc.), carbamoyl, a mono-$C_{1-6}$ alkyl-carbamoyl (e.g., methylcarbamoyl, ethylcarbamoyl, etc.), a di-$C_{1-6}$ alkyl-carbamoyl (e.g., dimethylcarbamoyl, diethylcarbamoyl, etc.), a $C_{6-10}$ aryl-carbamoyl (e.g., phenylcarbamoyl, naphthylcarbamoyl, etc.), sulfo, a $C_{1-6}$ alkylsulfonyl (e.g., methylsulfonyl, ethylsulfonyl, etc.), a $C_{6-10}$ aryl (e.g., phenyl, naphthyl, etc.), a $C_{6-10}$ aryloxy (e.g., phenyloxy, naphthyloxy, etc.), and the like.

$R^{10}$ is preferably hydrogen atom, cyano, a $C_{1-6}$ alkyl (for example, methyl, ethyl, propyl, isopropyl, butyl, isobutyl, pentyl, hexyl, etc.), a $C_{1-6}$ alkoxy (for example, methoxy, ethoxy, propoxy, isopropoxy, butoxy, isobutoxy, pentyloxy, hexyloxy, etc.), hydroxy group, amino, a mono-$C_{1-6}$ alkylamino, a di-$C_{1-6}$ alkylamino, a $C_{1-6}$ alkylcarbonyl, and the like.

When Y denotes nitrogen atom, Za is preferably a bond. Y is preferably CH or N. A more preferred example is CH.

Examples of the "optionally substituted hydrocarbon group" represented by $R^9$ include the same group as the "optionally substituted hydrocarbon group" described above.

Examples of the "acyl group" represented by $R^9$ include the same group as the "acyl group" described above.

$R^9$ is preferably hydrogen atom or a $C_{1-6}$ alkyl. A more preferred example is hydrogen atom.

Za is preferably a bond or a group represented by formula $NR^9$ wherein each symbol is as defined above.

Examples of the "divalent aliphatic hydrocarbon group which may be bonded directly or via oxygen atom; nitrogen atom or sulfur atom" in "divalent aliphatic hydrocarbon group which may be substituted and which may be bonded directly or via oxygen atom, nitrogen atom or sulfur atom" represented by Zb include (i) methylene or (ii) a group which is formed by removing each one hydrogen atom bound to any of two different carbon atoms in a saturated or unsaturated aliphatic hydrocarbon and which may contain 1 to 2, preferably 1 oxygen, nitrogen or sulfur atom between carbon atoms or at the terminal. Among them, a preferred one has 1 to 8 carbon atoms.

Specific examples thereof include:
(i) a $C_{1-8}$ alkylene (e.g., —CH$_2$—, —(CH$_2$)$_2$—, —(CH$_2$)$_3$—, —(CH$_2$)$_4$—, —(CH$_2$)$_3$—, —(CH)$_6$—, —(CH$_2$)$_7$—, (CH$_2$)$_8$—, etc.),
(ii) a $C_{2-8}$ alkenylene (e.g., —CH═CH—, —CH$_2$—CH═CH—, —CH$_2$—CH═CH—CH$_2$—, —CH$_2$—CH$_2$—CH═CH—, —CH═CH—CH$_2$—CH$_2$—CH$_2$—, —CH$_2$—CH$_2$—CH$_2$—CH═CH—, etc.),
(iii) a $C_{2-8}$ alkynylene (e.g., —C≡C—, —CH$_2$—C≡CH—, —CH$_2$—C≡C—CH$_2$—CH$_2$—, etc.),
(iv) a group represented by the formula: —(CH$_2$)$_p$—M—(CH$_2$)$_q$—wherein each of p and q is an integer of 1 to 8, and p+q is an integer of 1 to 8, M is O, $NR^{11}$, S, SO or SO$_2$, and the like. In the formula, $R^{11}$ is hydrogen atom, a $C_{1-6}$ alkyl (for example, methyl, ethyl, propyl, isopropyl, butyl, isobutyl, pentyl, hexyl, etc.), a $C_{3-6}$ cycloalkyl (for example, cyclopropyl, cyclobutyl, cyclopentyl, etc.), a $C_{6-14}$ aryl (for example, phenyl, 1-naphthyl, 2-naphthyl, biphenylyl, etc.), a $C_{7-11}$ aralkyl (for example, benzyl, phenethyl, etc.), or an acyl. Examples of the "acyl" include the same acyl as that described above.

M is preferably O and $NR^{11}$. One preferred especially is hydrogen atom.

Each of p and q is preferably an integer of 0 to 5. A more preferred example is an integer of 0 to 4.

Examples of the "substituent" which may be possessed by said "divalent aliphatic hydrocarbon group which may be bonded directly or via oxygen atom, nitrogen atom or sulfur atom" include a halogen atom (for example, fluorine, chlorine, bromine, iodine, etc.), nitro, cyano, an optionally halogenated $C_{1-6}$ alkyl, a $C_{3-6}$ cycloalkyl (for example, cyclopropyl, cyclobutyl, cyclopentyl, cyclohexyl, etc.), an optionally halogenated $C_{1-6}$ alkoxy, an optionally halogenated $C_{1-6}$ alkylthio, hydroxy group, amino, mono-$C_{1-6}$ alkylamino (for example, methylamino, ethylamino, propylamino, isopropylamino, butylamino, etc.), a d-$C_{1-6}$ alkylamino (for example, dimethylamino, diethylamino, ethylmethylamino, dipropylamino, dibutylamino, etc.), an optionally substituted $C_{6-14}$ aryl (for example, phenyl, 1-naphthyl, 2-naphthyl, biphenylyl, etc.), an optionally substituted $C_{7-11}$ aralkyl (for example, benzyl, phenethyl, etc.), an optionally substituted $C_{6-10}$ aryloxy (for example, phenyloxy, naphthyloxy, etc.), oxo, an acyl, and the like. Examples of the "optionally halogenated $C_{1-6}$ alkyl", "optionally halogenated $C_{1-6}$ alkoxy" and "optionally halogenated $C_{1-6}$ alkylthio" described above include the same groups as those detailed with regard to the substituent on aromatic group represented by Zc described above. Examples the "substituent" on "optionally substituted $C_{6-14}$ aryl", "optionally substituted $C_{7-11}$ aralkyl" and "optionally substituted $C_{6-10}$ aryloxy" described above include the same group as the "substituent" which may be possessed by "hydrocarbon group" in "optionally substituted hydrocarbon group" described above. The "acyl" described above may for example be the same "acyl" as that described above.

As the substituents, 1 to 5 substituents may be present at any substitutable positions, and when two or more substituents exist, they may be the same or different.

Zb is preferably a bond or a group represented by the formula: —$(CH_2)_p$—M—$(CH_2)_q$— wherein each symbol is as defined above. More preferably, it is a bond or a group represented by the formula: —$(CH_2)_p$—$NR^{11}$—$(CH_2)_q$— wherein each symbol is as defined above.

The "optionally substituted amino group" as the substituent on "dihydrofuran ring" may for example be the same group as "(2) optionally substituted amino group" as the substituent on "optionally substituted heterocyclic group" described above.

The "dihydrofuran ring" represented by Ring C may have 1 to 3 substituents described above in any substitutable positions on its ring, and when two or more substituents exist, they may be the same or different.

In the above formula, R is hydrogen atom or an acyl group.

The "acyl group" represented by R may for example be the same "acyl group" as that described above.

R is preferably hydrogen atom, formyl or a $C_{1-6}$ alkylcarbonyl or $C_{6-10}$ aryl-carbonyl optionally substituted with halogen atom(s).

As Compound (I), a compound represented by the formula:

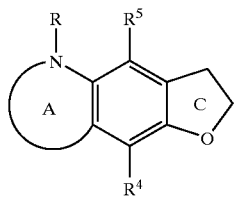

wherein $R^4$ and $R^5$ are the same or different and each denotes hydrogen atom, a halogen atom, hydroxy group, amino group or a hydrocarbon group which may be bonded directly or via oxygen atom, nitrogen atom or sulfur atom and which may be substituted, and the other symbols are as defined above, provided that both $R^4$ and $R^5$ are not hydrogen atoms at the same time, or a salt thereof is preferred.

The "halogen atom" and "hydrocarbon group which may be bonded directly or via oxygen atom, nitrogen atom or sulfur atom and which may be substituted" represented by $R^4$ and $R^5$ may be the same "halogen atom" and "hydrocarbon group which may be bonded directly or via oxygen atom, nitrogen atom or sulfur atom and which may be substituted" as substituents on Ring B described above.

It is preferable that both $R^4$ and $R^5$ are not hydrogen atoms at the same time and are the same or different, and each denotes a hydrocarbon group which may be bonded directly or via oxygen atom, nitrogen atom or sulfur atom and which may be substituted, and it is more preferable that each is a lower alkyl group (preferably, a $C_{1-6}$ alkoxy group such as methyl, ethyl, propyl, isopropyl, butyl, isobutyl, s-butyl, tert-butyl, pentyl, hexyl, etc., or the like) or a lower alkoxy group (preferably, a $C_{1-6}$ alkoxy group such as methoxy, ethoxy, propoxy, isopropoxy, butoxy, isobutoxy, sec-butoxy, tert-butoxy, etc., or the like), with a lower alkyl group (preferably a $C_{1-6}$ alkyl group such as methyl, tert-butyl, etc., or the like) being preferred especially.

As Compound (I), a compound represented by the formula:

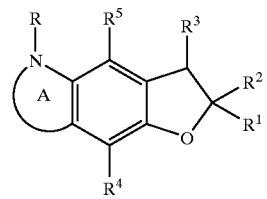

wherein $R^1$ and $R^2$ are the same or different and each denotes hydrogen atom, an optionally esterified or amidated carboxyl group or an optionally substituted hydrocarbon group, $R^3$ is hydrogen atom, an optionally substituted hydrocarbon group or an optionally substituted amino group, and the other symbols are as defined above, or a salt thereof is preferred.

The "optionally esterified or amidated carboxyl group" represented by $R^1$ and $R^2$ may for example be the same group as "(11) optionally esterified carboxyl group" and "(12) optionally substituted carbamoyl group" as substituents which may be possessed by "heterocyclic group" described above.

The "optionally substituted hydrocarbon group" represented by $R^1$ and $R^2$ may for example be the same group as the "optionally substituted hydrocarbon group" as a substituent on Ring C described above.

$R^1$ is preferably a lower alkyl group (for example, a $C_{1-6}$ alkyl group such as methyl, ethyl, propyl, isopropyl, butyl, isobutyl, s-butyl, tert-butyl, pentyl, hexyl, etc., or the like), and the like.

$R^2$ is a lower alkyl group (for example, a $C_{1-6}$ alkyl group such as methyl, ethyl, propyl, isopropyl, butyl, isobutyl, s-butyl, tert-butyl, pentyl, hexyl, etc., or the like) which may be substituted by a halogen atom, hydroxy group or an optionally substituted cyclic amino group (preferably, "optionally substituted cyclic amino group" described above, especially wherein Ring D is 1,2,4,5-tetrahydro-3H-benzazepin, piperidine or piperazine, Y is CH, Za is a bond or a group represented by the formula: $NR^9$ wherein $R^9$ is as defined above, Zb is a bond or a group represented by the formula: —$(CH_2)_p$—M—$(CH_2)_q$— wherein each symbol is as defined above and Zc is (1) a $C_{1-6}$ alkyl which may be substituted by 1 or 2 $C_{6-14}$ aryls, or (2) a $C_{6-14}$ aryl, 2-pyridyl, 3-pyridyl, 4-pyridyl, 2-indolyl, 3-indolyl or benzimidazole each of which may have 1 to 3 substituents selected from a halogen atom, a $C_{1-6}$ alkoxy and a $C_{1-6}$ alkyl), and the like.

In the above formula, $R^3$ is hydrogen atom, an optionally substituted hydrocarbon group organ optionally substituted amino group.

The "optionally substituted hydrocarbon group" and "optionally substituted amino group" represented by $R^3$ may for example be the same group as the "optionally substituted hydrocarbon group" and "optionally substituted amino group" as substituents on Ring C described above.

$R^3$ is preferably hydrogen atom or a phenyl group which may have a substituent (a $C_{1-6}$ alkyl such as methyl), with hydrogen atom being more preferred.

In the above formula, it is preferred especially that $R^1$ is a lower alkyl group (for example, a $C_{1-6}$ alkyl group such as methyl, ethyl, propyl, isopropyl, butyl, isobutyl, s-butyl, tert-butyl, pentyl, hexyl, etc., or the like), $R^2$ is a lower alkyl group (for example, a $C_{1-6}$ alkyl group such as methyl, ethyl, propyl, isopropyl, butyl, isobutyl, s-butyl, tert-butyl, pentyl, hexyl, etc., or the like) which may be substituted by a halogen atom, hydroxy group or an optionally substituted cyclic amino group (the "optionally substituted cyclic amino group" described above), $R^3$ is hydrogen atom or a phenyl group which may be substituted (substituted with a $C_{1-6}$ alkyl such as methyl, etc., or the like) each of $R^4$ and $R^5$ is a lower alkyl group (preferably a $C_{1-6}$ alkyl group such as methyl, tert-butyl, etc., or the like), and Ring A is a non-aromatic 5- to 7-membered nitrogen-containing heterocyclic ring (preferably non-aromatic 5-membered nitrogen-containing heterocyclic ring) which may be further substituted by a lower alkyl group (preferably a $C_{1-6}$ alkyl group such as methyl, etc., or the like).

In the above formula, Ring Aa is an optionally substituted non-aromatic 5- to 7-membered nitrogen-containing heterocyclic ring.

The "optionally substituted non-aromatic 5- to 7-membered nitrogen-containing heterocyclic ring" represented by Ring Aa may for example be the same group as the "optionally substituted non-aromatic 5- to 7-membered nitrogen-containing heterocyclic ring" represented by Ring A described above.

In the above formula, Ring Ba is an optionally substituted benzene ring.

The substituent which may be possessed by benzene ring represented by Ring Ba may, for example, be the same group as the subsistent possessed by benzene ring which is Ring B described above.

In the above formula, Ring Ca is an optionally substituted dihydrofuran ring.

The "optionally substituted dihydrofuran ring" represented by Ring Ca may for example be the same group as the "optionally substituted dihydrofuran ring" represented by Ring C described above.

In the above formula, Ra is hydrogen atom or an acyl group.

The "acyl group" represented by Ra may for example be the same group as the "acyl group" represented by R described above.

Rings Aa, Ba and Ca and Ra are preferably the same rings and group as those exemplified above with regard to preferred Rings A, B and C and R, respectively.

The salt of Compound (I) or Compound (I') may for example be a pharmacologically acceptable salt. For example, a salt with an inorganic base, an ammonium salt, a salt with an organic base, a salt with an inorganic acid, a salt with an organic salt and a salt with a basic or acidic amino acid may be mentioned. A preferred example of a salt with an inorganic base is an alkaline metal salt such as a sodium or potassium salt, an alkaline earth metal salt such as a calcium or magnesium salt, as well as an aluminum salt. A preferred example of a salt with an organic base is a salt with trimethylamine, triethylamine, pyridine, picoline, 2,6-lutidine, ethanolamine, diethanolamine, triethanolamine, cyclohexylamine, dicyclohexylamine and N,N'-dibenzylethylenediamine; A preferred example of a salt with an inorganic acid is a salt with hydrochloric acid, hydrobromic acid, nitric acid, sulfuric acid and phosphoric acid. A preferred example of a salt with an organic acid is a salt with formic acid, acetic acid, trifluoroacetic acid, phthalic acid, fumaric acid, oxalic acid, tartaric acid, maleic acid, citric acid, succinic acid, malic acid, methanesulfonic acid, benzenesulfonic acid and p-toluenesulfonic acid. A preferred example of a salt with a basic amino acid is a salt with arginine, lysine and ornithine, while that with an acidic amino acid is a salt with aspartic acid and glutamic acid.

Among them, a pharmaceutically acceptable salt is preferable, including a salt with an inorganic acid such as hydrochloric acid, hydrobromic acid, nitric, sulfuric acid and phosphoric acid and a salt with an organic acid such as acetic acid, phthalic acid, fumaric acid, oxalic acid, tartaric acid, maleic acid, citric acid, succinic acid, methanesulfonic acid and p-toluenesulfonic acid when a basic functional group is present in Compound (I) or (I'), as well as an alkaline metal salt such as a sodium or potassium salt, an &A alkaline earth metal salt such as a calcium or magnesium salt and an aluminum salt when an acidic functional group is present.

The process for preparing Compound (I) is described below. Compound (I) includes Compounds (Ia) and (Ib).

Compound (I') can be prepared according to the same process as that for preparing Compound (I) or an analogous one.

In the following schemes, each symbol in the compounds is as defined above. The compound in the scheme includes its salt form, which may for example be the same salt as that of Compound (I).

Compound (I) is produced by a process shown in Synthesis Method 1.

Compounds (III), (VI), (X), (XII), (XIII), (XX), (XXX) and (XXXIV) can readily be available commercially, or may be prepared by a per se known process or an analogous one.

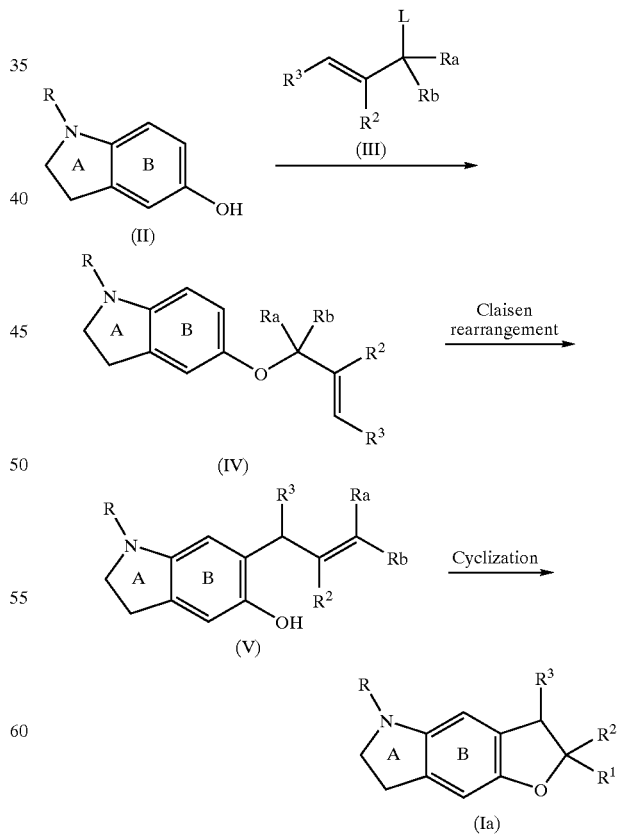

Synthesis Method 1

Compound (IV) is produced by reacting Compound (II) with Compound (III) if necessary in the presence of a base.

In the formula, each of Ra and Rb is a substituent constituting a part of R¹, and may for example be the same group as the substituent which may be possessed by "hydrocarbon group".

Examples of a "leaving group" represented by L include hydroxy group, a halogen atom (for example, fluorine, chlorine, bromine, iodine, etc.), an optionally halogenated $C_{1-5}$ alkylsulfonyloxy (for example, methanesulfonyloxy, ethanesulfonyloxy, trichloromethanesulfonyloxy, etc.), an optionally substituted $C_{6-10}$ arylsulfonyloxy and the like. Examples of the "optionally substituted $C_{6-10}$ arylsulfonyloxy" include a $C_{6-10}$ arylsulfonyloxy (e.g., phenylsulfonyloxy, naphthylsulfonyloxy, etc.) which may have 1 to 3 substituents selected from a $C_{1-6}$ alkyl (e.g., methyl, ethyl, etc.), a $C_{1-6}$ alkoxy (e.g., methoxy, ethoxy, etc.) and nitro, and specific examples thereof include benzenesulfonyloxy, m-nitrobenzenesulfonyloxy and p-toluenesulfonyloxy, etc.

The amount of Compound (III) employed per mole of Compound (II) is about 1.0 to about 5.0 moles, preferably about 1.0 to about 2.0 moles.

Said "base" may for example be an inorganic base such as sodium hydroxide, potassium hydroxide, etc., a basic salt such as sodium carbonate, potassium carbonate, cesium carbonate, sodium hydrogen carbonate, etc., an aromatic amine such as pyridine, lutidine, etc., a tertiary amine such as triethylamine, tripropylamine, tributylamine, cyclohexyldimethylamine, 4-dimethylaminopyridine, N,N-dimethylaniline, N-methylpiperidine, N-methylpyrrolidine, N-methylmorpholine, etc., an alkaline metal hydride such as sodium hydride, potassium hydride, etc., a metal amide such as sodium amide, lithium diisopropylamide, lithium hexamethyldisilazide, etc., and a metal alkoxide such as sodium methoxide, sodium ethoxide, potassium t-butoxide, etc., and the like. The amount of the base employed per mole of Compound (II) is about 1.0 to about 5.0 moles, preferably about 1.0 to about 2.0 moles.

This reaction is conducted advantageously by using a solvent which is inert to the reaction. Such solvent is not limited particularly provided that it allows the reaction to proceed, and may for example be an alcohol, an ether, an aliphatic hydrocarbon, an aromatic hydrocarbon, an amide, a halogenated hydrocarbon, a nitrile and a sulfoxide as well as a mixture thereof.

The reaction time ranges usually from about 30 minutes to about 48 hours, preferably about 1 hour to about 24 hours. The reaction temperature is usually about −20 to about 150° C., preferably about 0 to about 100° C.

Alternatively to the reaction described above, a Mitsunobu reaction (Synthesis, 1981, page 1 to 27) can also be employed.

Said reaction involves a reaction of Compound (II) with Compound (III) wherein L is OH in the presence of an azodicarboxylate (e.g., diethylazodicarboxylate, etc.) and a phosphine (e.g., triphenylphosphine, tributylphosphine, etc.).

Compound (III) wherein L is OH is employed in an amount of about 1.0 to about 5.0 moles, preferably about 1.0 to about 2.0 moles per mole of Compound (II).

Each of said "azodicarboxylate" and "phosphine" is employed in an amount of about 1.0 to about 5.0 moles, preferably about 1.0 to about 2.0 moles per mole of Compound (II).

This reaction is conducted advantageously by using a solvent which is inert to the reaction. Such solvent is not limited particularly provided that it allows the reaction to proceed, and may for example be an ether, an aliphatic hydrocarbon, an aromatic hydrocarbon, an amide, a halogenated hydrocarbon, a nitrile and a sulfoxide as well as a mixture thereof.

The reaction time ranges usually from about 5 minutes to about 48 hours, preferably about 30 minutes to about 24 hours. The reaction temperature is usually about −20 to about 200° C., preferably about 0 to about 100° C.

Compound (V) is prepared by subjecting Compound (IV) to a Claisen rearrangement.

This reaction is conducted without any solvent, or may advantageously be conducted using a solvent which is inert to the reaction. Such solvent is not limited particularly provided that it allows the reaction to proceed, and may for example be an alcohol, an aliphatic hydrocarbon, an aromatic hydrocarbon, an organic acid, an ether, an aniline and a halogenated hydrocarbon as well as a mixture thereof.

This reaction may be performed if necessary with an acid catalyst. An acid catalyst may for example be a Lewis acid such as aluminum chloride and boron tribromide. An acid catalyst is employed, for example when it is a Lewis acid, in an amount usually of about 0.1 to about 20 moles, preferably about 0.1 to about 5 moles per mole of Compound (IV). The reaction time ranges usually from about 30 minutes to about 24 hours, preferably about 1 hour to about 6 hours. The reaction temperature is usually about −70 to about 300° C., preferably about 150 to about 250° C.

While a product still in a solution or as a crude product may be used in the next reaction, it can be isolated from a reaction mixture by an ordinary method, and can readily be purified by a conventional separating procedure (e.g., recrystallization, distillation, chromatography, etc.).

Compound (Ia) can be prepared by subjecting Compound (V) to a ring closure in the presence of a protonic acid or a Lewis acid. A protonic acid may for example be a mineral acid such as hydrochloric acid, hydrobromic acid and sulfuric acid and a sulfonic acid such as trifluoromethanesulfonic acid and fluorosulfonic acid, while a Lewis acid may for example be aluminum chloride, aluminum bromide, titanium tetrachloride, tin (IV) chloride, zinc chloride, boron trichloride, boron tribromide and boron trifluoride. While each of a protonic acid and a Lewis acid is usually employed alone, they may be combined with each other if necessary. A protic acid is employed usually in an amount of about 1.0 to about 200 moles, preferably about 1.0 to about 100 moles per mole of Compound (V). A Lewis acid is employed usually in an amount of about 1.0 to about 5.0 moles, preferably about 1.0 to about 3.0 moles per mole of Compound (V). This reaction is conducted advantageously by using a solvent which is inert to the reaction. Such solvent is not limited particularly provided that it allows the reaction to proceed, and may for example be an ether, an aliphatic hydrocarbon, an aromatic hydrocarbon, an amide, a halogenated hydrocarbon, a nitrile and a sulfoxide as well as a mixture thereof. The reaction temperature is usually about −20 to about 150° C., preferably about 0 to about 100° C. The reaction time ranges usually from about 5 minutes to about 24 hours, preferably about 10 minutes to about 5 hours. While a product still in a solution or as a crude product may be used in the next reaction, it can be isolated from a reaction mixture by an ordinary method, and can readily be purified by a separating procedure such as recrystallization, distillation, chromatography or the like.

Compound (Ia) can be prepared also by reacting Compound (V) with a halogenating reagent.

The "halogenating reagent" may for example be a halogen such as bromine, chlorine, iodine, or the like, an imide such as N-bromosuccinimide, or the like, a halogen adduct such as benzyltrimethylammonium dichloroiodate, benzyltrimethylammonium tribromide, etc., or the like. The halogenating reagent is employed in an amount of about 1 to about 5 moles, preferably about 1 to about 2 moles per mole of Compound (V).

This reaction may advantageously be conducted using a solvent which is inert to the reaction. Such solvent is not limited particularly provided that it allows the reaction to proceed, and may for example be an alcohol, an aliphatic hydrocarbon, an aromatic hydrocarbon, an amide, a halogenated hydrocarbon, a nitrile, a sulfoxide, an organic acid, a nitroalkane and an aromatic amine as well as a mixture thereof.

This reaction may be performed if necessary in the presence of a base or a radical initiator, or under irradiation.

The "base" may for example be a basic salt such as sodium carbonate, potassium carbonate, cesium carbonate, sodium hydrogen carbonate, sodium acetate, potassium acetate, etc., an aromatic amine such as pyridine, lutidine, etc., a tertiary amine such as triethylamine, tripropylamine, tributylamine, cyclohexyldimethylamine, 4-dimethylaminopyridine, N,N-dimethylaniline, N-methylpiperidine, N-methylpyrrolidine, N-methylmorpholine, etc., or the like. The amount of the base employed is about 0.8 to about 10 moles per mole of Compound (V).

The "radical initiator" may for example be benzoyl peroxide and azobisisobutyronitrile. The amount of the radical initiator is about 0.01 to about 1 mole per mole of Compound (V).

When irradiation is effected, a halogen lamp may for example be employed.

The reaction temperature is usually about –50 to about 150° C., preferably about 0 to about 100° C. The reaction time ranges usually from about 5 minutes to about 24 hours, preferably about 10 minutes to about 12 hours.

While a product still in a solution or as a crude product may be used in the next reaction, it can be isolated from a reaction mixture by an ordinary method, and can readily be purified by a conventional separating procedure (e.g., recrystallization, distillation, chromatography, etc.).

Compound (Ia) can be prepared also by treating Compound (V) with an organic peracid if necessary in the presence of a base to effect a ring closure.

The organic peracid may for example be m-chloroperbenzoic acid, peracetic acid, etc. The organic peracid is employed in an amount of about 1.0 to about 5.0 moles, preferably about 1.0 to about 2.0 moles, per mole of Compound (V). This reaction may advantageously be conducted using a solvent which is inert to the reaction. Such solvent is not limited particularly provided that it allows the reaction to proceed, and may for example be water, an ether, an aliphatic hydrocarbon, an aromatic hydrocarbon, an amide, a halogenated hydrocarbon, a nitrile, a sulfoxide, an organic acid and an aromatic amine as well as a mixture thereof. The base employed if necessary may for example be a basic salt such as sodium carbonate, potassium carbonate, cesium carbonate, calcium carbonate and sodium hydrogen carbonate, an aromatic amine such as pyridine and lutidine, a tertiary amine such as triethylamine, tripropylamine, tributylamine, cyclohexyldimethylamine, 4-dimethylaminopyridine, N,N-dimethylaniline, N-methylpiperidine, N-methylpyrrolidine and N-methylmorpholine. The reaction temperature is usually about –20 to about 150° C., preferably about 0 to about 100° C. The reaction time ranges usually from about 5 minutes to about 24 hours, preferably about 10 minutes to about 5 hours. Product (Ia) can be isolated from a reaction mixture by an ordinary method, and can readily be purified by a separating procedure such as recrystallization, distillation, chromatography, etc.

Compound (I) is prepared also by a process shown in Synthesis Method 2.

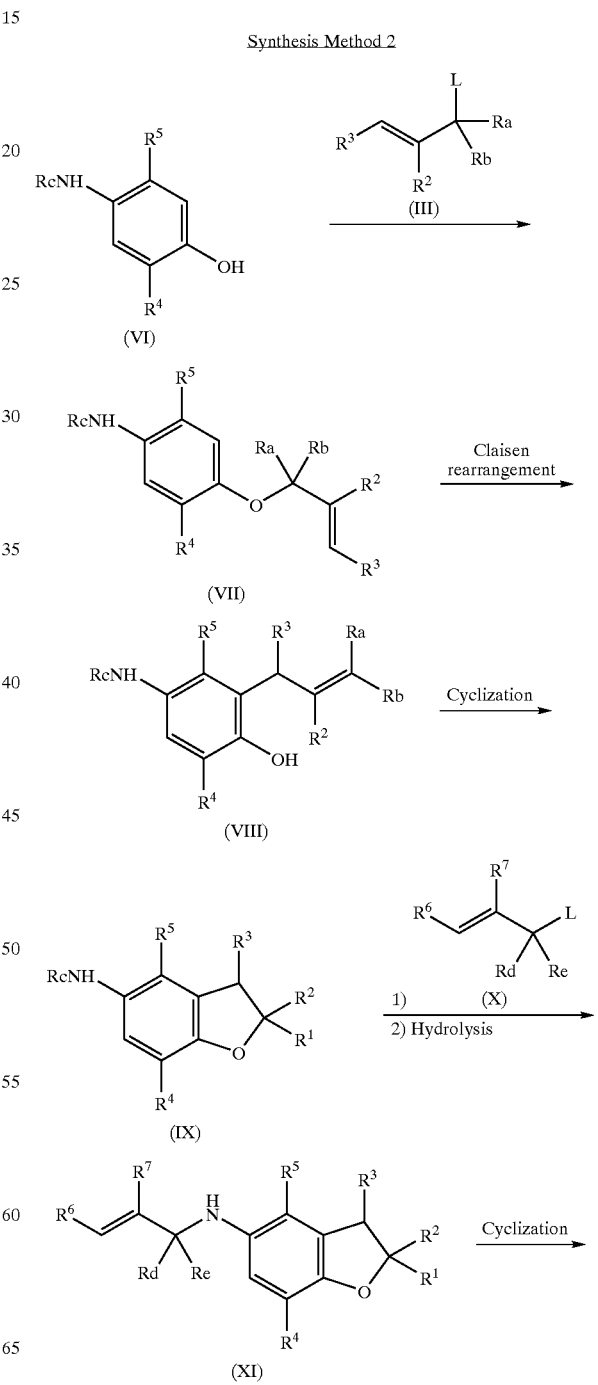

Synthesis Method 2

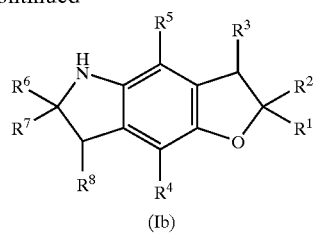

(Ib)

A process from Compound (VI) through Compound (IX) is conducted in accordance with a method for producing Compound (Ia) from Compound (II) in Scheme 1.

Rc denotes an acyl group, which may for example be the same group as the "acyl group" described above.

In the formula, each of Rd and Re is a substituent constituting a part of R6, and may for example be the same group as the substituent which may be possessed by "hydrocarbon group".

Compound (XI) is prepared by reacting Compound (IX) with Compound (X) if necessary in the presence of a base.

The amount of Compound (X) employed per mole of Compound (IX) is about 1.0 to about 5.0 moles, preferably about 1.0 to about 2.0 moles.

Said "base" may for example be an inorganic base such as sodium hydroxide, potassium hydroxide, etc., a basic salt such as sodium carbonate, potassium carbonate, cesium carbonate, sodium hydrogen carbonate, etc., an aromatic amine such as pyridine, lutidine, etc., a tertiary amine such as triethylamine, tripropylamine, tributylamine, cyclohexyldimethylamine, 4-dimethylaminopyridine, N,N-dimethylaniline, N-methylpiperidine, N-methylpyrrolidine, N-methylmorpholine, etc., an alkaline metal hydride such as sodium hydride, potassium hydride, etc., a metal amide such as sodium amide, lithium diisopropylamide and lithium hexamethyldisilazide, etc., a metal alkoxide such as sodium methoxide, sodium ethoxide, potassium t-butoxide, etc., and the like. The amount of a base employed per mole of Compound (IX) is about 1.0 to about 5.0 moles, preferably about 1.0 to about 2.0 moles.

This reaction is conducted advantageously by using a solvent which is inert to the reaction. Such solvent is not limited particularly provided that it allows the reaction to proceed, and may for example be an alcohol, an ether, an aliphatic hydrocarbon, an aromatic hydrocarbon, an amide, a halogenated hydrocarbon, a nitrile and a sulfoxide as well as a mixture thereof.

The reaction time ranges usually from about 30 minutes to about 48 hours, preferably about 1 hour to about 24 hours. The reaction temperature is usually about -20 to about 150° C., preferably about 0 to about 100° C.

Alternatively to the reaction described above, a Mitsunobu reaction (Synthesis, 1981, page 1 to 27) can also be employed.

Said reaction involves a reaction of Compound (IX) with Compound (X) wherein L is OH in the presence of an azodicarboxylate (e.g., diethylazodicarboxylate, etc.) and a phosphine (e.g., triphenylphosphine, tributylphosphine, etc.).

Compound (X) wherein L is OH is employed in an amount of about 1.0 to about 5.0 moles, preferably about 1.0 to about 2.0 moles, per mole of Compound (IX).

Each of said "azodicarboxylate" and "phosphine" is employed in an amount of about 1.0 to about 5.0 moles, preferably about 1.0 to about 2.0 moles, per mole of Compound (IX).

This reaction is conducted advantageously by using a solvent which is inert to the reaction. Such solvent is not limited particularly provided that it allows the reaction to proceed, and may for example be an ether, an aliphatic hydrocarbon, an aromatic hydrocarbon, an amide, a halogenated hydrocarbon, a nitrile and a sulfoxide as well as a mixture thereof.

The reaction time ranges usually from about 5 minutes to about 48 hours, preferably about 30 minutes to about 24 hours. The reaction temperature is usually about -20 to about 200° C., preferably about 0 to about 100° C.

Compound (Ib) is prepared by subjecting Compound (XI) to a Claisen rearrangement in the presence of an acid catalyst, followed by ring-closing reaction.

The acid catalyst may for example be a Lewis acid, such as zinc chloride, aluminum chloride, tin chloride, etc. The amount of the acid catalyst employed is usually about 0.1 to about 20 moles, preferably about 1 to about 5 moles per mole of Compound (XI).

This reaction is conducted without any solvent, or may advantageously be conducted using a solvent which is inert to the reaction. Such solvent is not limited particularly provided that it allows the reactiinto be proceeded, and may for example be an alcohol, an aliphatic hydrocarbon, an aromatic hydrocarbon, an organic acid, an ether, an aniline and a halogenated hydrocarbon as well as a mixture thereof.

The reaction time ranges usually from about 30 minutes to about 24 hours, preferably about 1 hour to about 6 hours. The reaction temperature is usually about -70 to about 300° C., preferably about 150 to about 250° C.

While a product still in a solution or as a crude product may be used in the next reaction, it can be isolated from a reaction mixture by an ordinary method, and can readily be purified by a conventional separating procedure (e.g., recrystallization, distillation, chromatography).

A 2,3-dihydro-5-hydroxyindole derivative employed in Synthesis Method 1 is produced by a process shown in Synthesis Methods 3-1, 3-2 and 3-3.

A production by Synthesis Method 3-1 is described below.

Synthesis Method 3-1

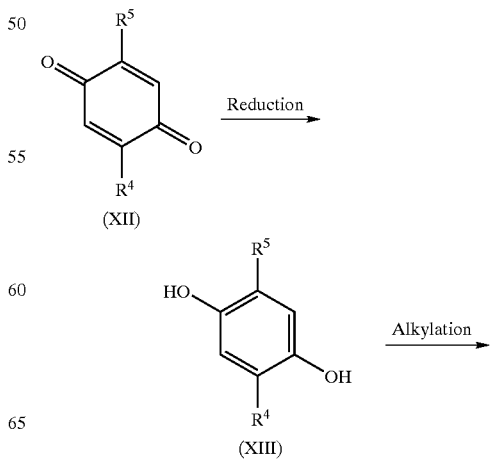

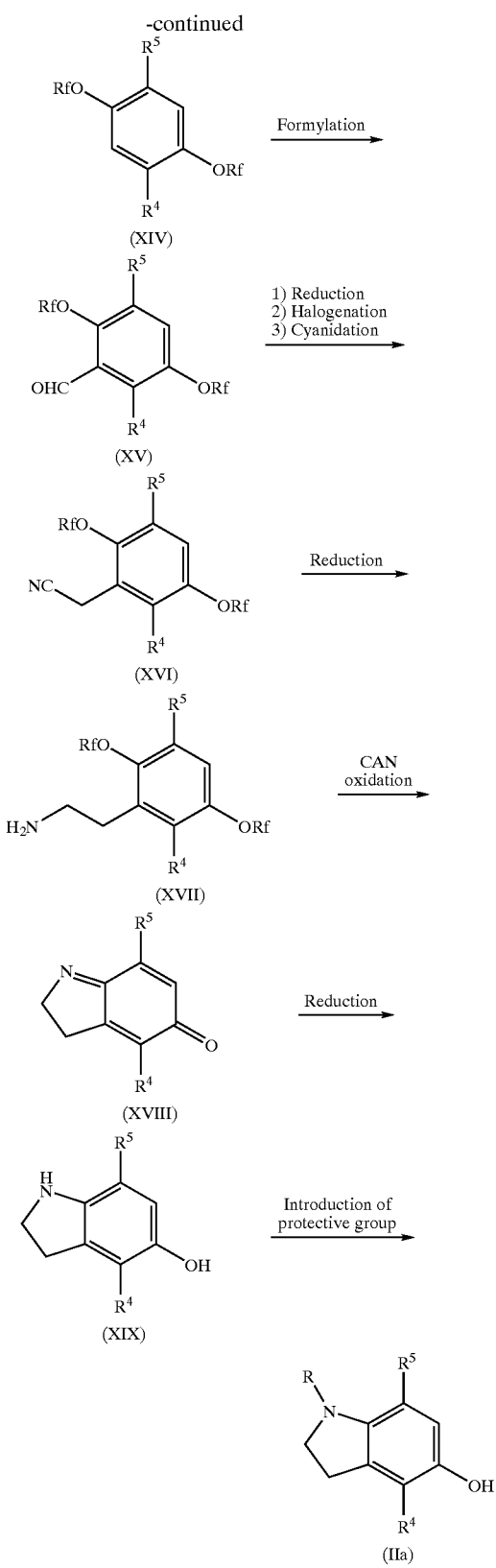

CAN: Cerium diammonium nitrate

Compound (XIII) is prepared by reducing Compound (XII). A reducing agent may for example be sodium hydrosulfite and tin (II) chloride. The amount of a reducing agent per mole of Compound (XII) is, for example, about 1.0 to about 30 moles, preferably about 2.0 to about 5.0 moles when sodium hydrosulfite is employed, while it is about 1.0 to about 10 moles, preferably about 2.0 to about 5.0 moles when tin (II) chloride is employed. When tin (II) chloride is employed as a reducing agent, it is reacted under an acidic condition usually in the presence of a mineral acid such as hydrochloric acid. This reaction is conducted advantageously by using a solvent which is inert to the reaction. Such solvent is not limited particularly provided that it allows the reaction to proceed, and may for example be water, or a mixture of water with an alcohol, an ether, an aliphatic hydrocarbon, an aromatic hydrocarbon and an amide. The reaction time ranges usually from about 10 minutes to about 10 hours, preferably about 10 minutes to about 2 hours. The reaction temperature is usually about 0 to about 100° C., preferably about 5 to about 80° C. While a product still in a solution or as a crude product may be used in the next reaction, it can be isolated from a reaction mixture by an ordinary method, and can readily be purified by a separating procedure such as recrystallization, distillation, chromatography, or the like.

Alternatively, Compound (XIII) can be prepared by reducing Compound. (XII) using hydrogen in the presence of a hydrogenating catalyst such as platinum oxide, palladium on carbon, Raney nickel, Raney cobalt and the like. The amount of a hydrogenating catalyst is about 0.1 to about 1000% by weight, preferably about 1 to about 300% by weight based on Compound (XII).

This reaction is conducted advantageously by using a solvent which is inert to the reaction. Such solvent is not limited particularly provided that it allows the reactiinto be proceeded, and may for example be an alcohol, an ether, an aliphatic hydrocarbon, an aromatic hydrocarbon, an amide, an organic acid such as formic acid and acetic acid, as well as a mixture thereof. While the reaction time may vary depending on the activity and the amount of the catalyst employed, it is usually about 10 minutes to about 100 hours, preferably about 10 minutes to about 10 hours. The reaction temperature is usually about 0 to about 120° C., preferably about 20 to about 80° C. When a hydrogenating catalyst is employed, the pressure of hydrogen is usually about 1 to about 100 atm. While a product still in a solution or as a crude product may be used in the next reaction, it can be isolated from a reaction mixture by an ordinary method, and can readily be purified by a separating procedure such as recrystallization, distillation, chromatography, or the like.

Compound (XIV) is prepared by alkylating Compound (XIII). In this reaction, Compound (XIII) and a corresponding alkylating agent (for example, corresponding alkyl halide, alcohol sulfonate, etc.) are reacted if necessary in the presence of a base. The amount of the alkylating agent is employed about 1.0 to about 5.0 moles, preferably about 1.0 to about 2.0 per mole of Compound (XIII). The base may for example be an inorganic base such as sodium carbonate, potassium carbonate, cesium carbonate, sodium hydrogen carbonate, etc., an aromatic amine such as pyridine, lutidine, etc., a tertiary amine such as triethylamine, tripropylamine, tributylamine, cyclohexyldimethylamine, 4-dimethylaminopyridine, N,N-dimethylaniline, N-methylpiperidine, N-methylpyrrolidine, N-methylmorpholine, etc., an alkaline metal hydride such as sodium hydride and potassium hydride, a metal amide such as sodium amide, lithium diisopropylamide, lithium hexamethyldisilazide, etc., a metal alkoxide such as sodium methoxide, sodium ethoxide, potassium t-butoxide, etc., or the like. The amount of the base employed per mole of Compound (XIII) is about 2.0 to about 10.0 moles, preferably about 2.0 to about 5.0 moles. This reaction is conducted advantageously by using a solvent which is inert to the reaction. Such solvent is not limited particularly provided that it allows the reactiinto be proceeded, and may for example be an alcohol, an ether, an aliphatic hydrocarbon, an aromatic hydrocarbon, an amide, a halogenated hydrocarbon, a nitrile and a sulfoxide as well as a mixture thereof. The reaction time ranges usually from about 30 minutes to about 48 hours, preferably about 1 hour to about 24 hours. The reaction temperature is usually about −20 to about 200° C., preferably about 0 to about 150° C.

Compound (XV) is prepared by formylating Compound (XIV). In this reaction, Compound (XIV) is subjected to a reaction with a dichloromethyl alkylether in the presence of an acid catalyst followed by a hydrolysis, whereby obtaining a formyl form. The dichloromethyl alkyl ether may for example be dichloromethyl methyl ether and dichloromethyl butyl ether. The dichloromethyl alkyl ether is employed in an amount of about 1.0 to 10.0 moles, preferably about 1.0 to 5.0 moles per mole of Compound (XIV). The acid catalyst may for example be titanium (IV) chloride, aluminum chloride and tin (IV) chloride. The acid catalyst is employed usually in an amount of about 1.0 to about 10.0 moles, preferably about 1.0 to 5.0 moles per mole of Compound (XIV). This reaction is conducted advantageously by using a solvent which is inert to the reaction. Such solvent is not limited particularly provided that it allows the reactiinto be proceeded, and may for example be an ether, an aliphatic hydrocarbon, an aromatic hydrocarbon, a halogenated hydrocarbon and a nitrile as well as a mixture thereof. The reaction time ranges usually from 10 minutes to 48 hours, preferably 30 minutes to 24 hours. The reaction temperature is usually −20 to 100° C., preferably 0 to 80° C. The subsequent hydrolysis is conducted by mixing the reaction mixture with water. The formylation can be conducted also under a Vilsmeier reaction condition. In this method, a formamide is reacted in the presence of an acid catalyst and then hydrolyzed with a base to obtain a formyl form. The formamide may for example be methylformamide, ethylformamide, or the like. The formamide is employed in an amount of about 1.0 to 10.0 moles, preferably about 1.0 to 5.0 moles per mole of Compound (XIV). The acid catalyst may for example be phosphoryl chloride, thionyl chloride, or the like. The acid catalyst is employed usually in an amount of about 1.0 to 10.0 moles, preferably about 1.0 to 5.0 moles per-mole of Compound (XIV). This reaction is conducted advantageously by using a solvent which is inert to the reaction. Such solvent is not limited particularly provided that it allows the reactiinto be proceeded, and may for example be an amide, an ether, an aliphatic hydrocarbon, an aromatic hydrocarbon, a halogenated hydrocarbon and a nitrile as well as a mixture thereof. The reaction time ranges usually from 10 minutes to 48 hours, preferably 30 minutes to 24 hours. The reaction temperature is usually −20 to 100° C., preferably 0 to 80° C. The subsequent hydrolysis is conducted by mixing the reaction mixture with base. Such base may for example be an inorganic base such as sodium hydroxide and potassium hydroxide, as well as a basic salt such as sodium carbonate, potassium carbonate, cesium carbonate, sodium hydrogen carbonate, etc. While a product still in a solution or as a crude product may be used in the next reaction, it can be isolated from a reaction mixture by an ordinary method, and can readily be purified by a separating procedure such as recrystallization, distillation, chromatography, etc.

Compound (XVI) is prepared by a reduction of Compound (XV), followed by a halogenation of the resultant alcohol form, subsequently to a substitution with cyano group. The reducing agent employed in this reduction may for example be a metal hydride such as aluminum hydride, diisobutylaluminum hydride, etc., a metal hydrogen complex such as lithium aluminum hydride, sodium borohydride, etc., a borane complex such as borane tetrahydrofuran complex, borane dimethyl sulfide complex, etc., an alkyl borane such as thexylborane, disiamylborane, etc., diborane, as well as a metal such as zinc, aluminum, tin and iron, an alkaline metal such as sodium and lithium in combination with a liquid ammonia (Birch reduction), or the like. As a hydrogenating catalyst, there may for example be employed palladium on carbon, platinum oxide, Raney nickel, Raney cobalt and the like. The amount of the reducing agent is about 1.0 to about 10 moles, preferably about 1.0 to about 3.0 mole per mole of Compound (XV) when the metal hydride is employed; about 1.0 to about 10 moles, preferably about 1.0 to about 3.0 moles per mole of Compound (XV) when the metal hydrogen complex is employed; about 1.0 to about 5.0 moles per mole of Compound (XV) when the borane complex, the alkyl borane or diborane is employed; about 1.0 to about 20 equivalents, preferably about 1 to about 5 equivalents when the metal is employed; and about 1 to about 20 equivalents, preferably about 1 to about 5 equivalents when the alkaline metal is employed; and, in the case of hydrogenation, the amount of the catalyst such as palladium on carbon, platinum oxide, Raney nickel, Raney cobalt, etc. is employed in an amount of about 5 to about 1000% by weight, preferably about 10 to about 300% by weight based on Compound (XV). This reaction is conducted advantageously by using a solvent which is inert to the reaction. Such solvent is not limited particularly provided that it allows the reactiinto be proceeded, and may for example be an alcohol, an ether, an aliphatic hydrocarbon, an aromatic hydrocarbon, an amide, an organic acid, as well as a mixture thereof. While the reaction time may vary depending on the type and the amount of the reducing agent employed as well as the activity and the amount of the catalyst employed, it is usually about 1 hour to about 100 hours, preferably about 1 hour to about 50 hours. The reaction temperature is usually about 0 to about 120° C., preferably about 20 to about 80° C. When the hydrogenating catalyst is employed, the pressure of hydrogen is usually about 1 to about 100 atm. While a product still in a solution or as a crude product may be used in the next reaction, it can be isolated from a reaction mixture by an ordinary method, and can readily be purified by a separating procedure such as recrystallization, distillation, chromatography, etc.

The halogenating agent employed in the subsequent halogenation step may for example be a thionyl halide such as thionyl chloride, thionyl bromide, etc., a phosphoryl halide such as phosphoryl chloride, phosphoryl bromide, etc., a phosphorus halide such as phosphorus pentachloride, phosphorus trichloride, phosphorus pentabromide, phosphorus tribromide, etc., an oxalyl halide such as oxalyl chloride, etc. as well as phosgene or the like. The halogenating agent is employed in an amount of about 1.0 to about 30 moles, preferably about 1.0 to about 10 moles per mole of the alcohol form. This reaction is conducted without any solvent, or may advantageously be conducted using a solvent which is inert to the reaction. Such solvent is not limited particularly provided that it allows the reactiinto be proceeded, and may for example be an aliphatic hydrocarbon, an aromatic hydrocarbon, an ether, an amide, and a halogenated hydrocarbon as well as a mixture thereof. The reaction time ranges usually from about 10 minutes to about 12 hours, preferably about 10 minutes to about 5 hours. The reaction temperature is usually about −10 to about 200° C., preferably about −10 to about 120° C. While a product still in a solution or as a crude product may be used in the next reaction, it can be isolated from a reaction mixture by an ordinary method, and can readily be purified by a separating procedure such as recrystallization, distillation, chromatography, etc.

The cyaniding agent in the following cyanidaton step may for example be an inorganic cyanide such as sodium cyanide, potassium cyanite, etc. The inorganic cyanide is employed in an amount of about 0.8 to about 10 moles, preferably about 1.0 mole to about 5 moles per mole of the halide. This reaction is conducted advantageously by using a solvent which is inert to the reaction. Such solvent is not limited particularly provided that it allows the reactiinto be proceeded, and may for example be an ether, an aliphatic hydrocarbon, an aromatic hydrocarbon, an amide, a halogenated hydrocarbon, a nitrile and a sulfoxide as well as a mixture thereof. The reaction temperature is usually about −20 to about 150° C., preferably about 0 to about 100° C. The reaction time ranges usually from about 5 minutes to about 24 hours, preferably about 10 minutes to about 5 hours. While a product still in a solution or as a crude product may be used in the next reaction, it can be isolated from a reaction mixture by an ordinary method, and can readily be purified by a separating procedure such as recrystallization, distillation, chromatography, etc.

Compound (XVII) is prepared by reducing Compound, (XVI). The reducing agent employed in this reduction may for example be a metal hydride such as aluminum hydride, diisobutylaluminumhydride, etc., a metal hydrogen complex such as lithium aluminum hydride, sodium borohydride, etc., a borane complex such as borane tetrahydrofuran complex, borane dimethyl sulfide complex, etc., an alkyl borane such as thexylborane, disiamylborane, etc., diborane, as well as a metal such as zinc, aluminum, tin, iron, etc., an alkaline metal such as sodium, lithium, etc. in combination with a liquid ammonia (Birch reduction), or the like. As a hydrogenating catalyst, there may for example be employed palladium on carbon, platinum oxide, Raney nickel, Raney cobalt and the like. The amount of the reducing agent is about 1.0 to about 10 moles, preferably about 1.0 to about 3.0 mole per mole of Compound (XVI) when the metal hydride is employed; about 1.0 to about 10 moles, preferably about 1.0 to about 3.0 moles per mole of Compound (XVI) when the metal hydrogen complex is employed; about 1.0 to about 5.0 moles per mole of Compound (XVI) when the borane complex, the alkyl borane or diborane is employed; about 1.0 to about 20 equivalents, preferably about 1 to about 5 equivalents when the metal is employed; and about 1 to about 20 equivalents, preferably about 1 to about 5 equivalents when the alkaline metal is employed; and, in the case of a hydrogenation, the amount of the catalyst such as palladium on carbon, platinum oxide, Raney nickel, Raney cobalt, etc. is employed in an amount of about 5 to about 1000% by weight, preferably about 10 to about 300% by weight based on Compound (XVI). This reaction is conducted advantageously by using a solvent which is inert to the reaction. Such solvent is not limited particularly provided that it allows the reactiinto be proceeded, and may for example be an alcohol, an ether, an aliphatic hydrocarbon, an aromatic hydrocarbon, an amide, an organic acid, as well as a mixture thereof. While the reaction time may vary depending on the type and the amount of the reducing agent employed as well as the activity and the amount of the catalyst employed, it is usually about 1 hour to about 100 hours, preferably about 1 hour to about 50 hours. The reaction temperature is usually about 0 to about 120° C., preferably about 20 to about 80° C. When a hydrogenating catalyst is employed, the pressure of hydrogen is usually about 1 to about 100 atm. While a product still in a solution or as a crude product may be used in the next reaction, it can be isolated from a reaction mixture by an ordinary method, and can readily be purified by a separating procedure such as recrystallization, distillation, chromatography, etc.

Compound (XVIII) is prepared by subjecting Compound (XVII) to an oxidation using an oxidizing agent followed by a treatment with a base whereby effecting a cyclization. The oxidizing agent employed frequently is cerium diammonium nitrate. The oxidizing agent is employed in an amount of about 1.0 to about 10 moles, preferably about 1.0 to about 3.0 moles per mole of Compound (XVII). This reaction is conducted advantageously by using a solvent, which is inert to the reaction. Such solvent is not limited particularly provided that it allows the reactiinto be proceeded, and may for example a mixture of water with a nitrile, an alcohol, an ether, an aliphatic hydrocarbon, an aromatic hydrocarbon and an amide. While the reaction time may vary depending on the type and the amount of the oxidizing agent employed as well as the activity and the amount of the catalyst employed, it is usually about 10 minutes to about 5 hours, preferably about 30 minutes to about 1 hour. The reaction temperature is usually about 10 to about 120° C., preferably about 0 to about 60° C. The resultant benzoquinone form is treated with a base to yield Compound (XVIII) which is a cyclized product. The base may for example be an inorganic base such as sodium carbonate, potassium carbonate, cesium carbonate, calcium carbonate, sodium hydrogen carbonate, etc., an aromatic amine such as pyridine, lutidine, etc., a tertiary amine such as triethylamine, tripropylamine, tributylamine, cyclohexyldimethylamine, 4-dimethylaminopyridine, N,N-dimethylaniline, N-methylpiperidine, N-methylpyrrolidine, N-methylmorpholine, etc., and the like. The reaction solvent may be the same as that employed in the oxidizing reaction. The reaction temperature is usually about −20 to about 150° C., preferably about 0 to about 100° C. The reaction time ranges usually from about 5 minutes to about 24 hours, preferably about 10 minutes to about 5 hours. Compound (XVIII) can be isolated from a reaction mixture by an ordinary method, and can readily be purified by a separating procedure such as recrystallization, distillation, chromatography, etc.

Compound (XIX) is prepared by reducing Compound (XVIII). The reducing agent may for example be sodium hydrosulfite, tin (II) chloride, etc. The amount of the reducing agent employed is about 1.0 to about 30 moles, preferably about 2.0 to about 5.0 moles per mole of Compound (XVIII) when sodium hydrosulfite is employed, while it is about 1.0 to about 10 moles, preferably about 2.0 to about 5.0 moles per mole of Compound (XVIII) when tin (II) chloride is employed. When tin (II) chloride is employed as the reducing agent, it is reacted under acidic condition in the presence of a mineral acid such as hydrochloric acid, etc. This reaction is conducted advantageously by using a solvent which is inert to the reaction. Such solvent is not limited particularly provided that it allows the reactiinto be proceeded, and may for example be water, or a mixture of water with an alcohol, an ether, an aliphatic hydrocarbon, an aromatic hydrocarbon and an amide. The reaction time ranges usually from about 10 minutes to about 10 hours, preferably about 10 minutes to about 2 hours. The reaction temperature is usually about 0 to about 100° C., preferably about 5 to about 80° C. While a product still in a solution or as a crude product may be used in the next reaction, it can be isolated from a reaction mixture by an ordinary method, and can readily be purified by a separating procedure such as recrystallization, distillation, chromatography, etc.

Compound (IIa) is synthesized by acylating Compound (XIX). Compound (XIX) and an acylating agent are reacted if necessary in the presence of a base or an acid. The acylating agent may for example be a corresponding carboxylic acid or a reactive derivative thereof (for example, acidic anhydride, ester, etc.). 1 mole of Compound (XIX) is reacted with about 1.0 to about 5.0 moles, preferably about 1.0 to about 2.0 moles of an acylating agent. This reaction is conducted without any solvent, or may advantageously be conducted using a solvent which is inert to the reaction. Such solvent is not limited particularly provided that it allows the reactiinto be proceeded, and may for example be an ether, an aliphatic hydrocarbon, an aromatic hydrocarbon, an amide, a halogenated hydrocarbon, a nitrile, a sulfoxide and an aromatic amine as well as a mixture thereof. The base employed if necessary may for example be triethylamine, pyridine, etc. The acid employed if necessary may for example be methanesulfonic acid, p-toluenesulfonic acid, camphorsulfonic acid, etc. The reaction temperature is usually about −20 to about 150° C., preferably about 0 to about 100° C. The reaction time ranges usually from about 5 minutes to about 24 hours, preferably about 10 minutes to about 5 hours. While Compound (IIa) still in a solution or as a crude product may be used in the next reaction, it can be isolated from a reaction mixture by an ordinary method, and can readily be purified by a separating procedure such as recrystallization, distillation, chromatography, etc.

Compound (XIX) is prepared also by a process shown in Synthesis Method 3-2.

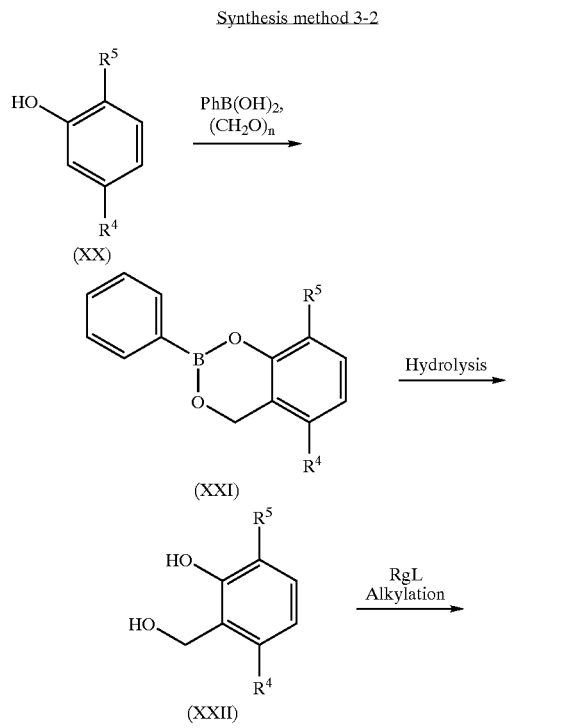

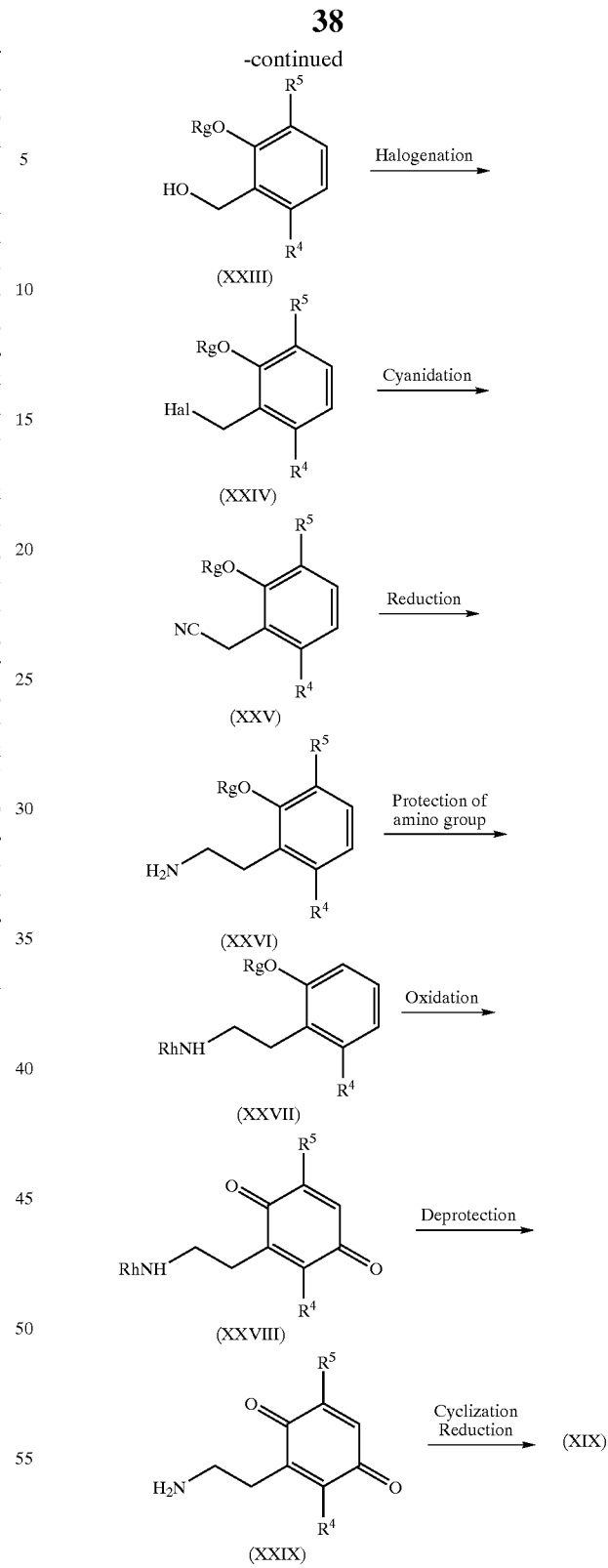

Hal: Halogen

Compound (XXII) is prepared from Compound (XX) via Compound (XXI) by a selective hydroxy methylation at the ortho-position of the phenol.

Compound (XXI) is produced by reacting Compound (XX) with phenylboronic acid and p-formaldehyde in the presence of an acid with removal of any generated water using for example a Dean-Stark trap. Phenylboronic acid is employed in an amount of about 1.0 to about 10 moles, preferably about 1.0 to about 1.5 moles per mole of Compound (XX). Paraformaldehyde is employed in an amount of about 1.0 to about 30 moles, preferably about 3 to about 5 moles per mole of Compound (XX). An acid catalyst may for example be an organic acid such as acetic acid, propionic acid and trichloroacetic acid which is used in an amount of about 0.01 to about 10 moles, preferably about 0.1 to about 0.5 moles per mole of Compound (XX). This reaction is conducted advantageously by using a solvent which is inert to the reaction. Such solvent is not limited particularly provided that it allows the reaction to proceed, and may for example be an ether, an aliphatic hydrocarbon and an aromatic hydrocarbon as well as a mixture thereof, preferably benzene and toluene. The reaction temperature is usually about 0 to about 200° C., preferably about 50 to about 150° C. While the reaction time may vary depending on the amount of the reagent employed, the type of the solvent and the reaction temperature, it is usually about 10 minutes to about 10 hours, preferably about 30 minutes to about 3 hours. While a product still in a solution or as a crude product may be used in the next reaction, it can be isolated from a reaction mixture by an ordinary method, and can readily be purified by a separating procedure such as recrystallization, distillation, chromatography, etc.

Compound (XXII) is produced from Compound (XXI) by a deprotection of phenylboronic acid using hydrogen peroxide, 1,3-propanediol, diethanol amine and the like. In this step, a solvent which is inert to the reaction such as benzene and toluene may be employed as an auxiliary solvent. While the reaction time may vary depending on the amount of the reagent employed, the type of the solvent and the reaction temperature, it is usually about 10 minutes to about 48 hours, preferably about 5 hours to about 16 hours. While a product still in a solution or as a crude product may be used in the next reaction, it can be isolated from a reaction mixture by an ordinary method, and can readily be purified by a separating procedure such as recrystallization, distillation, chromatography, etc.

Compound (XXIII) is obtained by alkylating the hydroxy group of the phenol in Compound (XXII) selectively using an alkylating agent represented by RgL. Rg denotes a $C_{1-6}$ alkyl (e.g., methyl, ethyl, etc.), and the "leaving group" represented by L is similar to those described above.

The amount of the alkylating agent is about 0.8 to about 5.0 moles, preferably about 1.0 to about 2.0 moles per mole of Compound (XXII).

Said "base" may for example be an inorganic base such as sodium hydroxide and potassium hydroxide, a basic salt such as sodium carbonate, potassium carbonate, cesium carbonate and sodium hydrogen carbonate, an aromatic amine such as pyridine and lutidine, a tertiary amine such as triethylamine, tripropylamine, tributylamine, cyclohexyldimethylamine, 4-dimethylaminopyridine, N,N-dimethylaniline, N-methylpiperidine, N-methylpyrrolidine and N-methylmorpholine, an alkaline metal hydride such as sodium hydride and potassium hydride, a metal amide such as sodium amide, lithium diisopropylamide and lithium hexamethyldisilazide and a metal alkoxide such as sodium methoxide, sodium ethoxide and potassium t-butoxide. The amount of a base employed per mole of Compound (XXII) is about 0.8 to about 5.0 moles, preferably about 1.0 to about 2.0 moles.

This reaction is conducted advantageously by using a solvent which is inert to the reaction. Such solvent is not limited particularly provided that it allows the reactiinto be proceeded, and may for example be an alcohol, an ether, an aliphatic hydrocarbon, an aromatic hydrocarbon, an amide, a halogenated hydrocarbon, a nitrile and a sulfoxide as well as a mixture thereof.

The reaction time ranges usually from about 30 minutes to about 48 hours, preferably about 1 hour to about 24 hours. The reaction temperature is usually about −20 to about 150° C., preferably about 0 to about 100° C.

Compound (XXIV) is obtained by converting the hydroxy group in Compound (XXIII) into a halogen using a halogenating reagent.

The "halogenating reagent" may for example be a phosphorus halide such as phosphorus tribromide, phosphorus pentabromide, phosphorus trichloride and phosphorus pentachloride, a thionyl halide such as thionyl chloride, as well as triphenylphosphine-carbon tetrahalide, diphenyltrihalogenophosphorane, triphenylphosphine dihalogenide, phosphonic acid triphenyl dihalogenide and the like. The amount of a halogenating reagent employed is about 1 to about 5 moles, preferably about 1 to about 2 moles per mole of Compound (XXIII).

This reaction may advantageously be conducted using a solvent which is inert to the reaction. Such solvent is not limited particularly provided that it allows the reactiinto be proceeded, and may for example be an alcohol, an aliphatic hydrocarbon, an aromatic hydrocarbon, an amide, a halogenated hydrocarbon, a nitrile, a sulfoxide, an organic acid, a nitroalkane and an aromatic amine as well as a mixture thereof.

The reaction temperature is usually about −50 to about 150° C., preferably about 0 to about 100° C. The reaction time ranges usually from about 5 minutes to about 24 hours, preferably about 10 minutes to about 12 hours.

While a product still in a solution or as a crude product may be used in the next reaction, it can be isolated from a reaction mixture by an ordinary method, and can readily, be purified by a conventional separating procedure (e.g., recrystallization, distillation, chromatography, etc.).

Compound (XXV) is obtained by converting the halogen in Compound (XXIV) into cyano using a cyaniding agent similarly to the cyanidation conducted for producing Compound (XVI) from Compound (XV).

Compound (XXVI) is obtained by reducing Compound (XXV) using a reducing agent similarly to the production of Compound (XVII) from Compound (XVI).

Compound (XXVII) is obtained by protecting amino group in Compound (XXVI) with an acylating agent if necessary in the presence of a base or an acid.

The amount of the acylating agent employed is about 1.0 to about 5.0 moles, preferably about 1.0 to about 2.0 moles per mole of Compound (XXVI).

Said "acylating agent" may for example be a carboxylic acid corresponding to an acyl group employed customarily as a protective group (for example, formyl group, acetyl group, trifluoroacetyl group) as well as a reactive derivative thereof (for example, acid halide, acid anhydride, ester, etc.).

The amount of a base employed is about 0.8 to about 5.0 moles, preferably about 1.0 to about 2.0 moles per mole of Compound (XXVI).

Said "base" may for example be triethylamine, pyridine and 4-dimethylaminopyridine.

Said "acid" may for example be methanesulfonic acid, p-toluenesulfonic acid and camphorsulfonic acid.

This reaction is conducted without any solvent, or may advantageously be conducted using a solvent which is inert to the reaction. Such solvent is not limited particularly provided that it allows the reactiinto be proceeded, and may for example be an ether, an aromatic hydrocarbon, an aliphatic hydrocarbon, an amide, a halogenated hydrocarbon, a nitrile, a sulfoxide and an aromatic amine as well as a mixture of two or more of these solvents.

The reaction temperature is usually about −20 to about 150° C., preferably about 0 to about 100° C. The reaction time ranges usually from about 5 minutes to about 24 hours, preferably about 10 minutes to about 5 hours.

While a product still in a solution or as a crude product may be used in the next reaction, it can be isolated from a reaction mixture by an ordinary method, and can readily be purified by a separating procedure such as recrystallization, distillation, chromatography, etc.

Compound (XXVIII) is obtained by oxidizing Compound (XXVII) into a quinone. An oxidizing agent employed frequently is chromic acid. The oxidizing agent is employed in an amount of about 1.0 to about 10 moles, preferably about 1.0 to about 3.0 moles per mole of Compound (XXVII). This reaction is conducted advantageously by using a solvent which is inert to the reaction. Such solvent is not limited particularly provided that it allows the reactiinto be proceeded, and may for example an organic acid, acetic anhydride, an aliphatic hydrocarbon, an aromatic hydrocarbon, a halogenated hydrocarbon, an aromatic amine as well as a mixture thereof with a water, preferably water. While the reaction time may vary depending on the type and the amount of the oxidizing agent employed, it is usually about 10 minutes to about 5 hours, preferably about 30 minutes to about 1 hour. The reaction temperature is usually about −10 to about 120° C., preferably about 0 to about 60° C.

Compound (XXIX) is obtained by deprotecting the protective group of amino group of Compound (XXVIII) using an acid or a base.

The amount of the acid or base is about 0.1 to about 50 moles, preferably about 1 to about 20 moles per mole of Compound (XXVIII).

Said "acid" may for example be a mineral acid such as hydrochloric acid, hydrobromic acid and sulfuric acid, a Lewis acid such as boron trichloride and boron tribromide, a combination of a Lewis acid with a thiol or a sulfide, as well as an organic acid such as trifluoroacetic acid and p-toluenesulfonic acid.

Said "base" may for example be a metal hydroxide such as sodium hydroxide, potassium hydroxide and barium hydroxide, a basic salt such as sodium carbonate and potassium carbonate, a metal alkoxide such as sodium methoxide, sodium ethoxide and potassium t-butoxide and organic base such as triethylamine, imidazole and formamidine.

This reaction is conducted without any solvent, or may advantageously be conducted using a solvent which is inert to the reaction. Such solvent is not limited particularly provided that it allows the reactiinto be proceeded, and may for example be an alcohol, an ether, an aromatic hydrocarbon, an aliphatic hydrocarbon, a halogenated hydrocarbon, a sulfoxide and water as well as a mixture of two or more of these solvents.

The reaction time ranges usually from about 10 minutes to about 50 hours, preferably about 30 minutes to about 12 hours. The reaction temperature is usually about 0 to about 200° C., preferably about 20 to about 120° C.

Compound (XIX) is obtained by subjecting Compound (XXIX) to cyclization followed by reduction. The cyclization involves treatment of a benzoquinone form with a base. The base may for example be an inorganic base such as sodium carbonate, potassium carbonate, cesium carbonate, calcium carbonate and sodium hydrogen carbonate, an aromatic amine such as pyridine and lutidine, a tertiary amine such as triethylamine, tripropylamine, tributylamine, cyclohexyldimethylamine, 4-dimethylaminopyridine, N,N-dimethylaniline, N-methylpiperidine, N-methylpyrrolidine and N-methylmorpholine. The reaction solvent may be similar to that employed in the oxidizing reaction. The reaction temperature is usually about −20 to about 150° C., preferably about 0 to about 100° C. The reaction time ranges usually from about 5 minutes to about 24 hours, preferably about 10 minutes to about 5 hours. The product can be isolated from a reaction mixture by an ordinary method, and can readily be purified by a separating procedure such as recrystallization, distillation, chromatography, etc. The subsequent reduction employs the same conditions as those for producing Compound (XIX) from Compound (XVIII).

Compound (XIX) can be produced also by a process shown in Synthesis Method 3-3.

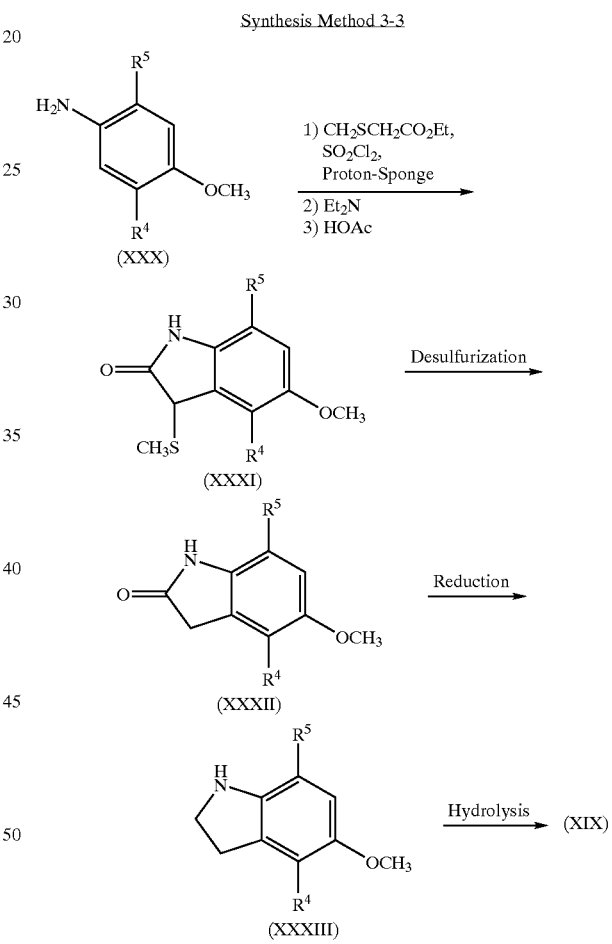

Synthesis Method 3-3

Compound (XXXI) can be produced from Compound (XXX), in accordance with the method by Gassman et al described in J. Am. Chem. Soc. Vol.95, 6508–6509 (1973), by reacting Compound (XXX) with an alkylchlorosulfonium ethyl acetate, reacting in the presence of a base, and then if necessary heating or treating with an acid to form an oxyindole ring. The alkylchlorosulfonium ethyl acetate can be produced by chlorinating an ethyl alkylthioacetate with chlorine, sulfuryl chloride, hypochlorite ester and the like. The alkylchlorosulfonium ethyl acetate is employed in an amount of about 0.9 to about 1.5 moles, preferably about 1.0 to about 1.2 moles per mole of Compound (XXX). This reaction is conducted advantageously by using a solvent which is inert to the reaction. While such solvent is not limited particularly provided that it allows the reactiinto be proceeded, it is preferably a halogenated hydrocarbon. The reaction time is usually about 5 minutes to about 5 hours, preferably about 30 minutes to about 2 hours. The reaction temperature is usually about −100 to about 50° C., preferably about −80 to about 50° C. The base which may be exemplified is an aromatic amine such as pyridine and lutidine, a tertiary amine such as triethylamine, tripropylamine, tributylamine, cyclohexyldimethylamine, N,N,N',N'-tetramethyl-1,8-naphthalenediamine, 4-dimethylaminopyridine, N,N-dimethylaniline, N-methylpiperidine, N-methylpyrrolidine and N-methylmorpholine. The reaction temperature is usually −80 to 50° C., preferably about 0 to about 20° C. The optionally employed acid may for example be a mineral acid such as hydrochloric acid, hydrobromic acid and sulfuric acid, a sulfonic acid such as methanesulfonic acid, trifluoromethanesulfonic acid and fluorosulfonic acid, formic acid, acetic acid and trichloroacetic acid. The acid may be employed in an amount of about 1 to about 200 moles, preferably about 1 to about 10 moles per mole of Compound (XXX). The reaction time is usually about 1 minute to about 5 hours, preferably about 30 minutes to about 2 hours. The reaction temperature is usually about −50 to about 150° C., preferably about 0 to about 50° C. In this step, a solvent which is inert to the reaction such as diethylether, dichloromethane and toluene may be employed as an auxiliary solvent. A heating procedure may alternatively be employed in the synthesis instead of the acid treatment. The reaction temperature is usually about 50 to about 250° C., preferably about 50 to about 150° C. The reaction time ranges usually from about 10 minutes to about 48 hours, preferably about 30 minutes to about 5 hours. In this step, a solvent which is inert to the reaction such as toluene, hexane and decaline may be employed as an auxiliary solvent. While the product still as a crude product may be used in the next reaction, it can be isolated from a reaction mixture by an ordinary method, and can readily be purified by a separating procedure such as recrystallization, distillation, chromatography, etc.

Compound (XXXII) can be produced from Compound (XXXI) by a desulfurization using a metal catalyst such as Raney nickel or tin, preferably Raney nickel, or by a desulfurization in accordance with a method by Terrence et al reported in Synlett, 663 (1996), using triphenylphosphine and p-toluenesulfonic acid. Raney nickel is employed in an amount of about 0.1 to about 20 g, preferably about 1 to about 5 g per mmole of Compound (XXXI). This reaction is conducted without any solvent, or may advantageously be conducted using a solvent which is inert to the reaction. Such solvent is not limited particularly provided that it allows the reactiinto be proceeded, and may for example be an alcohol, an ether, an aliphatic hydrocarbon, an aromatic hydrocarbon, an amide, a nitrile as well as a mixture thereof. The reaction time ranges usually from about 5 minutes to about 48 hours, preferably about 30 minutes to about 10 hours. The reaction temperature is usually about 0 to about 150° C., preferably about 20 to about 100° C. While the product once removed of any catalyst can be employed still as a crude product in the next reaction, it can be isolated from a reaction mixture by an ordinary method, and can readily be purified by a separating procedure such as recrystallization, distillation, chromatography, etc.

Compound (XXXIII) is produced by reducing Compound (XXXII). A reducing agent employed in the reduction may for example be a metal hydride such as aluminum hydride and diisobutylaluminum gydride, a metal hydrogen complex such as lithium aluminum hydride, sodium borohydride and Red-Al, a borane complex such as boran tetrahydrofurane complex and borane dimethyl sulfide complex, an alkyl borane such as thexylborane and disiamylborane, diborane and the like. The amount of the reducing agent is about 0.3 to about 10 moles, preferably about 0.5 to about 3.0 mole per mole of Compound (XXXII) when a metal hydride or a metal hydrogen complex is employed, about 1.0 to about 5.0 moles per mole of Compound (XXXII) when a borane complex, an alkyl borane or a diborane is employed, and about 1.0 to about 20 equivalents, preferably about 1 to about 5 equivalents when a metal is employed. This reaction is conducted advantageously by using a solvent which is inert to the reaction. Such solvent is preferably an ether, an aliphatic hydrocarbon and aromatic hydrocarbon as well as a mixture thereof. While a product once made free of any catalyst can be employed still as a crude product in the next reaction, it can be isolated from a reaction mixture by an ordinary method, and can readily be purified by a separating procedure such as recrystallization, distillation, chromatography, etc.

Compound (XIX) can be produced also by a process shown in Synthesis Method 3-4.

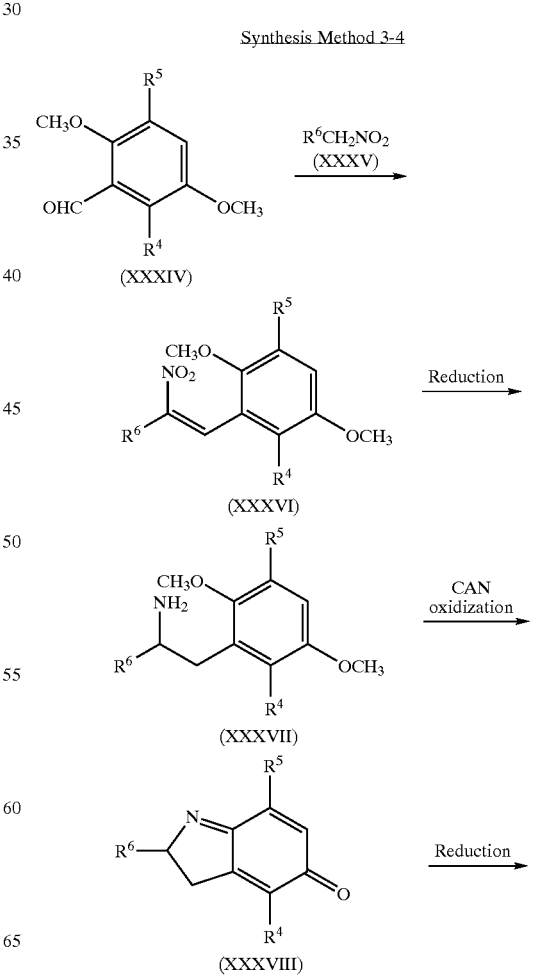

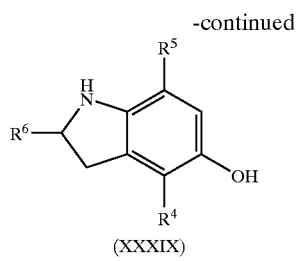

(XXXIX)

Introduction of protective group →

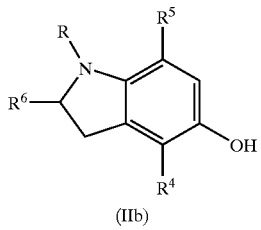

(IIb)

Compound (XXXVI) can be produced by condensing Compound (XXXIV) and Compound (XXXV) in the presence of a base. Compound (XXXV) is employed in an amount of about 1.0 to about 300 moles, preferably about 3.0 to about 100 moles per mole of Compound (XXXIV). The base may for example be an ammonium salt such as ammonium acetate and ammonium formate, an inorganic base such as sodium carbonate, potassium carbonate, cesium carbonate, calcium carbonate and sodium hydrogen carbonate, an aromatic amine such as pyridine and lutidine, a tertiary amine such as triethylamine, tripropylamine, tributylamine, cyclohexyldimethylamine, 4-dimethylaminopyridine, N,N-dimethylaniline, N-methylpiperidine, N-methylpyrrolidine and N-methylmorpholine. The amount of a base employed per mole of Compound (XXXIV) is about 0.1 to about 10.0 moles, preferably about 0.2 to about 5.0 moles. This reaction is conducted without any solvent, or may advantageously be conducted using a solvent which is inert to the reaction. Such solvent is not limited particularly provided that it allows the reactiinto be proceeded, and may for example be an alcohol, an ether, an aliphatic hydrocarbon, an aromatic hydrocarbon, an amide, a halogenated hydrocarbon, a nitrile and a sulfoxide as well as a mixture thereof. The reaction time ranges usually from about 30 minutes to about 48 hours, preferably about 1 hour to about 24 hours. The reaction temperature is usually about 0 to about 150° C., preferably about 20 to about 100° C.

Compound (XXXVII) is produced by reducing Compound (XXXVI). A reducing agent employed in this reduction may for example be a metal hydride such as aluminum hydride and diisobutylaluminum hydride, a metal hydrogen complex such as lithium aluminum hydride and sodium borohydride, a borane complex such as borane tetrahydrofuran complex and borane dimethyl sulfide complex, an alkyl borane such as thexylborane and disiamylborane, diborane, as well as a metal such as zinc, aluminum, tin and iron, an alkaline metal such as sodium and lithium in combination with a liquid ammonia (Birch reduction). A hydrogenating catalyst may for example be palladium on carbon, platinum oxide, Raney nickel, Raney cobalt and the like. The amount of the reducing agent is about 1.0 to about 10 moles, preferably about 1.0 to about 3.0 mole per mole of Compound (XXXVI) when a metal hydride is employed, about 1.0 to about 10 moles, preferably about 1.0 to about 3.0 moles per mole of Compound (XXXVI) when a metal hydrogen complex is employed, about 1.0 to about 5.0 moles per mole of Compound (XXXVI) when a borane complex, an alkyl borane or a diborane is employed, about 1.0 to about 20 equivalents, preferably about 1 to about 5 equivalents when a metal is employed, and about 1 to about 20 equivalents, preferably about 1 to about 5 equivalents when an alkaline metal is employed, and in the case of hydrogenation the amount of a catalyst such as palladium on carbon, platinum oxide, Raney nickel and Raney cobalt is employed in an amount of about 5 to about 1000% by weight, preferably about 10 to about 300% by weight based on Compound (XXXVI). This reaction is conducted advantageously by using a solvent which is inert to the reaction. Such solvent is not limited particularly provided that it allows the reactiinto be proceeded, and may for example be an alcohol, an ether, an aliphatic hydrocarbon, an aromatic hydrocarbon, an amide, an organic acid, as well as a mixture thereof. When-Raney nickel or Raney cobalt catalyst is employed, an amine such as ammonia may be further added in order to suppress any side reaction. While the reaction time may vary depending on the type and the amount of the reducing agent employed as well as the activity and the amount of the catalyst employed, it is usually about 1 hour to about 100 hours, preferably about 1 hour to about 50 hours. The reaction temperature is usually about 0 to about 120° C., preferably about 20 to about 80° C. When a hydrogenating catalyst is employed; the pressure of hydrogen is usually about 1 to about 100 atm. While a product still in a solution or as a crude product may be used in the next reaction, it can be isolated from a reaction mixture by an ordinary method, and can readily be purified by a separating procedure such as recrystallization, distillation and chromatography.

The production of Compound (XXXVIII) from Compound (XXXVII) is in accordance with the production of Compound (XVIII) from Compound (XVII).

The production of Compound (XXXIX) from Compound (XXXVIII) is in accordance with the production of Compound (XIX) from Compound (XVIII).

The production of Compound (IIb) from Compound (XXXVIX) is in accordance with the production of Compound (IIa) from Compound (XIX).

When a starting compound has as its substituent amino, carboxyl or hydroxy group in each reaction described above, such group may be subjected to an introduction of a protective group employed conventionally in peptide chemistry, and the protective group is removed if necessary after the reaction to yield the desired compound.

Examples of the amino protective group include formyl or a $C_{1-6}$ alkylcarbonyl (for example, acetyl, propionyl, etc.), phenylcarbonyl, a $C_{1-6}$ alkoxycarbonyl (for example, methoxycarbonyl, ethoxycarbonyl, etc.), phenyloxycarbonyl, a $C_{7-10}$ aralkyloxycarbonyl (for example, benzyloxycarbonyl, etc.), trityl, phthaloyl and the like, each of which may optionally be substituted. Examples of the substituent include a halogen atom (for example, fluorine, chlorine, bromine, iodine, etc.)., a $C_{1-6}$ alkylcarbonyl (for example, acetyl, propionyl, valeryl, etc.), nitro and the like, and the number of substituents is one to about three.

Examples of the carboxyl protective group include a $C_{1-6}$ alkyl (for example, methyl, ethyl, propyl, isopropyl, butyl, tert-butyl, etc.), phenyl, trityl and silyl, each of which may optionally be substituted. Examples of the substituent include a halogen atom (for example, fluorine, chlorine, bromine, iodine, etc.), formyl, a $C_{1-6}$ alkylcarbonyl (for example, acetyl, propionyl, butylcarbonyl, etc.), nitro, a $C_{1-6}$ alkyl (for example, methyl, ethyl, tert-butyl, etc.), a $C_{6-10}$ aryl (for example, phenyl, naphthyl, etc.), and the number of substituents is one to about three.

Examples of the hydroxy group protective group include formyl or a $C_{1-6}$ alkyl (for example, methyl, ethyl, propyl, isopropyl, butyl, tert-butyl, etc.), phenyl, a $C_{7-11}$ aralkyl (for example, benzyl, etc.), a $C_{1-6}$ alkylcarbonyl (for example, acetyl, propionyl, etc.), phenyloxycarbonyl, a $C_{1-6}$ aralkyloxycarbonyl (for example, benzyloxycarbonyl, etc.), tetrahydropyranyl, tetrahydrofuranyl and silyl. Examples of the substituent include a halogen atom (for example, fluorine, chlorine, bromine, iodine, etc.), a $C_{1-6}$ alkyl (for example, methyl, tert-butyl, etc.), a $C_{7-11}$ aralkyl (for example, benzyl, etc.), a $C_{6-10}$ aryl (for example, phenyl, naphthyl, etc.), nitro and the like, and the number of substituents is one to about four.

A method for removing the protective group may be a per se known method or an analogous method, such as treatment with an acid, a base, ultraviolet, hydrazine, phenylhydrazine, sodium N-methyldithiocarbamate, tetrabutylammonium fluoride, palladium acetate and the like as well as a reducing reaction.

In any method, only one of or a combination of a deprotecting reaction, an acylating reaction, an alkylating reaction, a hydrogenating reaction, an oxidizing reaction, a reducing reaction, a carbon chain elongating reaction and a substituent-exchanging reaction may be employed to synthesize Compound (I). Any of these reactions may be found for example in SHIN-JIKKENKAGAKU-KOZA, Vols.14 and 15, published by MARUZEN, (1977).

Examples of the "alcohol" described above include methanol, ethanol, propanol, isopropanol, tert-butanol, etc.

Examples of the "ether" described above include diethylether; diisopropylether, diphenylether, tetrahydrofuran, dioxane, 1,2-dimethoxyethane, etc.

Examples of the "halogenated hydrocarbon" include dichloromethane, chloroform, 1,2-dichloroethane, carbon tetrachloride, etc.

Examples of the "aliphatic hydrocarbon" described above include hexane, pentane, cyclohexane, etc.

Examples of the "aromatic hydrocarbon" described above include benzene, toluene, xylene, chlorobenzene, etc.

Examples of the "aromatic amine" described above include pyridine, lutidine, quinoline, etc.

Examples of the "amide" described above include N,N-dimethylformamide, N,N-dimethylacetoamide, hexamethylphosphoric triamide, etc.

Examples of the "ketone" described above include acetone, methylethylketone, etc.

Examples of "sulfoxide" described above include dimethylsulfoxide, etc.

Examples of the "nitrile" described above include acetonitrile, propionitrile, etc.

Examples of the "organic acid" described above may for example be acetic acid, propionic acid, trifluoroacetic acid, etc.

Examples of the "aniline" described above include N,N-diethylaniline, N,N-dimethylaniline, etc.

Examples of the "nitroalkane" described above may for example be nitromethane, nitroethane, etc.

The desired product yielded as a free form by the reaction described above may be converted into a salt by an ordinary method, while the product yielded as a salt may be converted into a free form or another salt by an ordinary method. Compound (I) thus obtained is isolated and purified from a reaction mixture by a known means such as partition, concentration, solvent extraction, fractional distillation, crystallization, recrystallization, chromatography and the like.

When Compound (I) or (I') exists as a configuration isomer, diastereomer or conformer, each can be isolated if necessary by any isolation or separation means described above. When Compound (I) or (I') is a racemate, it can be separated by an ordinary optical resolution means into S and R forms.

When Compound (I) or (I') exists as any of its stereoisomers, the stereoisomer, either alone or in a mixture thereof, is understood to be encompassed by the present invention.

Compound (I) or (I') may also be a hydrate or a anhydride.

Compound (I) or (I') may also be labeled with an isotope (for example, $^3H$, $^{14}C$ and $^{35}S$).

A prodrug of Compound (I) is a compound capable of being converted into Compound (I) as a result of a reaction with an enzyme, gastric acid, etc. under in vivo physiological conditions, i.e., a compound subjected to enzymatic oxidation, reduction, hydrolysis, etc. to change into Compound (I) or a compound hydrolyzed by gastric acid to change into Compound (I). The prodrug of Compound (I) may for example be a compound resulting from acylation, alkylation or phosphorylation of amino group of Compound (I) (for example, a compound resulting from eicosanoylation, alanylation, pentylaminocarbonylation, (5-methyl-2-oxo-1,3-dioxolen-4-yl)methoxycarbonylation, tetrahydrofuranylation, pyrrolidylmethylation, pivaloyloxymethylation or tert-butylation of amino group of Compound (I), etc.); a compound resulting from acylation, alkylation, phosphorylation or boration of hydroxy group of Compound (I) (for example, a compound resulting from acetylation, palmitoylation, propanoylation, pivaloylation, succinylation, fumarylation, alanylation or dimethylaminomethylcarbonylation of hydroxy group of Compound (I), etc.; a compound resulting from an esterification or an amidation of carboxyl group of Compound (I) (for example, a compound resulting from ethyl esterification, phenyl esterification, carboxymethyl esterification, dimethylaminomethyl esterification, pivaloyloxymethyl esterification, ethoxycarbonyloxyethyl esterification, phthalidyl esterification, (5-methyl-2-oxo-1,3-dioxolen-4-yl)methyl esterification, cyclohexyloxycarbonylethyl esterification and methylamidation of a carboxyl group of Compound (I), etc.) and the like. Any of these compounds can be produced from Compound (I) by a per se known method.

A prodrug of Compound (I) may also be a compound which is changed into Compound (I) under physiological conditions described in pages 163 to 198 in Molecular Designing in Vol.7 of "Pharmaceutical Development (IYAKUHIN-NO-KAIHATSU)" published in 1990 by HIROKAWASHOTEN.

Since Compound (I) or (I') of the present invention has an excellent lipid peroxidation inhibitory activity, low toxicity and less side effect, it is useful as a pharmaceutical.

Compound (I) or (I') of the present invention exhibits a lipid peroxidation inhibitory activity based on an excellent antioxidative effect in a mammal (for example, mouse, rat, hamster, rabbit, cat, dog, cattle, sheep, monkey, human and the like), is effective in prophylaxis and/or therapy against a central nerve system disease or failure such as, for example, an ischemic central nerve disease (e.g., cerebral infarction, cerebral hemorrhage, cerebral edema), a central nerve damage (e.g., cranial trauma, spinal damage, whiplash), a neurodegenerative disease (e.g., Alzheimer's disease, Parkinson's disease, Huntington's chorea, amyotrophic lateral sclerosis), a vascular dementia (e.g., multi-infarct dementia, Binswanger's disease), manic-depressive, melancholia, schizophrenia, chronic pain, trigeminal neuralgia, migraine, a circulatory system disease or failure such as, for example, an ischemic heart disease (e.g., cardiac infarction, angina pectoris), arterial sclerosis, post-PCTA arterial restenosis, a lower urinary tract disease or failure (e.g., dysuria, urinary incontinence) and a diabetic neurosis, and is employed as a prophylactic and therapeutic agent against any of these disorders listed above.

Compound (I) or (I') is less toxic, and it can safely be administered via an oral or parenteral route (e.g., local, rectal, intravenous administration) as it is or as a pharmaceutical composition in a mixture with a pharmaceutically acceptable carrier, such as tablets (including sugar-coated and film-coated tablets), powders, granules, capsules (including soft capsules), liquids, injectable solutions, nasal drops, suppositories, sustained-release formulations, plasters, chewing gums and the like. The formulation of the present invention contains 0.01 to about 100% by weight of Compound (I) or (I') based on the entire formulation. While the dose may vary depending on the subject, the administration route and the disease to be treated, it contains as an active component Compound (I) in an amount of about 0.1 to about 20 mg/kg body weight, preferably about 0.2 to about 10 mg/kg bodyweight, more preferably about 0.5 to about 10 mg/kg body weight given once a day or several times a day as divided doses when it is administered orally for example as a therapeutic agent against Alzheimer disease to an adult. It may be employed in combination with other active components [for example, a choline esterase inhibitor (e.g., Aricept (Donepezil), etc.), a cerebral function activator (e.g., Idebenone, Vinpocetine, etc.), a Parkinson's disease-treating agent (e.g., L-dopa, etc.), a neurotrophic factor and the like). Any of such other active components can be mixed with Compound (I) or (I') by a per se knonw method, and may be formulated in combination into a single pharmaceutical composition (for example, tablets, powders, granules, capsules (including soft capsules), liquids, injectable solutions, suppositories, sustained-release formulations and the like) or may be formulated individually and given simultaneously or sequentially at a certain interval to an identical subject.

Examples of a pharmaceutically acceptable carrier which may be employed in producing the formulation of the present invention include any of various organic or inorganic carriers employed conventionally as components of a formulation. For example, there are um excipients, lubricants, binders and disintegrants in a solid formulation; solvents, solubilizing agents, suspending agents, isotonic agents, buffering agents and analgesics in a liquid formulation, and the like. If necessary, any of conventional additives such as preservatives, antioxidants, colorants, sweeteners, adsorbents, wetting agents, etc., may also be employed.

Examples of the excipient include lactose, sugar, D-mannitol, starch, corn starch, crystalline cellulose, light anhydrous silicic acid and the like.

Examples of the lubricant include magnesium stearate, calcium stearate, talc, colloidal silica and the like.

Examples of the binder include crystalline cellulose, sugar, D-mannitol, dextrin, hydroxypropyl cellulose, hydroxypropyl methylcellulose, polyvinyl pyrrolidone, starch, sucrose, gelatin, methyl cellulose, sodium carboxymethyl cellulose and the like.

Examples of the disintegrant include starch, carboxymethyl cellulose, potassium carboxymethyl cellulose, sodium croscarmellose, sodium carboxymethyl starch, L-hydroxypropyl cellulose and the like.

Examples of the solvent include water for injection, alcohol, propylene glycol, macrogol, sesame oil, corn oil, olive oil and the like.

Examples of the solubilizing agent include polyethylene glycol, propylene glycol, D-mannitol, benzyl benzoate, ethanol, tris-aminomethane, cholesterol, triethanolamine, sodium carbonate, sodium citrate and the like.

Examples of the suspending agent include surfactants such as stearyl triethanolamine, sodium lauryl sulfate, lauryl aminopropionic acid, lecithin, benzalkonium chloride, benzethonium chloride, glycerin monostearate, etc.; hydrophilic polymers such as polyinyl alcohol, polyvinyl pyrrolidone, sodium carboxymethyl cellulose, methyl cellulose, hydroxymethyl cellulose, hydroxyethyl cellulose, hydroxypropyl cellulose, etc., and the like.

Examples of the isotonic agent include glucose, D-sorbitol, sodium chloride, glycerin, D-mannitol and the like.

Examples of the buffering agent include a buffer solution of phosphates, acetates, carbonates and citrates, etc.

Examples of the analgesic include benzyl alcohol, etc.

Examples of the preservative include p-oxybenzoate, chlorobutanol, benzyl alcohol, phenethyl alcohol, dehydroacetic acid, sorbic acid and the like.

Examples of the antioxidant include sulfites, ascorbic acid, α-tocopherol and the like.

BEST MODE FOR CARRYING OUT THE INVENTION

The present invention is further detailed in the following Reference Examples, Examples, Formulation Examples and Experiments, which serve only as examples and are not intended to restrict the present invention and can be modified without departing the scope of the present invention.

"Room temperature" in any of the following Reference Examples and Examples is usually about 10° C. to about 35° C. All the percents are by weight unless otherwise specified. An yield is represented as mol/mol %. The basic silica gel employed here was NH-DM1020 produced by FUJI SILICIA KAGAKU KK.

The Raney nickel employed here is NDHT-90 produced by KAWAKEN FINE KK. An NMR spectrum which could not be validated due to broad OH, NH proton and the like was not included in data.

Other abbreviations employed herein have meanings shown below.

s: singlet
d: doublet
t: triplet
q: quartet
m: multiplet
dd: double doublet
dt: double triplet
br: broad
J: coupling constant
Hz: Hertz
$CDCl_3$: deuterated chloroform
$DMSO-d_6$: deuterated dimethylsulfoxide
$CD_3OD$: deuterated methanol
$^1H$-NMR: Proton nuclear magnetic resonance
THF: tetrahydrofuran.

EXAMPES

Reference Example 1

N-(2,5-Dimethylphenyl)-2,2,2-trifluoroacetoamide

To a solution of 2,5-dimethylaniline (103 g, 0.849 mol) and triethylamine (103 g, 1.02 mol) in THF (500 ml) was added dropwise trifluoroacetic anhydride (132 ml, 0.935 mol) over 20 minutes with cooling on ice and the mixture was stirred for 10 minutes at the same temperature. Water was added to the reaction mixture and the mixture was extracted three times with diisopropyl ether. The organic layers were combined and washed with water (twice) and saturated brine, dried over magnesium sulfate, treated with an active charcoal, filtered and concentrated under reduced pressure to obtain 185 g of the title compound as a solid. Yield: 100%. An analytical sample was recrystallized from diisopropylether-hexane.

Melting point: 90–92° C.

$^1$H-NMR (CDCl$_3$) δ 2.25 (3H, s), 2.34 (3H, s), 7.01 (1H, d, J=7.7 Hz), 7.13 (1H, d, J=7.7 Hz), 7.50–7.90 (1H, br), 7.60 (1H, s).

Reference Example 2
2,5-Dimethyl-N-(2-methyl-2-propenyl)benzeneamine

To a solution of N-(2,5-dimethylphenyl)-2,2,2-trifluoroacetoamide (5.87 g, 27.0 mmol) in acetone (50 ml) were added potassium iodide (4.49 g 27.0 mmol), 3-chloro-2-methyl-1-propene (8.0 ml, 81 mmol) and pulverized 85% potassium hydroxide (5.3 g, 80 mmol), and the mixture was heated under reflux for 1 hour. Water was added to the reaction mixture and the mixture was extracted twice with hexane. The organic layers were combined, washed with water and saturated brine, dried over magnesium sulfate, filtered and concentrated under reduced pressure. The residue was purified by column chromatography on silica gel (hexane:ethyl acetate=100:1, followed by 50:1) to obtain 4.11 g of the title compound.

Yield: 87%.

Oil.

$^1$H-NMR (CDCl$_3$) 1.81 (3H, s), 2.13 (3H, s), 2.28 (3H, s), 3.67 (1H., br s), 3.72 (2H, s), 4.86–5.03 (2H, m), 6.39 (1H, s), 6.47 (1H, d, J=7.6 Hz), 6.94 (1H, d, J=7.6 Hz).

Reference Example 3
2,3-Dihydro-2,4,7-tetramethyl-1H-indole

To a solution of 2,5-dimethyl-N-(2-methyl-2-propenyl)benzeneamine (3.96 g, 22.6 mmol) in xylene (20 ml) was added zinc chloride (9.24 g, 67.8 mmol) and stirred at 140° C. for 2 hours. The reaction mixture was cooled to 115° C., added dropwise thereto a solution of sodium acetate (11.2 g, 0.137 mol) in water (30 ml). The resultant solution was cooled, and extracted twice with diisopropyl ether. The organic layers were combined, washed with water and saturated brine, dried over magnesium sulfate, filtered and concentrated under reduced pressure. The residue was purified by column chromatography on silica gel (hexane:ethyl acetate 20:1) to obtain 3.10 g of the title compound.

Yield: 78%.

Oil.

$^1$H-NMR (CDCl$_3$) δ 1.34 (6H, s), 2.07 (3H, s), 2.15 (3H, s), 2.80 (2H, s), 2.90–3.90 (1H, br), 6.47 (1H, d, J=7.6 Hz), 6.77 (1H, d, J=7.6 Hz).

Reference Example 4
2,3-Dihydro-2,2,4,7-tetramethyl-5H-indol-5-one

To a solution of 65% potassium nitrosodisulfonate (10.4 g, 25.2 mmol) in pH 6.86 phosphate buffer (320 ml) was added a solution of 2,3-dihydro-2,2,4,7-tetramethyl-1H-indole (2.21 g, 12.6 mmol) in methanol (50 ml) and stirred at room temperature for 1.5 hours. The reaction mixture was extracted three times with toluene. The organic layers were combined, washed with water and saturated brine, dried over magnesium sulfate, filtered and concentrated under reduced pressure. The residue was subjected to a column chromatography on a silica gel (hexane:ethyl acetate=5:1) and recrystallized from ethyl acetate-hexane to obtain 1.71 g of the title compound.

Yield: 72%.

Melting point: 107–109° C.

$^1$H-NMR (CDCl$_3$) δ 1.43 (6H, S), 1.90 (3H, t, J=1.8 Hz), 2.27 (3H, d, J=1.4 Hz), 2.63 (2H, d, J=2.0 Hz), 6.39 (1H, d, J=1.4 Hz).

Reference Example 5
2,3-Dihydro-2,2,4,7-tetramethyl-1H-indol-5-ol

To a solution of 2,3-dihydro-2,2,4,7-tetramethyl-5H-indol-5-one (7.36 g, 38.9 mmol) in ethyl acetate (100 ml) was added a solution of sodium hydrosulfite (14.9 g, 85.6 mmol) in water (50 ml) and shaken. The aqueous layer was separated, and the organic layer was washed with water and saturated brine, dried over magnesium sulfate, filtered and concentrated under reduced pressure. The residue was recrystallized from ethanol-hexane to obtain 6.17 g of the title compound.

Yield: 83%.

Melting point: 186–187° C.

$^1$H-NMR (DMSO-d$_6$) δ 1.21 (6H, s), 1.91 (6H, s), 2.61 (2H, s), 4.39 (1H, s), 6.22 (1H, s), 8.05 (1H, s).

Reference Example 6
2,3-Dihydro-5-hydroxy-2,2,4,7-tetramethyl-1H-indole-1-carbaldehyde Acetic anhydride (2.0 ml, 21 mmol) was added to formic acid (5 ml) and stirred at room temperature for 20 minutes. To the mixture was added 2,3-dihydro-2,2.,4,7-tetramethyl-1H-indol-5-ol (1.32 g, 6.90 mmol) and stirred at room temperature for 20 minutes. The reaction mixture was concentrated under reduced pressure, neutralized with saturated aqueous sodium hydrogen carbonate solution and extracted three times with ethyl acetate. The organic layers were combined, washed with water and saturated brine, dried over magnesium sulfate, filtered and concentrated under reduced pressure. The residue was dissolved in methanol (10 ml) and then 1N aqueous solution of sodium hydroxide (7 ml, 7 mmol) was added with cooling on ice. The mixture was stirred at the same temperature for 3 minutes. The reaction mixture was neutralized with 1N hydrochloric acid with cooling on ice, and extracted three times with ethyl acetate. The organic layers were combined, washed with water and saturated brine, dried over magnesium sulfate, filtered and concentrated under reduced pressure. The residue was recrystallized from ethanol-hexane to obtain 1.17 g of the title compound.

Yield: 77%.

Melting point: 175–177° C.

$^1$H-NMR (CDCl$_3$) δ 1.53, 1.66 (6H, s), 2.09 (3H, s), 2.25, 2.32 (3H, s), 2.82, 2.89 (2H, s), 5.00–6.20 (1H, br), 6.49 (1H, s), 8.32, 8.99 (1H, s).

Reference Example 7
2,3-Dihydro-2,2,4,7-tetramethyl-5-[(2-methyl-2-propenyl)oxy]-1H-indole-1-carbaldehyde To a solution of 2,3-dihydro-5-hydroxy-2,2,4,7-tetramethyl-1H-indole-1-carbaldehyde (2.29 g, 10.4 mmol) in DMF (15 ml) was added 60% dispersion of sodium hydride in oil (0.42 g, 12 mmol) with cooling on ice and stirred under nitrogen atmosphere at the same temperature for 5 minutes. To the resulting mixture was added 3-chloro-2-methyl-1-propene (1.3 ml, 13 mmol) and stirred at room temperature for 30 minutes and at 60° C. for 15 minutes. The reaction mixture was poured into a saturated aqueous solution of ammonium chloride, and extracted three times with ethyl acetate. The organic layers were combined, washed with water and saturated brine, dried over magnesium sulfate, filtered and concentrated under reduced pressure. The residue was recrystallized from diisopropyl ether-hexane to obtain 1.95 g of the title compound.

Yield: 69%.

Melting point: 83–95° C.

$^1$H-NMR (CDCl$_3$) δ 1.53, 1.65 (6H, s), 1.84 (3H, s), 2.10 (3H, s), 2.29, 2.37 (3H, s), 2.82, 2.89 (2H, s), 4.39 (2H, s), 4.98 (1H, s), 5.11 (1H, s), 6.46, 6.51 (1H, s), 8.34, 9.02 (1H, s).

Reference Example 8

2,3-Dihydro-5-hydroxy-2,2,4,7-tetramethyl-6-(2-methyl-2-propenyl)-1H-indole-1-carbaldehyde A solution of 2,3-dihydro-2,2,4,7-tetramethyl-5-[(2-methyl-2-propenyl)oxy]-1H-indole-1-carbaldehyde (2.38 g, 8.71 mmol) in N,N-diethylaniline (5 ml) was stirred under nitrogen atmosphere at 200° C. for 8 hours. The reaction mixture was allowed to stand overnight, hexane was added thereto, and the crystal was collected by a filtration and recrystallized from ethanol-hexane to obtain 2.10 g of the title compound.

Yield: 84%.

Melting point: 166–168° C.

$^1$H-NMR (DMSO-ds) δ 1.45, 1.50 (6H, br s), 1.73 (3H, s), 1.95, 2.12 (3H, br s), 2.04 (3H, s), 2.79, 2.84 (2H, br s), 3.32 (2H, s), 4.29 (1H, s), 4.65 (1H, s), 7.93 (1H, s), 8.27, 8.75 (1H, br s).

Reference Example 9

To a suspension of ethyl 4[methyl(phenylamino)thioxomethyl]amino]-1-piperidine carboxylate (4.02 g, 12.5 mmol) in carbon tetrachloride (25 ml) was added dropwise a solution of bromine (2.00 g, 2.5 mmol) in carbon tetrachloride (10 ml) and the mixture was stirred at room temperature for 30 minutes and heated under reflux for 1 hour. The insolubles were isolated by filtration and washed with hexane. The insolubles were dissolved in 48% hydrobromic acid (40 ml) and heated under reflux for 2 hours. The reaction mixture was cooled to 0° C., neutralized with 25% aqueous ammonia, and extracted twice with ethyl acetate. The organic layers were combined, washed with water and saturated brine, dried over magnesium sulfate, filtered and concentrated under reduced pressure. The residue was combined with diisopropyl ether and the insolubles were removed by filtration, and the filtrate was concentrated under reduced pressure. The residue was dissolved in methanol, combined with a 10% hydrogen chloride methanol solution (11 ml), and concentrated under reduced pressure. The residue was recrystallized from methanol-diisopropyl ether to obtain 2.53 g of the title compound.

Yield: 71%.

Melting point: 287–289° C.

$^1$H-NMR (DMSO-d$_6$) δ 1.80–2.00 (2H, m), 2.00–2.29 (2H, in), 2.91–3.26 (2H, m), 3.04 (3H, s), 3.28–3.47 (2H, m), 4.36–4.58 (1H, m), 7.04–7.17 (1H, m), 7.26–7.37 (1H, m), 7.50 (1H, d, J=8.0 Hz), 7.81 (1H, d, J=8.0 Hz), 9.11 (2H, br s).

Reference Example 10

2,5-Dimethoxy-1,4-dimethylbenzene

To a solution of 2,5-dimethyl-1,4-benzoquinone (68.1 g, 0.5 mol) in diethylether:THF (1:1, 800 ml) was added a solution of 80% sodium hydrosulfite (218 g, 1.0 mol) in water (800 ml) and the mixture was stirred for 30 minutes. The organic layer was separated, washed with saturated brine (800 ml), and then dried over anhydrous sodium sulfate. The organic layer was purified by silica gel chromatography with a small amount of silica gel and eluted with THF. The solvent was removed under reduced pressure to obtain 68.9 g as a yellow solid. The crystals were dissolved in ethanol (700 ml). To the solution were added dimethyl sulfate (189 ml, 2.0 mol) and 80% sodium hydrosulfite (21.8 g, 0.1 mol), and then added dropwise a 28% solution of sodium methoxide in methanol (482 ml, 2.5 mol) under reflux. After completion of the addition, the mixture was further stirred under reflux for 3 hours and then the solvent was removed under reduced pressure. The residue was poured into ice-cold water (2000 ml) and extracted with ethyl acetate. The organic layer was separated, washed with saturated brine and dried over magnesium sulfate, and then the solvent was removed under reduced pressure. The residue was purified by silica gel chromatography with a small amount of silica gel and eluted with ethyl acetate:hexane (1:4), and the solvent was removed under reduced pressure.

Crystallization from hexane resulted in 54.9 g of the title compound.

Yield: 66%.

Melting point: 108–110° C.

$^1$H-NMR (DMSO-d$_6$) δ 2.20 (6H, s), 3.78 (6H, s), 6.65 (2H, s).

Reference Example 11

2,5-Dimethoxy-3,6-dimethylbenzyl alcohol

To a solution of 2,5-dimethoxy-1,4-dimethylbenzene (33.2 g, 0.2 mol) and dichloromethyl methyl ether (21.7 ml, 0.24 mol) in dichloromethane (800 ml) was added dropwise titanium tetrachloride (32.9 ml, 0.3 mol) with cooling on ice over 30 minutes. After stirring for 1 hour at the same temperature, the reaction mixture was poured into an ice water (500 ml). The organic layer was separated, dried over sodium sulfate, purified by silica gel chromatography with a small amount of silica gel, and eluted with dichloromethane. The solvent was removed under reduced pressure, and crystallization from hexane yielded 29.1 g of an aldehyde form as crude crystals. The resultant crystals were dissolved in ethanol (30 ml) and sodium borohydride (2.72 q, 0.072 mol) was portionwise added at 0° C. After stirring at room temperature for 1 hour, the mixture was cooled to 0° C., and the excessive sodium borohydride was quenched with concentrated hydrochloric acid. The mixture was extracted with ethyl acetate and the organic layer was washed with saturated brine, dried over sodium sulfate, and then the solvent was removed under reduced pressure. The residue was dissolved in THF and dried over sodium sulfate, and then the solvent was removed under reduced pressure. The resultant residue was crystallized from diisopropyl ether-hexane to obtain 23.9 g of the title compound.

Yield: 41%.

$^1$H-NMR (CDCl$_3$) δ 2.04 (1H, t, J=5.8 Hz), 2.23 (3H, s), 2.29 (3H, s), 3.75 (3H, s), 3.79 (3H, s), 4.75 (2H, d, J=5.8 Hz), 6.64 (1H, s).

Reference Example 12

(2,5-Dimethoxy-3,6-dimethylbenzene)acetonitrile

To a solution of 2,5-dimethoxy-3,6-dimethylbenzyl alcohol (23.6 g, 0.12 mol) in THF (250 ml) was added dropwise phosphorus tribromide (5.7 ml, 0.06 mol) at 0° C., the mixture was stirred at room temperature for 2 hours, and then the solvent was removed under reduced pressure. The residue was diluted with ethyl acetate (250 ml), and washed with a saturated aqueous solution of sodium bicarbonate. The organic layer was dried over sodium sulfate and concentrated under reduced pressure to obtain 32.4 g of 2,5-dimethoxy-3,6-dimethylbenzyl bromide. The resultant bromide was dissolved in acetonitrile (50 ml) and added dropwise to a solution of sodium cyanide (7.35 g, 150 mmol) in water (75 ml) and acetonitrile (75 ml), and the mixture was stirred at room temperature for 3 days. The organic layer was separated, washed with saturated brine, and dried over magnesium sulfate. It was purified by silica gel chromatography with a small amount of silica gel and eluted with ethyl acetate, and the solvent was removed under reduced pressure. The residue was suspended in hexane, and crystals were filtered to obtain 23.5 g of the title compound.

Yield: 95%.

$^1$H-NMR (CDCl$_3$) δ 2.23 (3H, s), 2.30 (3H, s), 3.72 (2H, s), 3.75 (3H, s), 3.80 (3H, s), 6.66 (1H, s).

Reference Example 13

2,5-Dimethoxy-3,6-dimethylbenzene ethanamine (2,5-Dimethoxy-3,6-dimethylbenzene)acetonitrile (23.4 g, 114 mmol) was dissolved in a saturated ammonia ethanol solution (250 ml) and then Raney nickel catalyst (25 g) was added. The mixture was reduced by stirring for 3 hours at 50° C. under hydrogen atmosphere at the pressure of 5.5 atms. The catalyst was removed by filtration, and the filtrate was concentrated under reduced pressure to obtain 22.1 g of the title compound as an oil.

Yield: 93%.

$^1$H-NMR (CDCl$_3$) δ 1.44 (2H, br), 2.16 (3H, s), 2.28 (3H, s), 2.83 (4H, m), 3.68 (3H, s), 3.78 (3H, s), 6.55 (1H, s).

Reference Example 14

2,3-Dihydro-4,7-dimethyl-1H-indol-5-ol

To a solution of 2,5-dimethoxy-3,6-dimethylbenzene ethanamine (22.0 g, 105 mmol) in acetonitrile (100 ml) was added dropwise a solution of cerium diammonium nitrate (120.9 g, 220 mmol) in acetonitrile (100 ml) and water (200 ml) with cooling on ice over 20 minutes. After stirring at room temperature for 1 hour, the reaction mixture was poured into a mixture of a solution of sodium hydrogen carbonate (138 g, 1640 mmol) in water (400 ml) and ethyl acetate (400 ml) and stirred at the same temperature for 30 minutes. After removing of insolubles by filtration, the organic layer was separated. The aqueous layer was extracted with ethyl acetate and the organic layers were combined. The combined organic layers were washed with saturated brine, and then treated with a solution of 80% sodium hydrosulfite (48 g, 220 mmol) in water (400 ml). The mixture was made basic using a saturated aqueous solution of sodium hydrogen carbonate, and then extracted with ethyl acetate. The extract was washed with saturated brine, dried over sodium sulfate, purified by silica gel chromatography with a small amount of silica gel and eluted with ethyl acetate. The solvent was removed under reduced pressure, and the resultant oil was crystallized front diethyl ether to obtain 14.4 g of the title compound.

Yield: 84%.

Melting point: 155–158° C.

$^1$H-NMR (CDCl$_3$) δ 2.05 (3H, s), 2.10 (3H, s), 2.94 (2H, t, J=7.4 Hz), 3.05 (1H, br), 3.53 (2H., t, J=7.4 Hz), 6.39 (1H, s), 7.40 (1H, br).

Reference Example 15

2,3-Dihydro-5-hydroxy-4,7-dimethyl-1H-indole-1-carbaldehyde

Acetic anhydride (25 ml, 264 mmol) was added at room temperature to formic acid (75 ml) and stirred for 30 minutes. To the solution, 2,3-dihydro-4,7-dimethyl-1H-indol-5-ol (14.4 g, 88 mmol) was added and the mixture was stirred for 2 hours. The reaction mixture was concentrated under reduced pressure, and the residue was dissolved in a chloroform methanol solution and washed: with a saturated aqueous solution of sodium hydrogen carbonate. The organic layer was washed with saturated brine and dried over sodium sulfate, and then the solvent was removed under reduced pressure. The resultant residue was washed with diisopropyl ether to obtain 6.2 g of the title compound.

Yield: 37%.

Melting point: 239–241° C.

$^1$H-NMR (CDCl$_3$) δ 2.10 (3H, s), 2.33 (3H, s), 2.97 (2H, t, J=8.1 Hz), 4.09 (2H, t, J=8.1 Hz), 6.53 (1H, s), 8.38 (1H, br), 8.85 (1H, s).

Reference Example 16

2,3-Dihydro-4,7-dimethyl-5-[(2-methyl-2-propenyl)oxy]-1H-indole-1-carbaldehyde 2,3-Dihydro-5-hydroxy-4,7-dimethyl-1H-indole-1-carbaldehyde (5.74 g, 30 mmol) was dissolved in N,N-dimethylformamide (100 ml) and to the solution were added potassium carbonate (8.29 g, 60 mmol), potassium iodide (0.50 g, 3 mmol) and 3-chloro-2-methyl-1-propene (4.41 ml, 45 mmol). The mixture was stirred at 80° C. for 3 hours. The reaction mixture was poured into cold water (300 ml), and extracted with ethyl acetate. The extract was washed with saturated brine and dried over sodium sulfate, and then the solvent was removed under reduced pressure. The residue was purified by column chromatography on silica gel. (hexane:ethyl acetate=6:1) to obtain 6.00 g of the title compound.

Yield: 82%.

$^1$H-NMR (CDCl$_3$) δ 1.85 (3H, s), 2.14 (3H, s), 2.39 (3H, s), 2.99 (2H, t, J=8.0 Hz), 4.11 (2H, t, J=8.0 Hz), 4.40 (2H, s), 4.99 (1H, s), 5.11 (1H, s), 6.48 (1H, s), 8.89 (1H, s).

Reference Example 17

2,3-Dihydro-5-hydroxy-4,7-dimethyl-6-(2-methyl-2-propenyl)-1H-indole-1-carbaldehyde 2,3-Dihydro-5-hydroxy group-4,7-dimethyl-6-(2-methyl-2-propenyl)-1H-indole-1-carbaldehyde 2,3-Dihydro-4,7-dimethyl-5-[(2-methyl-2-propenyl)oxy]-1H-indole-1-carbaldehyde (6.00 g, 24.4 mmol) was suspended in N,N-dimethylaniline (25 ml) and stirred under argon atmosphere at 220° C. for 7 hours. The reaction mixture was cooled and diluted with hexane (50 ml) and stirred for 30 minutes. The precipitated crystals were filtered and washed with hexane to obtain 5.45 g of the title compound.

Yield: 91%.

Melting point: 132–134° C.

$^1$H-NMR (CDCl$_3$) δ 1.82 (3H, s), 2.15 (3H, s), 2.29 (3H, s), 2.97 (2H, t, J=7.9 Hz), 3.39 (2H, S), 4.14 (2H, t, J=7.9 Hz), 4.62 (1H, s), 4.88 (1H, s), 5.00 (1H, s), 8.75 (1H, s).

Reference Example 18

2-(tert-Butyl)-4-nitroso-5-methylphenol

To a solution of 2-(tert-butyl)-5-methylphenol (32.9 g, 0.2 mol) in water:ethanol (300 ml, 2:1) was added concentrated hydrochloric acid (20 ml, 0.24 mol) and then cooled to 0° C. To the solution was added dropwise a solution of sodium nitrite (14.5 g, 0.21 mol) in water (40 ml) over 30 minutes. After completing the dropwise addition, the mixture was stirred at the same temperature for 2 hours. The precipitated crystals were collected by a filtration, and washed with a cold water. The resultant crystal was dissolved in an ethyl acetate:THF (9:1) solution, washed with saturated brine, dried over sodium sulfate, and purified by silica gel column chromatography on a small amount of silica gel which was eluted with ethyl acetate. After the solvent was removed under reduced pressure, the residue was suspended in hexane and the crystals were collected by filtration to obtain 31.4 g of the title compound.

Yield: 81%.

Melting point: 181–182° C.

$^1$H-NMR (CDCl$_3$) δ 1.28 (9H, s), 2.17 (3H, d, J=1.3 Hz), 2.45 (2H, br), 6.18 (1H, d, J=1.3 Hz), 7.64 (1H, s).

Reference Example 19
4-Amino-2-(tert-butyl)-5-methylphenol

To a solution of 2-(tert-butyl)₄-nitroso-5-methylphenol (47.0 g, 243 mmol) in ethanol (500 ml) was slowly added dropwise hydrazine hydrate (29.5 ml, 608 mmol) at 0° C. After completing the dropwise addition, the mixture was stirred at room temperature for 16 hours, and the solvent was removed under reduced pressure. The residue was combined with water (500 ml), and the crystals were filtered. The crystals were dissolved in ethyl acetate, washed with saturated brine, dried over sodium sulfate and purified by silica gel column chromatography on a small amount of silica gel which was eluted with ethyl acetate. After the solvent was removed under reduced pressure, the residue was suspended in hexane and the crystals were collected by filtration to obtain 39.3 g of the title compound.

Yield: 90%.
Melting point: 191–192° C.
$^1$H-NMR (CDCl$_3$) δ 1.37 (9H, s), 2.07 (3H, s), 3.25 (2H, br), 6.52 (1H, s), 6.60 (1H, s), 7.35 (1H, br).

Reference Example 20
N-[5-(tert-Butyl)-4-hydroxy-2-methylphenyl]formamide According to the same manner as that of Reference Example 16, 25.5 g of the title compound was obtained using N-[5-(tert-butyl)-4-hydroxy-2-methylphenyl]formamide (35.2 g, 0.17 mol).

Yield: 57%.
Melting point: 108–109° C.

Reference Example 22
N-[5-(tert-Butyl)-4-hydroxy-2-methyl-3-(2-methyl-2-propenyl)phenyl]formamide According to the same manner as that of Reference Example 16, 25.5 g of the title compound was obtained using N-[5-(tert-butyl)-4-hydroxy group-2-methylphenyl]formamide (35.2 g, 0.17 mol).

Yield: 57%.
Melting point: 108–109° C.

Reference Example 22
N-[5-(tert-Butyl)-4-hydroxy group-2-methyl-3-(2-methyl-2-propenyl)phenyl]formamide According to the same manner as that of Reference Example 17, 20.9 g of the title compound was obtained using N-[5-(tert-butyl)-2-methyl-4-(2-methyl-2-propenyloxy)phenyl]formamide (25.4 g, 97.2 mmol).

Yield: 82%.
Melting point: 153–154° C.

Reference Example 23
5-Amino-7-(tert-butyl)-2,3-dihydro-2,2,4-trimethyl-1-benzofuran To a solution of N-[5-(tert-butyl)₄-hydroxy-2-methyl-3-(2-methyl-2-propenyl)phenyl]formamide (10.45 g, 40 mmol) in methanol (100 ml) was added concentrated hydrochloric acid (40 ml) and the mixture was heated under reflux for 3 hours under argon atmosphere. After cooling to 0° C., the mixture was made weakly basic using 12N sodium hydroxide, and extracted with ethyl acetate. The organic layer was washed with saturated brine and dried over sodium sulfate, and then the solvent was removed under reduced pressure. The residue was purified by a column chromatography on a silica gel (hexane:ethyl acetate=1:1) and crystallized from hexane to obtain 6.28 g of the title compound.

Yield: 67%.
Melting point: 115–116° C.
$^1$H-NMR (CDCl$_3$) & 1.31 (9H, s), 1.44 (6H, s,), 2.02 (3H, s), 2.87 (2H, s), 2.95 (2H, br), 6.47 (1H, s).

Reference Example 24
tert-butyl N-[7-(tert-butyl)-2,3-dihydro-2,2,4-trimethyl-1-benzofuran-5-yl]carbamate 5-Amino-7-(tert-butyl)-2,3-dihydro-2,2,4-trimethyl-1-benzofuran (6.30 g, 27 mmol) was dissolved in THF (63 ml) and then triethylamine (5.65 ml, 40.5 mmol) was added. After cooling to 0° C., di-tert-butyl dicarbonate (6.48 g, 29.7 mmol) was added to the solution, and the mixture was stirred for 3 hours at room temperature. The reaction mixture was poured into cold water (100 ml), and extracted with diethyl ether. The organic layer was washed with saturated brine, dried over sodium sulfate and purified by silica gel column chromatography on a small amount of silica gel which was eluted with hexane:ethyl acetate (7:3). The resultant oil was the title compound (7.30 g).

Yield: 81%.
Melting point: 124–126° C.
$^1$H-NMR (CDCl$_3$) δ 1.31 (9H, s), 1.45 (6H, s), 1.50 (9H s), 2.07 (3H, s), 2.88 (2H, s), 5.97 (1H, br), 7.06 (1H, s).

Reference Example 25
7-(tert-Butyl)-2,3-dihydro-5-(2-methyl-2-propenyl)amino-2,2,4-trimethyl-1-benzofuran tert-Butyl N-[7-(tert-butyl)-2,3-dihydro-2,2,4-trimethyl-1-benzofuran-5-yl]carbamate (7.17 g, 21.5 mmol) was dissolved in N,N-dimethylformamide (72 ml), and sodium hydride (0.62 g, 25.8 mmol) which had been washed with hexane was added at 0° C. carefully. After stirring at room temperature for 30 minutes, 3-chloro-2-methyl-1-propene (2.53 ml, 25.8 mmol) and potassium iodide (0.36 g, 2.2 mmol) were added and the mixture was stirred at the same temperature for 1 hour. The reaction mixture was washed with saturated brine and dried over sodium sulfate, and the solvent was removed under reduced pressure. The residue was purified by a column chromatography on a silica gel (hexane:ethyl acetate=4:1). The resultant oil was dissolved in methanol (85 ml), combined with concentrated hydrochloric acid (8.5 ml), and stirred under argon atmosphere at 50° C. for 2 hours. After cooling to 0° C., the mixture was made weakly basic using a 3N aqueous solution of sodium hydroxide, and extracted with ethyl acetate. The organic layer was washed with saturated brine, dried over sodium sulfate, and the solvent was removed under reduced pressure, and then crystallized from a cold hexane to obtain 6.20 g of the title compound.

Yield: 100%.
Melting point: 164–16–5° C.
$^1$H-NMR (CDCl$_3$) δ 1.32 (9H, s), 1.43 (6H, s), 1.82 (0.3H, s), 2.02 (3H, s), 2.88 (2H, s), 3.67 (2H, s), 4.90 (1H, s), 5.01 (1H, s), 6.41 (1H, s).

Reference Example 26
1,4-Dimethoxy-2,5-dimethyl-3-(2-nitro-1-propenyl)benzene A mixture of 2,5-dimethoxy-3,6-dimethyl-benzaldehyde (4.0 g, 20 mmol), ammonium acetate (1 g, 13 mmol) and nitroethane (25 ml) was heated under reflux for 4 hours. The reaction mixture was diluted with diisopropyl ether, washed with water and saturated brine, dried over magnesium sulfate, filtered and concentrated under reduced pressure. The residue was purified by column chromatography on silica gel (hexane:isopropyl ether=95:5) and then recrystallized from methanol to obtain 5.1 g of the title compound.

Yield: 99%.
Melting point: 48–49° C.

Reference Example 27
1-(2,5-Dimethoxy-3,6-dimethylphenyl)-2-propanamine

To a solution of 1,4-dimethoxy-2,5-dimethyl-3-(2-nitro-1-propenyl)benzene (5.0 g, 19.9 mmol) in tetrahydrofuran (100 ml) was added lithium aluminum hydride (4.0 g, 105.4 mmol) with cooling on ice, and the reaction mixture was heated under reflux for 6 hours. To the reaction mixture was added HIFLO-SUPERCEL (trade name) (5 g), and then water was added dropwise (1.5 ml) with cooling on ice. The resultant mixture was suspended in ethyl acetate, filtered and concentrated under reduced pressure to obtain 4.2 g of the desired product as an oil.

Yield: 95%.

$^1$H-NMR (CDCl$_3$) δ 1.12 (3H, d, J=6.4 Hz), 1.50 (2H, br s), 2.15 (3H, s), 2.29 (3H, s), 2.67 (1H, dd, J=13.2 and 7.6 Hz), 2.70 (1H, dd, J=13.2, 5.8 Hz), 3.11 (1H, m), 3.65 (3H, s), 3.78 (3H, s), 6.56 (1H, s).

Reference Example 28
2,3-Dihydro-5-hydroxy-2,4,7-trimethyl-1H-indole

To the solution of 1-(2,5-dimethoxy-3,6-dimethylphenyl)-2-propanamine (2.2 g, 9.4 mmol) in acetonitrile (10 ml) was added dropwise a solution of cerium (IV) diammonium nitrate (10.0 g, 18.2 mmol) in acetonitrile (20 ml) and water (20 ml) with cooling on ice, and stirred at room temperature for 2 hours. The reaction mixture was diluted with water, neutralized with sodium hydrogen carbonate, and extracted three times with ethyl acetate. The organic layers were combined, washed with water and saturated brine, dried over magnesium sulfate, filtered and concentrated under reduced pressure to obtain a solid. The solid was dissolved in ethyl acetate, combined with an aqueous solution of sodium hydrosulfite and shaken to precipitate a solid, which was collected by filtration to obtain 1.2 g of the title compound.

Yield: 68%.

Melting point: 196–197° C.

Reference Example 29
1-Acetyl-2,3-dihydro-5-hydroxy group-2,4,7-trimethyl-1H-indole To a solution of 2,3-dihydro-5-hydroxy-2,4,7-trimethyl-1H-indole (1.0 g, 5.7 mmol) in pyridine (2.6 ml) was added acetic anhydride (1.7 ml, 16.6 mmol), and stirred at room temperature for 3 hours. Ice was added to the reaction mixture and the product was extracted with ethyl acetate. The extract was washed with water, dried and concentrated, and the residue was dissolved in methanol (30 ml). To the solution was added a solution of potassium carbonate (1.0 g, 7.2 mmol) in water (15 ml), and the reaction mixture was stirred at room temperature for 30 minutes. The reaction mixture was neutralized with 1N hydrochloric acid, and the product was extracted with ethyl acetate. The extract was washed with water and saturated brine, dried over magnesium sulfate, filtered and concentrated under reduced pressure. The residue was recrystallized from ethyl acetate-isopropyl ether to obtain 0.89 g of the title compound.

Yield: 76%.

Melting point: 156–158° C.

Reference Example 30
1-Acetyl-2,3-dihydro-2,4,7-trimethyl-5-[(2-methyl-2-propenyl)oxy]-1H-indole A suspension of 1-acetyl-2,3-dihydro-5-hydroxy-2,4,7-trimethyl-1H-indole (3.3 g, 16.1 mmol), 3-chloro-2-methyl-1-propene (2.6 g, 28.7 mmol) and potassium carbonate (3.5 g, 25.3 mmol) in dimethylformamide (25 ml) was stirred for 20 hours at 80° C. under nitrogen atmosphere. The reaction mixture was combined with water, and extracted twice with ethyl acetate. The organic layers were combined, washed with water and saturated brine, dried over magnesium sulfate, filtered and concentrated under reduced pressure. The residue was purified by column chromatography on silica gel (hexane:ethyl acetate=3:1) to obtain 3.8 g of the title compound.

Yield: 91%.

Oil.

$^1$H-NMR (CDCl$_3$) δ 1.23 (3H, d, J=6.4 Hz), 1.84 (3H, s), 2.11 (3H, s), 2.21 (6H, s), 2.42 (1H, d, J=15.6 Hz), 3.25 (1H, dd, J=15.6, 7.8 Hz), 4.38 (2H, s), 4.60 (1H, m), 4.97 (1H, m), 5.11 (1H, m), 6.51 (1H, s).

Reference Example 31
1-Acetyl-2,3-dihydro-5-hydroxy-2,4,7-trimethyl-6-(2-methyl-2-propenyl)-1H-indole A solution of 1-acetyl-2,3-dihydro-2,4,7-trimethyl-5-[(2-methyl-2-propenyl)oxy]-1H-indole (3.8 g, 14.7 mmol) in N,N-diethylaniline (30 ml) was stirred for 2 hours at 200° C. under nitrogen atmosphere. The reaction mixture was diluted with diethyl ether, and washed with 1N hydrochloric acid, water and saturated brine. The organic layer was dried over magnesium sulfate, filtered and concentrated under reduced pressure to obtain 3.5 g of the title compound as an oil.

Yield: 92%.

$^1$H-NMR (CDCl$_3$) δ 1.23 (3H, d, J=7.0 Hz), 1.80 (3H, s), 2.08 (3H, s), 2.11 (6H, s), 2.20 (2H, m), 2.40 (1H, d, J=15.8 Hz), 3.25 (1H, dd, J=15.8, 7.8 Hz), 3.38 (2H, s), 4.60 (1H, m), 4.68 (1H, m), 4.86 (1H, m), 5.07 (1H, s).

Reference Example 32
8-Methyl-5-(1-methylethyl)-2-phenyl-4H-1,3,2-benzodioxaborin Isothymol (46 ml, 0.3 mol), benzeneboric acid (38.4 g, 0.315 mol) and paraformaldehyde (purity: 75%, 14.4 g, 0.36 mol) were suspended in toluene (500 ml), and to this was added propionic acid (2.23 ml, 0.03 mol). The mixture was heated under reflux for 1.5 hours with removal of the generated water using a Dean-Stark trap. Paraformaldehyde (purity: 75%, 14.4 g, 0.36 mol) was added again, and the mixture was heated under reflux for further 1.5 hours. The reaction mixture was concentrated under reduced pressure, and the residue was purified by column chromatography on silica gel (ethyl acetate:hexane=1:9) to obtain 72.1 g of the title compound as an oil.

Yield: 90%.

$^1$H-NMR (CDCl$_3$) δ 1.21 (6H, d, J=6.6 Hz), 2.37 (3H, s), 2:70–2.86 (1H, m), 5.29 (2H, s), 6.90 (1H, d, J=8.1 Hz), 7.09 (1H, d, J=8.1 Hz), 7.37–7.53 (3H, m), 7.96–8.01 (2H, m).

Reference Example 33
2-Hydroxymethyl-6-methyl-3]-methylethyl)phenol

In a solution of 8-methyl-5-(1-methylethyl)-2-phenyl-4H-1,3,2-benzodioxaborin (72.1 g, 0.27 mol) in toluene (500 ml) was added diethanolamine (259 ml, 2.7 mol), and stirred for 16 hours at 100° C. The reaction mixture was concentrated under reduced pressure, and the residue was poured into cooled 3N hydrochloric acid (1000 ml), and extracted with ethyl acetate. The extract was washed with saturated brine, dried over sodium sulfate, and concentrated under reduced pressure. The residue was purified by column chromatography on silica gel (ethyl acetate:hexane=1:4) to obtain 37.4 g of the title compound as an oil.

Yield: 77%.

$^1$H-NMR (CDCl$_3$) δ1.20 (6H, d, J=6.6 Hz), 2.21 (3H, s), 2.95–3.13 (1H, m), 4.94 (2H, s), 5.18 (1H, br), 6.75 (1H, d, J=8.0 Hz), 7.05 (1H, d, J=8.0 Hz).

Reference Example 34
3-Methyl-6-(1-methylethyl)-2-methoxybenzyl alcohol

2-Hydroxymethyl-6-methyl-3-(1-methylethyl)phenol (37.3 g, 207 mmol) was dissolved in THF (350 ml), and then potassium tert-butoxide (22.1 g, 197 mmol) was added. To the mixture was added methyl iodide (19.7 ml, 311 mmol) at 0° C., and the mixture was stirred at room temperature for 16 hours. The reaction mixture was combined with water, made acidic with 1N hydrochloric acid, and extracted with ethyl acetate. The extract was washed with saturated brine, dried over sodium sulfate and purified by column chromatography on a small amount of silica gel which was eluted with ethyl acetate. The solvent was concentrated under reduced pressure, and the residue was crystallized from hexane to obtain 21.7 g of the title compound.

Yield: 54%.
Melting point: 100–101° C.
$^1$H-NMR (CDCl$_3$) δ 1.24 (6H, d, J=6.6 Hz), 2.11 (1H, t, J=6.2 Hz), 2.28 (3H, s), 3.18–3.36 (1H, m), 3.81 (3H, s), 4.78 (2H, d, J=6.2 Hz), 7.01 (1H, d, J=8.0 Hz), 7.14 (1H, d, 3=8.0 Hz).

Reference Example 35
3-Methyl-6-(1-methylethyl)-2-methoxybenzyl bromide

To a solution of 3-methyl-6-(1-methylethyl)-2-methoxybenzyl alcohol (15.9 g, 80 mmol) in THF (160 ml) was added phosphorus tribromide (3.80 ml, 40 mmol) at 0° C. and the mixture was stirred at room temperature for 2 hours. The reaction mixture was washed with saturated brine, dried over sodium sulfate and concentrated under reduced pressure. The residue was purified by column chromatography on silica gel (ethyl acetate:hexane=1:4) to obtain 21.7 g of the title compound as an oil.

Yield: 100%.
$^1$H-NMR (CDCl$_3$) δ 1.26 (6H, d, J=6.6 Hz), 2.27 (3H, s), 3.18–3.38 (1H, m), 3.88 (3H, s), 4.71 (2H, s), 6.99 (1H, d, J=8.0 Hz), 7.14 (1H, d, J=8.0 Hz).

Reference Example 36
[3-Methyl-6-(1-methylethyl)-2-methoxybenzene]acetonitrile To a solution of 3-methyl-6-(1-methylethyl)-2-methoxybenzyl bromide (21.7 g, 80 mmol) in acetonitrile (30 ml) was added a solution of sodium cyanide (4.90 g, 100 mmol) in acetonitrile:water (1:1, 100 ml) at 0° C. and stirred at room temperature for 36 hours. The organic layer was separated, washed with saturated brine, and dried over sodium sulfate. The solvent was removed under reduced pressure, and the residue was purified by column chromatography on silica gel (ethyl acetate:hexane=1:9) to obtain 14.6 g of the title compound.

Yield: 90%.
Melting point: 37.5–39° C.
$^1$H-NMR (CDCl$_3$) δ 1.26 (6H, d, J=7.0 Hz), 2.29 (3H, s), 2.99–3.19 (1H, m), 3.78 (2H, s), 3.82 (3H, s), 7.01 (1H, d, J=8.0 Hz), 7.15 (1H, d, J=8.0 Hz).

Reference Example 37
2-[3-Methyl-6-(1-methylethyl)-2-methoxybenzene]ethanamine

[3-Methyl-2-methoxy-6-(1-methylethyl)benzene]acetonitrile (17.5 g, 86 mmol) was dissolved in ethanol (200 ml), and the mixture was reduced at 60° C. using a Raney nickel catalyst (20 g) under hydrogen atmosphere at the pressure of 3 atms. The catalyst was removed by filtration, and the filtrate was concentrated under reduced pressure. The residue was diluted with diethyl ether, washed with saturated brine, and dried over sodium sulfate. The solvent was removed under reduced pressure to obtain 17.3 g of the title compound as an oil.

Yield: 97%.
$^1$H-NMR (CDCl$_3$) δ 1.21 (6H, d, J=6.8 Hz), 1.38 (2H, br), 2.27 (3H, s), 2.86 (4H, br), 3.01–3.20 (1H, m), 3.73 (3H, s), 6.96 (1H, d, J=8.0 Hz), 7.04 (1H, d, J=8.0 Hz).

Reference Example 38
N-[3-Methyl-6-(1-methylethyl)-2-methoxybenzene]ethyl trifluoroacetamide 2-[3-Methyl-2-methoxy-6-(1-all methylethyl)benzene]ethanamine (19.5 g, 94 mmol) and triethylamine (17.0 ml, 122.2 mmol) were dissolved in THF (200 ml) and then trifluoroacetic anhydride (14.3 ml, 103.4 mmol) was added at 0° C. After stirring at room temperature for 3 hours, the mixture was poured into a cold water, and extracted with ethyl acetate. The extract was washed with saturated brine, dried over sodium sulfate, and concentrated under reduced pressure. The residue was purified by column chromatography on silica gel (ethyl acetate:hexane=1:4) to obtain 26.0 g of the title compound.

Yield: 91%.
Melting point: 100–100.5° C.
$^1$H-NMR (CDCl$_3$) δ 1.22 (6H, d, J=7.0 Hz), 2.28 (3H, s), 2.98 (2H, t, J=6.3 Hz), 3.00–3.17 (1H, m), 3.44–3.54 (2H, m), 3.77 (3H, s), 7.01 (1H, d, J=8.1 Hz), 7.51 (1H, d, J=8.1 Hz).

Reference Example 39
N-[6-Methyl-3-(1-methylethyl)-1,4-benzoquinon-2-yl]ethyl trifluoroacetamide To a solution of N-[3-Methyl-2-methoxy-6-(1-methylethyl)benzene]ethyl trifluoroacetamide (26.0 g, 85.7 mmol) in acetic acid (130 ml) was added a solution of chromic anhydride (42.9 g, 429 mmol) in water (43 ml) at 0° C. After stirring at room temperature for 12 hours, the mixture was diluted with a cold water (250 ml), and extracted with ethyl acetate. The extract was washed with saturated brine, dried over sodium sulfate and purified by column chromatography on a small amount of silica gel which was eluted with ethyl acetate. The solvent was removed under reduced pressure, and then the residue was crystallized from hexane to obtain 10.4 g of the title compound.

Yield: 40%.
Melting point: 94–95° C.
$^1$H-NMR (CDCl$_3$) δ 1.31 (6H, d, J=7.0 Hz), 2.02 (3H, d, J=1.6 Hz), 2.83 (2H, t, J=6.6 Hz), 2.93–3.13 (1H, m), 3.46 (2H, q, J=6.6), 6.50–6.55 (1H, m), 6.82 (1H, br).

Reference Example 40
4-Methoxy-2,5-dimethylaniline 2,5-Dimethylnitrobenzene, (46.8 ml, 0.35 mol) was dissolved in sulfuric acid (47.1 ml)/methanol (650 ml) and then 5% palladium on carbon (50% hydrate, 0.35 g) was added. The mixture was allowed to react for 3 hours under hydrogen atmosphere at the pressure of 5 atms at 40° C. After cooling, the catalyst was removed, and methanol was removed under reduced pressure. The residue was poured into a 25% aqueous ammonia solution with cooling on ice, and extracted with toluene. The extract was washed with 5% sodium hydrosulfite, dried over sodium sulfate and purified by column chromatography on a small amount of silica gel (toluene:ethyl acetate=1:1). The solvent was removed under reduced pressure and crystallization from hexane yielded 35.0 g of the title compound.

Yield: 66%.
Melting point: 75–76° C.

¹H-NMR (CDCl₃) δ 2.15 (6H, s), 3.29 (2H, br); 3.76 (3H, s), 6.51 (1H, s), 6.58 (1H, s).

Reference Example 41
4,7-Dimethyl-5-methoxy-3-(methylthio)-1,3-dihydro-2H-indol-2-one To a solution of methyl (methylthio)acetate (14.8 ml, 115 mmol) in dichloromethane (400 ml) was added sulfuryl chloride (9.64 ml, 120 mmol) at −78° C. and stirred for 15 minutes. To the mixture was added dropwise a solution of 4-methoxy-2,5-dimethylaniline (15.1 g, 100 mmol) and proton sponge (22.5 g, 105 mmol) in dichloromethane (100 ml) over 1 hour and the mixture was stirred at the same temperature for 1 hour. Then, triethylamine (15.3 ml, 110 mmol) was added, and the mixture was allowed to warm to room temperature slowly. After stirring at room temperature for 1 hour, water was added and the precipitated crystals were collected by filtration and washed with dichloromethane and water to obtain 18.3 g of the title compound.

Yield: 77%.
Melting point: 226–227° C.
¹H-NMR (CDCl₃) δ 2.04 (3H, s), 2.24 (3H, s), 2.26 (3H, s), 3.79 (3H, s), 4.20 (1H, s), 6.55 (1H, s), 8.40 (1H, brs).

Reference Example 42
4,7-Dimethyl-5-methoxy-1,3-dihydro-2H-indol-2-one

To a solution of 4,7-dimethyl-5-methoxy-3-(methylthio)-1,3-dihydro-2H-indol-2-one (17.8 g, 75 mmol) in dichloromethane (350 ml) were added triphenylphosphine (23.6 g, 90 mmol) and toluenesulfonic acid monohydrate (17.1 g, 90 mmol) at room temperature and stirred for 3 hours. The reaction mixture was poured into a cold water, and the precipitated crystals were collected by filtration. After washing with dichloromethane and water, 12.4 g of the title compound was obtained.

Yield: 87%.
Melting point: 262–263° C.
¹H-NMR (CDCl₃) δ 2.10 (3H, s), 2.26 (3H, s), 3.44 (2H, s), 3.79 (3H, s), 6.52 (1H, s), 8.85 (1H, brs).

Reference Example 43
4,7-Dimethyl-5-methoxy-1,2-dihydro-1H-indole

To a solution of 4,7-dimethyl-5-methoxy-1,3-dihydro-2H-indol-2-one (13.4 g, 70 mmol) in THF (134 ml) was added dropwise 1M borane THF complex salt (280 ml, 280 mmol) at 0° C. and then stirred at 60° C. for 3 hours. After cooling on ice, water (100 ml) was added dropwise. After THF was removed under reduced pressure, concentrated hydrochloric acid (100 ml) was added to the residue and the mixture was stirred at 60° C. for 2 hours. With cooling on ice, the mixture was neutralized with 12N sodium hydroxide and extracted with ethyl acetate. The organic layer was washed with saturated brine, dried over sodium sulfate and purified by column chromatography on a small amount of silica gel (ethyl acetate). The solvent was removed under reduced pressure and a crystallization from hexane yielded 8.18 g of the title compound.

Yield: 66%.
Melting point: 71–72° C.
¹H-NMR (CDCl₃) δ 2.10 (3H, s), 2.12 (3H, s), 2.97 (2H, t, J=8.3 Hz), 3.56 (2H, t, J=8.3 Hz), 3.76 (3H, s), 6.43 (1H, s).

Reference Example 44
4,7-Dimethyl-1,2-dihydro-1H-indol-5-ol 4,7-Dimethyl-5-methoxy-1,2-dihydro-1H-indole (8.15 g, 46 mmol) was dissolved in acetic acid (92 ml), combined with 48% hydrobromic acid (46 ml) and stirred for 5 hours under reflux. Acetic acid was removed under reduced pressure, and the residue was poured into a cold saturated aqueous solution of sodium bicarbonate. The mixture was extracted with ethyl acetate, and the organic layer was washed with saturated brine, dried over sodium sulfate and purified by column chromatography on a small amount of silica gel (hexane:ethyl acetate=1:1). The solvent was removed under reduced pressure and crystallization from ether yielded 4.66 g of the title compound.

Yield: 62%.
Melting point: 153–155° C.
¹H-NMR (CDCl₃) δ 1.65 (1H, br), 2.05 (3H, s), 2.12 (3H, s), 2.97 (2H, t, J=8.3 Hz), 3.57 (2H, t, J=8.3 Hz), 6.36 (1H, s).

Reference Example 45
1-Acetyl-4,7-dimethyl-1,2-dihydro-1H-indol-5-ol 4,7-Dimethyl-1,2-dihydro-1H-indol-5-ol (4.57 g, 28 mmol) was added to a solution of 2 N sodium hydroxide (50 ml) and THF (50 ml). To the mixture was added dropwise acetic anhydride (2.91 ml, 30.8 mmol) at 0° C. and warmed to room temperature. The mixture was stirred for 4 hours at the same temperature, the resulting mixture was neutralized with 3N hydrochloric acid, and extracted with ethyl acetate. The organic layer was washed with saturated brine and dried over sodium sulfate, and the solvent was removed under reduced pressure. The residue was purified by column chromatography on silica gel (hexane:ethyl actate=3:2) and the solvent was removed under reduced pressure followed by crystallization from ether yielded 1.35 g of the title compound.

Yield: 23%.
Melting point: 159–160° C.
¹H-NMR (CDCl₃) δ 2.11 (3H, s), 2.18 (3H, s), 2.24 (3H, brs), 2.91 (2H, t, J=7.1 Hz), 4.07 (2H, br), 5.11 (1H; s), 6.45 (1H, s).

Reference Example 46
1-Acetyl-4,7-dimethyl-5-[[2-methyl-3-(4-methylphenyl)-2-propenyl]oxy]-1,2-dihydro-1H-indole To a solution of 1-acetyl-4,7-dimethyl-1,2-dihydro-1H-indol-5-ol (1.33 g, 6.5 mmol) in dimethylformamide (6.7 ml) were added potassium carbonate (1.91 g, 8.5 mmol) and 3-chloro-2-methyl-1-(4-methylphenyl)-1-propene (1.52 q, 8.45 mmol) and stirred for 5 hours at 50° C. under argon atmosphere. The reaction mixture was poured into cold water and extracted with ethyl acetate. The organic layer was washed with saturated brine and dried over sodium sulfate, and the solvent was removed under reduced pressure. The residue was purified by column chromatography on silica gel (hexane:ethyl actate 1:1) and the solvent was removed under reduced pressure and then crystallization from hexane yielded 1.78 g of the title compound.

Yield: 79%.
Melting point: 132–134° C.
¹H-NMR (CDCl₃) δ 1.54 (3H, s), 2.15 (3H, s), 2.24 (6H, br), 2.36 (3H, s), 2.93 (2H; t, J=7.2 Hz), 4.08 (2H, br), 4.52 (2H, 5), 6.57 (1H, s), 6.61 (1H, brs), 7.15, d, J=8.4 Hz), 7.20 (2H, d, J=8.4 Hz).

Example 1
3,5,6,7-Tetrahydro-2,2,4,8-tetramethyl-2H-furo[2,3-f]indole 2,3-Dihydro-5-hydroxy-4,7-dimethyl-6-(2-methyl-2-propenyl)-1H-indole-1-carbaldehyde (491 mg, 2.0 mmol) was dissolved in methanol (6 ml). To the solution was added concentrated hydrochloric acid (6 ml) and stirred for 3 hours with heating under reflux. The reaction mixture was cooled to 0° C., made weakly basic with 12N sodium hydroxide, and extracted with ethyl acetate. The extract was washed with saturated brine and dried over sodium sulfate, and the solvent was removed under reduced pressure. The residue was purified by column chromatography on silica gel (hexane:ethyl acetate=2:1) and crystallized from hexane to obtain 330 mg of the title compound.

Yield: 76%.
Melting point: 105–107° C.
$^1$H-NMR (CDCl$_3$) δ 1.45 (6H, s), 2.01 (3H, s), 2.08 (3H, s), 2.45 (1H, br), 2.89 (2H, s), 2.93 (2H, t, J=8.3 Hz), 3.55 (2H, t, J=8.3 Hz).

Example 2
5-Acetyl-(2,2,4,6,8-pentamethyl-3,5,6,7-tetrahydro-2H-furo[2,3-f]indole To a solution of 1-acetyl-2,3-dihydro-5-hydroxy-2,4,7-trimethyl-6-(2-methyl-2-propenyl)-1H-indole (3.5 g, 13.5 mmol) in methanol (30 ml) was added concentrated hydrochloric acid (10 ml) and heated under reflux for 30 minutes under nitrogen atmosphere. The reaction mixture was diluted with water, and the product was extracted with ethyl acetate. The extract was washed with saturated brine, dried over magnesium sulfate, and concentrated under reduced pressure. The residue was recrystallized from ethyl acetate-isopropyl ether to obtain 2.6 g of the title compound.

Yield: 74%.
Melting point: 154–155° C.

Example 3
2,2,4,6,8-Pentamethyl-3,5,6,7-tetrahydro-2H-furo[2,3-f]indole

To a solution of 5-acetyl-(2,2,4,6,8-pentamethyl-2,3,6,7-tetrahydro-5H-furo[2,3-f]indole (0.5 g, 1.9 mmol) in ethanol (6 ml) was added 5N hydrochloric acid, and heated at 200° C. for 1 hour in an autoclave. After pooling, the reaction mixture was diluted with water, and the product was extracted with ethyl acetate. The extract was washed with water, dried over magnesium sulfate, filtered and concentrated under reduced pressure. The residue was recrystallized from hexane-isopropyl ether to obtain 0.36 g of the title compound.

Yield: 823%.
Melting point: 87–88° C.

Example 4
8-tert-butyl-3,5,6,7-tetrahydro-2,2,4,6,6-pentamethyl-2H-furo[2,3-f]indole hydrochloride 7-tert-butyl-5-(2-methyl-2-propenyl)amino-2,2,4-trimethyl-2,3-dihydrobenzofuran (5.75 g, 20 mmol) was dissolved in xylene (60 ml), combined with zinc chloride (6.82 g, 50 mmol) and heated under reflux for 32 hours under argon atmosphere. The reaction mixture was cooled, and combined with a saturated aqueous solution of sodium acetate (100 ml), and the mixture was extracted with ethyl acetate. The extract was washed with 1N sodium hydroxide and saturated brine and dried over sodium sulfate and the solvent was removed under reduced pressure. The residue was purified by column chromatography on silica gel (hexane:ethyl acetate=4:1) to obtain an oil, which was treated with a 4N hydrochloric acid ethyl acetate solution and crystallized from ethyl acetate to obtain 2.56 g of the title compound.

Yield: 40%.
Melting point: 293–296° C.
NMR data of a free base is shown below.
$^1$H-NMR (CDCl$_3$) δ 1.30 (6H, s), 1.39 (9H, s), 1.42 (6H, s), 1.95 (3H, s), 2.52 (1H, br), 2.81 (2H, s), 3.08 (2H, s).

Example 5
3,5,6,7-Tetrahydro-2-hydroxymethyl-2,4,8-trimethyl-2H-furo[2,3-f]indole-5-carbaldehyde To a solution of 2,3-dihydro-5-hydroxy-4,7-dimethyl-6-(2-methyl-2-propenyl)-14H-indole-1-carbaldehyde (491 mg, 2.0 mmol) in dichloromethane (5 ml) and saturated sodium hydrogen carbonate (2.5 ml) solution was added m-chloroperbenzoic acid (863 mg, 5 mmol) with cooling on ice and stirred for 2 hours at room temperature. Dichloromethane was removed under reduced pressure, and the residue was combined with ethyl acetate (10 ml) and triethylamine (2 ml) and washed with water. To the organic layer was added a 10% aqueous solution of sodium hydrosulfite (10 ml) and shaken, and then the organic layer was separated. The organic layer was washed with a saturated aqueous solution of sodium hydrogen carbonate and saturated brine and dried over sodium sulfate, and then the solvent was removed under reduced pressure. The residue was purified by column chromatography on silica gel (hexane:ethyl acetate=1:2) and crystallized from hexane to obtain 91 mg of the title compound.

Yield: 17%.
Melting point: 163–165° C.
$^1$H-NMR (CDCl$_3$) δ 1.44 (3H, s), 2.08 (3H, s), 2.26 (3H, s), 2.80–2.96 (3H, m), 3.22 (1H, d, J=15.4 Hz), 3.65 (2H, dd, J=11.7, 20.5 Hz), 4.11 (2H, t, J=8.1 Hz)8.81 (1Hs).

Example 6
8-tert-Butyl-5-(4-fluorobenzoyl)-3,5,6,7-tetrahydro-2,2,4,6,6-pentamethyl-2H-furo[2,3-f]indole 8-tert-Butyl-3, 5, 6, 7-tetrahydro-2,2,4,6,6-pentamethyl-2H-furo[2,3-f]indole hydrochloride (715.8 mg, 2.21 mmol) was suspended in THF (20 ml). To the mixture was added a saturated aqueous solution of sodium hydrogen carbonate (50 ml) and stirred for 1 hour at room temperature. After extracting with isopropyl ether followed by drying over magnesium sulfate, the solvent was removed under reduced pressure. The residue was dissolved in THF (20 ml). To the solution were added triethylamine (0.35 ml, 2.51 mmol) and p-fluorobenzoyl chloride (371.8 mg, 2.34 mmol) and stirred at room temperature for 5 hours. To the reaction mixture was added a saturated aqueous solution of sodium hydrogen carbonate, and extracted with ethyl acetate. The organic layer was washed with a saturated aqueous solution of sodium hydrogen carbonate, dried over magnesium sulfate and concentrated under reduced pressure. The residue was purified by column chromatography on silica gel (hexane:ethyl acetate=10:1) to obtain 417 mg of the title compound as an amorphous powder.

Yield: 46%.
$^1$H-NMR (CDCl$_3$) δ 1.30–1.50 (24H, m), 2.73 (2H, s), 3.17 (2H, s), 6.97–7.06 (2H, m), 7.55–7.61 (2H, m).

Example 7
3,5,6,7-Tetrahydro-2-(iodomethyl)-2,4,8-trimethyl-2H-furo[2,3-f]indole-5-carbaldehyde 2,3-Dihydro-5-hydroxy-4,7-dimethyl-6-(2-methyl-2-propenyl)-1H-indole-1-carbaldehyde (4.17 g, 17.0 mmol) was dissolved in methanol-THF solution (34 ml, 1:1). To the mixture was added calcium carbonate (2.21 g, 22.1 mmol) and then trimethylammonium dichloroiodate (6.51 g, 18.7 mmol) was added. After stirring for 1 hour at room temperature, the reaction mixture was filtered, and the filtrate was concentrated under reduced pressure. The residue was combined a 10% aqueous solution of sodium thiosulfate, and extracted with ethyl acetate. The organic layer was washed with water and saturated brine and dried over sodium sulfate, and the solvent was removed under reduced pressure. The residue was crystallized from ethyl acetate-hexane to obtain 5.52 g of the title compound.

Yield: 88%.

¹H-NMR (CDCl₃) δ 1.67 (3H, s), 2.08 (3H, s), 2.27 (3H, s), 2.93 (2H, t, J=8.1 Hz), 2.99 (1H, d, J=15.8 Hz), 3.26 (1H, d, J=15.8 Hz), 3.43 (2H, s), 4.12 (2H, t, J=8.1 Hz), 8.83 (1H, s).

Example 8

3,5,6,7-Tetrahydro-2-(iodomethyl)-2,4,8-trimethyl-2H-furo[2,3-f]indole 3,5,6,7-Tetrahydro-2-(iodomethyl)-2,4,8-trimethyl-2H-furo[2,3-f]indole-5-carbaldehyde (3.71 g, 10 mmol) was dissolved in methanol (37 ml). To the solution was added concentrated hydrochloric acid, and stirred for 2 hours at 60° C. under argon atmosphere. The mixture was cooled to 0° C., made weakly basic with a saturated aqueous solution of sodium hydrogen carbonate, diluted with water and extracted with ethyl acetate. The organic layer was washed with saturated brine and dried over sodium sulfate, and the solvent was removed under reduced pressure, and this was subjected to chromatography on a small amount of silica gel with eluting with ethyl acetate. The resultant oil was crystallized from hexane to obtain 3.37 g of the title compound.

Yield: 98%.

Melting point: 90–91° C.

¹H-NMR (CDCl₃) δ 1.65 (3H, s), 2.01 (3H, s), 2.07 (3H, s), 2.82 (1H, br), 2.88–3.00 (3H, m), 3.19 (1H, d, J=15.7 Hz), 3.41 (2H,s), 3.55 (2H, t, J=8.3 Hz).

Example 9

3,5,6,7-Tetrahydro-2,4,8-trimethyl-2-[(piperidino)methyl]-2H-furo[2,3-f]indole dihydrochloride To a solution of 3,5,6,7-tetrahydro-2-(iodomethyl)-2,4,8-trimethyl-2H-furo[2,3-f]indole-5-carbaldehyde (371 mg, 1.0 mmol) in toluene (5 ml) was added piperidine (1.48 ml, 15 mmol) and heated to 220° C. for 15 hours under argon in a sealed stainless steel tube. The reaction mixture was cooled to room temperature, diluted with ethyl acetate and washed with water. The organic layer was dried over sodium sulfate, and the solvent was removed under reduced pressure. The residue was purified by basic silica gel column chromatography (hexane:ethyl acetate=1:2) and the resultant oil was treated with 4N hydrogen chloride-ethyl acetate, solution, crystallized from ethyl acetate-ethanol to obtain 276 mg of the title compound.

Yield: 69%.

Melting point: 235–240° C.

NMR data of a free base is shown below.

¹H-NMR (CDCl₃) δ 1.32–1.58 (9H, m), 2.01 (3H, s), 2.05 (3H, s), 2.35–2.62 (6H, m), 2.74 (1H, d, J=15.4 Hz), 2.93 (2H, t, J=8.2 Hz), 3.05 (1H, d, J=15.4 Hz), 3.55 (2H, t, J=8.2 Hz).

Example 10

3,5,6,7-Tetrahydro-2,4,8-trimethyl-2-[(4-phenylpiperidino)methyl]-2H-furo[2,3-f]indole-5-carbaldehyde hydrochloride To a solution of 3,5,6,7-tetrahydro-2-(iodomethyl)-2,4,8-trimethyl-2H-furo[2,3-f]indole-5-carbaldehyde (371 mg, 1.0 mmol) in N,N-dimethylacetamide (5 ml) were added 4-phenylpiperidine (484 mg, 3.0 mmol) and potassium carbonate (415 mg, 3.0 mmol) and stirred for 5 hours at 170° C. under argon atmosphere. The reaction mixture was cooled to room temperature and combined with water and extracted with ethyl acetate. The organic layer was washed three times with saturated brine, dried over sodium sulfate and concentrated under reduced pressure. The residue a, was purified by column chromatography on silica gel (hexane:ethyl acetate 1:1). The resultant oil was treated with 4N hydrogen chloride-ethyl acetate solution, crystallized from ethyl acetate-ethanol to obtain 477 mg of the title compound as an amorphous powder.

Yield: 72%.

Melting point: 199–202° C.

NMR data of a free base is shown below.

¹H-NMR (CDCl₃) δ 1.47 (3H, s), 1.65–1.85 (4H, m), 2.06 (3H, s), 2.16–2.57 (6H, m), 2.59 (2H, s), 2.79–3.09 (4H, m), 3.10–3.25 (2H, m), 4.05–4.18 (2H, m), 7.15–7.34 (5H, m), 8.85 (1H, s).

Example 11

3,5,6,7-Tetrahydro-2,4,8-trimethyl-2-[(4-phenylpiperidino)methyl]-2H-furo[2,3-f]indole 3,5,6,7-Tetrahydro-2,4,8-trimethyl-2-[(4-phenylpiperidino)methyl]-2H-furo[2,3-f]indole-5-carbaldehyde hydrochloride (309 mg, 0.7 mmol) was dissolved in methanol (5 ml). To the solution was added concentrated hydrochloric acid (1 ml) and stirred for 1 hour at 60° C. under argon atmosphere. The reaction mixture was cooled to room temperature, made weakly basic with 12N sodium hydroxide, and extracted with ethyl acetate. The extract was washed with saturated brine and dried over sodium sulfate, and the solvent was removed under reduced pressure. The resultant oil was crystallized from hexane to obtain 203 mg of the title compound.

Yield: 77%.

Melting point: 0.134–136° C.

¹H-NMR (CDCl₃) δ 1.46 (3H, s), 1.71–1.88 (4H, m), 2.03 (3H, s), 2.06 (3H, s), 2.20–2.48 (3H, m), 2.56 (2H, dd, J=13.8, 19.5 Hz), 2.78 (1H, d, J=15.4 Hz), 2.87–3.98 (3H, m), 3.08 (1H, d, J=15.4 Hz), 3.16–3.28 (1H, m), 3.56 (2H, t, J=16.6 Hz), 7.13–7.33 (5H, m).

Example 12

2,3,6,7-Tetrahydro-2-(iodomethyl)-2,4,6,6,8-pentamethyl-5H-furo[2,3-f]indole-5-carbaldehyde To a solution of 2,3-dihydro-5-hydroxy-2,2,4,7-tetramethyl-6-(2-methyl-2-propenyl)-1H-indole-1-carbaldehyde (1.90 g, 6.95 mmol) in dichloromethane (20 ml) and methanol (10 ml) were added calcium carbonate (0.90 g, 9.0 mmol) and benzyltrimethylammonium dichloroiodate (2.66 g, 7.64 mmol), and stirred for 15 minutes at room temperature. The reaction mixture was filtered and concentrated under reduced pressure. To the residue was added a 5% aqueous solution of sodium hydrogen sulfite (15 ml), and extracted twice with ethyl acetate. The organic layers were combined, washed with saturated brine and water, dried over magnesium sulfate, filtered and concentrated under reduced pressure. The residue was recrystallized from ethyl acetate-hexane to obtain 2.40 g of the title compound.

Yield: 86%.

Melting point: 124–126° C.

¹H-NMR (CDCl₃) δ 1.53, 1.57 (3H, s), 1.63, 1.64 (3H, s), 1.67 (3H, s), 2.04 (3H, s), 2.14, 2.25 (3H, s), 2.78, 2.84 (2H, s), 2.99 (1H, d, J=16.0 Hz), 3.26 (1H, d, J=16.0 Hz), 3.43 (2H, s), 8.32, 8.96 (1H, s).

Example 13

3,5,6,7-Tetrahydro-2-(iodomethyl)-2,4,6,6,8-pentamethyl-2H-furo[2,3-f]indole

Example 13

3,5,6,7-Tetrahydro-2-(iodomethyl)-2,4,6,6,8-pentamethyl-2H-furo[2,3-f]indole

To a solution of 2,3,6,7-tetrahydro-2-(iodomethyl)-2,4,6,6,8-pentamethyl-5H-furo[2,3-f]indole-5-carbaldehyde (2.42 g, 6.06 mmol) in methanol (10 ml) was added concentrated hydrochloric acid (3 ml), and heated under reflux for 2.5 hours under nitrogen atmosphere. The reaction mixture was added dropwise to a mixture of sodium hydrogen carbonate (3.7 g, 44 mmol) with water-ethyl acetate, neutralized and extracted three times with ethyl acetate. The organic layers were combined, washed with water and saturated brine, dried over magnesium sulfate, filtered and concentrated under reduced pressure to obtain 2.20 g of the title compound.

Yield: 98%.

An analytical sample was recrystallized from hexane.

Melting point: 100–104° C.

$^1$H-NMR (CDCl$_3$) δ 1.33 (6H, s), 1.64 (3H, s), 1.98 (3H, s), 2.03 (3H, s), 2.10–2.60 (1H, br), 2.76 (2H, s), 2.92 (1H, d, J=15.9 Hz), 3.18 (1H, d, J=15.9 Hz), 3.41 (2H, s).

Example 14

3,5,6,7-Tetrahydro-2,4,6,6,8-pentamethyl-2-[(4-phenylpiperidino)methyl]-2H-furo[2,3-f]indole A suspension of 3,5,6,7-tetrahydro-2-(iodomethyl)-2,4,6,6,8-pentamethyl-2H-furo[2,3-f]indole (1.11 g, 2.99 mmol), 4-phenylpiperidine (723 mg, 4.48 mmol) and potassium carboante (826 mg, 5.98 mmol) in N,N-dimethylacetamide (6 ml) was stirred for 3 hours at 180° C. under nitrogen atmosphere. To the reaction mixture was added water, and extracted three times with ethyl acetate. The organic layers were combined, washed with water and saturated brine, dried over magnesium sulfate, treated with an active charcoal, filtered and then concentrated under reduced pressure. The residue was recrystallized from ethyl acetate-hexane to obtain 744 mg of the title compound.

Yield: 62%.

Melting point: 139–141° C.

$^1$H-NMR (CDCl$_3$) δ 1.33 (6H, s), 1.46 (3H, s), 1.60–1.87 (4H, m), 1.99 (3H, s), 2.01 (3H, s), 2.10–2.50 (3H, m), 2.51 (1H, d, J=13.7 Hz), 2.61 (1H, d, J=13.7 Hz), 2.72–2.84 (1H, m), 2.76 (2H, s), 2.93–3.05 (1H, m), 3.05 (1H, d, J=15.0 Hz), 3.15–3.28 (1H, m), 7.13–7.37 (5H, m).

Example 15;

3,5,6,7-Tetrahydro-2,4,8-trimethyl-2-[(3-phenylpiperidino)methyl]-2H-furo[2,3-f]indole dihydrochloride According to the same manner as that of Example 10, 196 mg of the title compound was obtained starting from 3, 5, 6, 7-tetrahydro-2-(iodomethyl)-2,4,8-trimethyl-2H-furo[2,3-f]indole (343 mg, 1.0 mmol) and 3-phenylpiperidine (322 mg, 2.0 mmol) as an amorphous powder.

Yield: 44%.

NMR data of a free base is shown below.

$^1$H-NMR (CDCl$_3$) δ 1.44–1.46 (3H, m), 1.60–1.78 (2H, m), 1.82–1.93 (1H, m), 2.01 (6H, s), 2.15–2.40 (4H, m), 2.45–2.62 (2H, m), 2.73–3.25 (6H, m), 3.55 (2H, dt, J=2.3, 8.3 Hz), 7.10–7.32 (5H, m).

Example 16

3,5,6,7-Tetrahydro-2,4,6,6,8-pentamethyl-2-(1,2,4,5-tetrahydro-3H-benzazepin-3-ylmethyl)-2H-furo[2,3-f]indole hydrochloride A suspension of 3,5,6,7-tetrahydro-2-(iodomethyl)-2,4,6,6,8-pentamethyl-2H-furo[2,3-f]indole (520 mg, 1.40 mmol), 2,3,4,5-tetrahydro-1H-3-benzazepine (309 mg, 2.10 mmol) and potassium carbonate (387 mg, 2.80 mmol) in N,N-dimethylacetamide (3 ml) was stirred for 3.5 hours at 180° C. under nitrogen atmosphere. Water was added to the reaction mixture and the mixture was extracted twice with ethyl acetate. The organic layers were combined, washed with water and saturated brine, dried over magnesium sulfate, filtered and concentrated under reduced pressure. The residue was subjected to basic silica gel column chromatography (hexane:ethyl acetate=5:1) to obtain an oil. The oil was dissolved in methanol and combined with 10% hydrogen chloride-methanol solution (1.5 ml), and concentrated under reduced pressure. The residue was crystallized from methanol-diisopropyl ether to obtain 269 mg of the title compound.

Yield: 45%.

Melting point: 141–145° C.

$^1$H-NMR (DMSO-d$_6$) δ 1.33 (6H, br s), 1.60 (3H, s), 1.98 (6H, s), 2.53–3.84 (14H, m), 6.93–7.33 (4H, m).

Example 17

3,5,6,7-Tetrahydro-2,4,8-trimethyl-2-[[4-(diphenylmethylamino)piperidino]methyl]-2H-furo[2,3-f]indole-5-carbaldehyde According to the same manner as that of Example 10, 679 mg of the title compound was obtained starting from 3,5,6,7-tetrahydro-2-(iodomethyl)-2,4,8-trimethyl-2H-furo[2,3-f]indole-5-carbaldehyde (371 mg, 1.0 mmol) and N-(diphenylmethyl)-4-piperidinamine (799 mg, 3.0 mmol) as an amorphous powder.

Yield: 89%.

$^1$H-NMR (CDCl$_3$) δ 1.35–1.60 (5H, m), 1.66–1.93 (2H, m), 2.03 (3H, s), 2.05–2.22 (2H, m), 2.25 (3H, s), 2.29–2.46 (1H, m), 2.49 (2H, s), 2.73–3.00 (5H, m), 3.15 (1H, d, J=15.4 Hz), 4.11 (2H, t, J=8.7 Hz), 5.00 (1H, s), 7.15–7.37 (10H, m), 8.83 (1H, s).

Example 18

N-(Diphenylmethyl)-1-[(3,5,6,7-tetrahydro-2,4,8-trimethyl-2H-furo[2,3-f]indol-2-yl)methyl]-4-piperidinamine trihydrochloride According to the same manner as that of Example 11, 487 mg of the title compound was obtained starting from 3,5,6,7-tetrahydro-2,4,8-trimethyl-2-[[4-(diphenylmethylamino)piperidino]methyl]-2H-furo[2,3-f]indole-5-carbaldehyde (510 mg, 1.0 mmol) as an 3 amorphous powder.

Yield: 75%.

NMR data of a free base is shown below.

$^1$H-NMR (CDCl$_3$) δ 1.28–1.46 (5H, m), 1.76–1.97 (4H, m), 2.00 (3H, s), 2.03 (3H, s), 2.05–2.19 (2H, m), 2.28–2.55 (3H, m), 2.69–3.07 (6H, m), 3.54 (2H, t, J=8.2 Hz), 5.01 (1H, s), 7.15–7.39 (10H, m).

Example 19

N-(Diphenylmethyl)-1-[(3,5,6,7-tetrahydro-2,4,6,6,8-pentamethyl-2H-furo[2,3-f]indol-2-yl)methyl]-4-piperidinamine hydrochloride According to the same manner as that of Example 10, the title compound was synthesized starting from 3,5,6,7-tetrahydro-2-(iodomethyl)-2,4,6,6,8-pentamethyl-2H-furo[2,3-f]indole and N-(diphenylmethyl)-4-piperidinamine.

Yield: 92%.

Amorphous Substance $^1$H-NMR (DMSO-d$_6$) δ 1.07–2.26 (4H, m), 1.24 (6H, s), 1.32 (3H, s), 1.88 (3H, s), 1.91 (3H, s), 2.37–3.60 (9H, m), 2.62 (2H, s), 5.35–5.77 (1H, br), 7.10–7.54 (6H, m), 7.54–7.90 (4H, m).

Example 20

3,5,6,7-Tetrahydro-2,4,8-trimethyl-2-[[4-[3-(diphenylmethyloxy) propyl]piperidino]methyl]-2H-furo[2,3-f]indole dihydrochloride According to the same manner as that of Example 10, 338 mg of the title comound was obtained starting from 3,5,6, 7-tetrahydro-2-(iodomethyl)-2,4,8-trimethyl-2H-furo[2,3-f]indole (343 mg, 1.0 mmol) and 4-[3-(diphenylmethyloxy)propyl]piperidine (619 mg, 2.0 mmol) as an amorphous powder.

Yield: 57%.

NMR data of a free base is shown below.

$^1$H-NMR (CDCl$_3$) δ 1.08–1.37 (4H, m), 1.42 (314, m), 1.52–1.75 (4H, m), 2.01 (3H, s), 2.05 (3H, s), 2.06–2.19 (2H, m), 2.40 (1H, br), 2.50 (2H, dd, J=13.8, 18.8 Hz), 2.71–3.08 (6H, m), 3.42 (2H, t, J=6.6 Hz), 3.54 (2H, t, J=8.4 Hz), 5.32 (1H,s), 7.17–7.37 (10H, s).

Example 21
N-Methyl-N-[1-[(3,5,6,7-tetrahydro-2,4,6,6,8-pentamethyl-2H-furo[2,3-f]indol-2-yl)methyl]-4-piperidinyl]-1,3-benzothiazole-2-amine A suspension of 3,5,6,7-tetrahydro-2-(iodomethyl)-2,4,6,6,8-pentamethyl-2H-furo[2,3-f]indole (372 mg, 1.00 mmol), N-methyl-N-(4-piperidinyl)-1,3-benzothiazole-2-amine hydrochloride (427 mg, 1.50 mmol) and potassium carbonate (485 mg, 3.51 mmol) in N,N-dimethylacetamide (2 ml) was stirred for 4.5 hours at 180° C. under nitrogen atmosphere. Water was added to the reaction mixture and the mixture was extracted twice with ethyl acetate. The organic layers were combined, washed with water and saturated brine, dried over magnesium sulfate, filtered and concentrated under reduced pressure. The residue was subjected to basic silica gel column chromatography (hexane:ethyl acetate=5:1) and crystallized from ethyl acetate-hexane to obtain 231 mg of the title compound.

Yield: 47%.

Melting point: 147–150° C.

$^1$H-NMR (CDCl$_3$) δ 1.33 (3H, s), 1.34 (3H, s), 1.45 (3H, s), 1.62–1.95 (4H, m), 1.99 (3H, s), 2.00 (3H, s), 2.25–2.44 (2H, m), 2.50 (1H, d, J=13.9 Hz), 2.60 (1H, d, J=13.9 Hz), 2.70–2.84 (1H, m), 2.76 (2H, s), 2.94–3.10 (2H, m), 3.06 (3H, s), 3.15–3.30 (1H, m), 3.83–4.04 (1H, m), 7.03 (1H, td, J=7.5, 1.1 Hz), 7.21–7.32 (1H, m), 7.55 (2H, t, J=7.7 Hz).

Example 22
3,5,6,7-Tetrahydro-2,2,4,8-tetramethyl-3-(4-methylphenyl)-2H-furo[2,3-f]indole A solution of 1-acetyl-4,7-dimethyl-5-[[2-methyl-3-(4-methylphenyl)-2-propenyl]oxy]-1,2-dihydro-1H-indole (1.74 g, 5.0 mmol) in N,N-diethylaniline (5.2 ml) was stirred for 5 hours at 220° C. under argon atmosphere. After cooling to room temperature, the mixture was diluted with ethyl acetate and washed with 1N hydrochloric acid. The organic layer was washed with saturated brine and dried over sodium sulfate and the solvent was removed under reduced pressure. The residue was purified by column chromatography on silica gel (hexane:ethyl acetate=1:1). To the resultant oil were added isobutyl alcohol (5 ml) and concentrated hydrochloric acid (5 ml) and stirred for 3 hours at 120° C. under argon atmosphere. After cooling to 0° C., the mixture was neutralized with 12 N sodium hydroxide, extracted with ethyl acetate. The organic layer was washed with saturated brine and dried over sodium sulfate, and the solvent was removed under reduced pressure. The residue was purified by column chromatography on silica gel (hexane:ethyl acetate=2:1), and the solvent was removed under reduced pressure followed by a crystallization from hexane yielded 0.49 g of the title compound.

Yield: 35%.

Melting point: 135–136° C.

$^1$H-NMR (CDCl$_3$) δ 1.00 (3H, s), 1.48 (3H, s), 1.70 (3H, s), 2.14 (3H, s), 2.30 (3H, s), 2.98 (2H, d, J=8.5 Hz), 3.25 (1H, br), 3.56 (2H, d, J=8.5 Hz), 4.05 (1H, s), 6.85 (2H, br), 7.04 (2H, d, J=7.6 Hz).

The structure of each compound obtained in Examples 1 to 22 is shown in Table 1.

TABLE 1

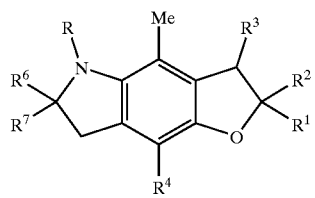

| Sample number | R | R$^1$ | R$^2$ | R$^3$ | R$^4$ | R$^6$ | R$^7$ | Salt |
|---|---|---|---|---|---|---|---|---|
| 1 | H | Me | Me | H | Me | H | H | |
| 2 | COCH$_3$ | Me | Me | H | Me | Me | H | |
| 3 | H | Me | Me | H | Me | Me | H | |
| 4 | H | Me | Me | H | $^t$Bu | Me | Me | HCl |
| 5 | CHO | Me | CH$_2$OH | H | Me | H | H | |
| 6 | CO—⟨C$_6$H$_4$⟩—F | Me | Me | H | $^t$Bu | Me | Me | |
| 7 | CHO | Me | CH$_2$I | H | Me | H | H | |
| 8 | H | Me | CH$_2$I | H | Me | H | H | |
| 9 | H | Me | —N(piperidine) | H | Me | H | H | 2HCl |

TABLE 1-continued

Structure: bicyclic scaffold with R on N (top-left), Me on aromatic ring, R³ and R² on furan ring, R¹ on furan oxygen-adjacent carbon, R⁴ on aromatic ring, R⁶ and R⁷ on pyrrolidine ring carbon.

| Sample number | R | R¹ | R² | R³ | R⁴ | R⁶ | R⁷ | Salt |
|---|---|---|---|---|---|---|---|---|
| 10 | CHO | Me | N-ethylpiperidin-4-yl with 4-Ph | H | Me | H | H | HCl |
| 11 | H | Me | N-ethylpiperidin-4-yl with 4-Ph | H | Me | H | H | |
| 12 | CHO | Me | CH₂I | H | Me | Me | Me | |
| 13 | H | Me | CH₂I | H | Me | Me | Me | |
| 14 | H | Me | N-ethylpiperidin-4-yl with 4-Ph | H | Me | Me | Me | |
| 15 | H | Me | N-ethylpiperidin-3-yl with 3-Ph | H | Me | H | H | 2HCl |
| 16 | H | Me | N-ethyl-2,3,4,5-tetrahydro-1H-benzo[d]azepin-3-yl | H | Me | Me | Me | HCl |
| 17 | CHO | Me | N-ethylpiperidin-4-yl-NH-CHPh₂ | H | Me | H | H | |
| 18 | H | Me | N-ethylpiperidin-4-yl-NH-CHPh₂ | H | Me | H | H | 3HCl |
| 19 | H | Me | N-ethylpiperidin-4-yl-NH-CHPh₂ | H | Me | Me | Me | HCl |
| 20 | H | Me | N-ethylpiperidin-4-yl-(CH₂)₃-O-CHPh₂ | H | Me | H | H | 2HCl |

TABLE 1-continued

[Structure: bicyclic compound with substituents R, R³, R⁶, R⁷ on pyrrolidine-fused ring with Me group, R², R¹ on furan ring, R⁴ substituent]

| Sample number | R | R¹ | R² | R³ | R⁴ | R⁶ | R⁷ | Salt |
|---|---|---|---|---|---|---|---|---|
| 21 | H | Me | Me (N-ethylpiperidin-4-yl)(N-methyl)amino-benzothiazol-2-yl | H | Me | Me | Me | |
| 22 | H | Me | Me | 4-MePh | Me | H | H | |

Formulation Example 1

| | | |
|---|---|---|
| (1) Example compound 11 | 10.0 g |
| (2) Lactose | 60.0 g |
| (3) Corn starch | 35.0 g |
| (4) Gelatin | 3.0 g |
| (5) Magnesium stearate | 2.0 g |

A mixture of 10.0 g of the compound, 60.0 g of lactose and 35.0 g of the corn starch, and 30 ml of a 10% by weight aqueous solution of gelatin (3.0 g as gelatin) was granulated through a 1 mm mesh sieve, dried at 40° C. and then sieved again. The resultant granule was mixed with 2.0 g of magnesium stearate, and compressed. The resultant core was coated with a sugar coating which was an aqueous suspension of sucrose, titanium dioxide, talc and gum arabic. A coated tablet was imparted with a gloss using a beeswax, to obtain 100 coated tablets.

Formulation Example 2

| | |
|---|---|
| (1) Example compound 11 | 10.0 g |
| (2) Lactose | 70.0 g |
| (3) Corn starch | 50.0 g |
| (4) Soluble starch | 7.0 g |
| (5) Magnesium stearate | 3.0 g |

10.0 g of the compound and 3.0 g of magnesium stearate were granulated using 70 ml of an aqueous solution of the soluble starch (7.0 g as soluble starch), dried, and combined with 70.0 g of the lactose and 50.0 g of the corn starch. The mixture was compressed to obtain 1000 tablets.

Formulation Example 3

| | |
|---|---|
| (1) Example compound 11 | 1.0 g |
| (2) Lactose | 60.0 g |
| (3) Corn starch | 35.0 g |
| (4) Gelatin | 3.0 g |
| (5) Magnesium stearate | 2.0 g |

A mixture of 1.0 g of the compound, 60.0 g of the lactose and 35.0 g of the corn starch was granulated through a 1-mm mesh sieve using 30 ml of a 10% by weight aqueous solution of gelatin (3.0 g as gelatin), dried at 40° C. and then sieved again. The resultant granule was mixed with 2.0 g of magnesium stearate, and compressed. The resultant core was coated with a sugar coating which was an aqueous suspension of sucrose, titanium dioxide, talc and gum arabic. A coated tablet was imparted with a gloss using a beeswax, to obtain 100 coated tablets.

Experiment

Inhibitory Effect on Lipid Peroxidation in Rat Cerebral Cortical Homogenates and Orally Treated Mice Quantitative determination of lipoperoxide produced in brain homogenate was performed according to the method of Stocks et al. (Clin. Sci. Mol. Med. 47–215(1974)). As animals, brains of Jcl. Wistar male rats, 10–13 weeks age, were used. Rat cerebral cortices were obtained after decapitation, homogenized in an ice-cooled phosphate saline buffer (50 mM Ph 7.4) (Nichion Microhomogenizer, S-310E), centrifuged at 10,000 g for 10 minutes (Hitachi CF15D type, RT15A6 Anglerotor), and the supernatant was used in a test. This supernatant was diluted 3-fold with the same buffer. To this 1 mL were added 10 pL of test drugs dissolved in dimethyl sulfoxide (DMSO) to the final concentration of 0.0125, 0.025, 0.05, 0.10, 0.20, 0.40, 0.80 and 1.60 µM, respectively, which was incubated at 37° C. for 30 minutes. The reaction was stopped by addition of 200 µL of 35% perchloric acid, and centrifuged at 13,000 g for 10 minutes. To 1 mL of this supernatant was added 0.5 mL of 2-thiobarbituric acid (500 mg/100 mL) dissolved in 50% acetic acid, heated to boil at 95° C. for 15 minutes, which was determined by the absorbance at 532 nm. An inhibition rate was obtained from an amount of produced lipoperoxide at each concentration of the compound and an amount of lipoperoxide in a DMSO-added group, and $IC_{50}$ value of a compound was obtained from the inhibition rate.

The results are shown in Table 2.

TABLE 2

| Example number | IC$_{50}$ ($\mu$M) |
|---|---|
| 11 | 0.067 |
| 18 | 0.36 |

Based on the results described above, Compound (I) was proven to have an excellent lipid peroxidation-inhibiting effect.

INDUSTRIAL APPLICABILITY

Compound (I) or (I') of the present invention has an excellent inhibitory activity of lipid peroxidation, and is useful as a lipid peroxidation inhibitor.

What is claimed is:

1. A compound represented by the formula:

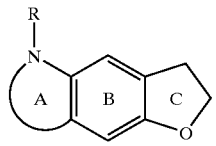

wherein Ring A is a non-aromatic 5- to 7-membered nitrogen-containing heterocyclic ring which may be further substituted, Ring B is benzene ring which is further substituted, Ring C is a dihydrofuran ring which may be further substituted and R is hydrogen atom or an acyl group, or a salt thereof.

2. The compound according to claim 1, wherein Ring A is a non-aromatic 5- to 7-membered nitrogen-containing heterocyclic ring which may be further substituted by an unsubstituted or substituted hydrocarbon group.

3. The compound according to claim 1, wherein Ring A is a non-aromatic 5- to 7-membered nitrogen-containing heterocyclic ring which may be further substituted by an unsubstituted or substituted lower alkyl group.

4. The compound according to claim 1, wherein Ring A is a non-aromatic 5- to 7-membered nitrogen-containing heterocyclic ring which may be further substituted by a lower alkyl group.

5. The compound according to claim 1, wherein Ring A is a non-aromatic 5-membered nitrogen-containing heterocyclic ring which may be further substituted by a lower alkyl group.

6. The compound according to claim 1 which is represented by the formula:

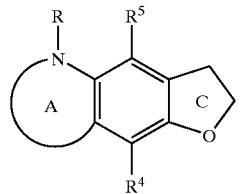

wherein R$^4$ and R$^5$ are the same or different and each denotes hydrogen atom, a halogen atom, hydroxy group, amino group or a hydrocarbon group which may be bonded directly or via oxygen atom, nitrogen atom or sulfur atom and which may be substituted, and the other symbols are as defined in claim 1, provided that both R$^4$ and R$^5$ are not hydrogen atoms at the same time, or a salt thereof.

7. The compound according to claim 6, wherein R$^4$ and R$^5$ are the same or different and each denotes a lower alkyl group or a lower alkoxy group.

8. The compound according to claim 6, wherein each of R$^4$ and R$^5$ is a lower alkyl group.

9. The compound according to claim 1 which is represented by the formula:

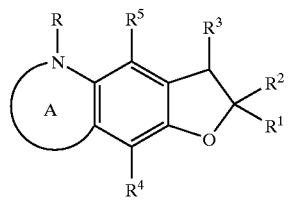

wherein R$^1$ and R$^2$ are the same or different and each denotes hydrogen atom, an unesterified, esterified, unamidated or amidated carboxyl group or an unsubstituted or substituted hydrocarbon group, R$^3$ is hydrogen atom, an unsubstituted or substituted hydrocarbon group or an unsubstituted or substituted amino group, and the other symbols are as defined in claim 5, or a salt thereof.

10. The compound according to claim 9, wherein R$^1$ is a lower alkyl group, R$^2$ is a lower alkyl group which may be substituted by a halogen atom, hydroxy group or an unsubstituted or substituted cyclic amino group and R$^3$ is hydrogen atom or an unsubstituted or substituted phenyl group.

11. The compound according to claim 9, wherein R$^1$ is a lower alkyl group, R$^2$ is a lower alkyl group which may be substituted by a halogen atom, hydroxy group or an unsubstituted or substituted cyclic amino group, R$^3$ is hydrogen atom or an unsubstituted or substituted phenyl group, each of R$^4$ and R$^5$ is a lower alkyl group, and Ring A is a non-aromatic 5- to 7-membered nitrogen-containing heterocyclic ring which may be further substituted by a lower alkyl group.

12. The compound according to claim 9, wherein R$^1$ is a lower alkyl group, R$^2$ is a lower alkyl group which may be substituted by a halogen atom, hydroxy group or unsubstituted or substituted cyclic amino group, R$^3$ is hydrogen atom or an unsubstituted or substituted phenyl group, each of R$^4$ and R$^5$ is a lower alkyl group, and Ring A is a non-aromatic 5-membered nitrogen-containing heterocyclic ring which may be further substituted by a lower alkyl group.

13. 8-Tert-butyl-3,5,6,7-tetrahydro-2,2,4,6,6-pentamethyl-2H-furo[2,3-f]indole or a salt thereof.

14. 3,5,6,7-Tetrahydro-2,4,8-trimethyl-2-[(4-phenylpiperidino)methyl]-2H-furo[2,3-f]indole or a salt thereof.

15. 3,5,6,7-Tetrahydro-2,4,6,6,8-pentamethyl-2-[(4-phenylpiperidino)methyl]-2H-furo[2,3-f]indole or a salt thereof.

16. 3, 5, 6, 7-Tetrahydro-2,2,4,8-tetramethyl-3-(4-methylphenyl)-2H-furo[2,3-f]indole or a salt thereof.

17. A pharmaceutical composition comprising a compound represented by the formula:

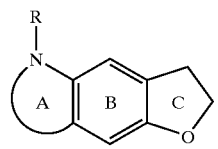

wherein Ring A is a non-aromatic 5- to 7-membered nitrogen-containing heterocyclic ring which may be further substituted,
Ring B is benzene ring which is further substituted,
Ring C is a dihydrofuran ring which may be further substituted and
R is hydrogen atom or an acyl group,
or a salt thereof
and a pharmaceutically acceptable carrier.

18. A method for inhibiting lipid peroxidation which comprises administering an effective amount of a compound represented by the formula:

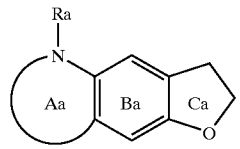

wherein Ring Aa is a non-aromatic 5- to 7-membered nitrogen-containing heterocyclic ring which may be further substituted, Ring Ba is benzene ring which may be further substituted, Ring Ca is a dihydrofuran ring which may be further substituted and Ra is hydrogen atom or an acyl group, or a salt thereof to a mammal.

19. A method for treating cranial trauma which comprises administering a compound represented by the formula:

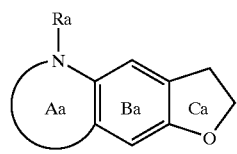

wherein Ring Aa is a non-aromatic 5- to 7-membered nitrogen-containing heterocyclic ring which may be further substituted, Ring Ba is benzene ring which is further substituted, Ring Ca is a dihydrofuran ring which may be further substituted and Ra is hydrogen atom or an acyl group, or a salt thereof to a mammal.

20. A process for preparing the compound according to claim 1 or a salt thereof which comprises subjecting a substituent X and hydroxy group on Ring B of a compound represented by the formula:

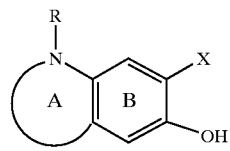

wherein X is an unsubstituted or substituted allyl group, and the other symbols are as defined in claim 1 or a salt thereof to a ring-closure reaction.

* * * * *